United States Patent [19]
DiMaio et al.

[11] Patent Number: 6,060,451
[45] Date of Patent: May 9, 2000

[54] THROMBIN INHIBITORS BASED ON THE AMINO ACID SEQUENCE OF HIRUDIN

[75] Inventors: John DiMaio, Montreal; Yasuo Konishi, Kirkland; Feng Ni, Pierrefonds, all of Canada; Torsten Steinmetzer, Jena, Germany

[73] Assignee: The National Research Council of Canada, Ottawa, Canada

[21] Appl. No.: 08/406,142

[22] Filed: Mar. 20, 1995

Related U.S. Application Data

[62] Continuation-in-part of application No. 08/302,245, Sep. 8, 1994, abandoned, which is a continuation of application No. 07/960,425, filed as application No. PCT/CA91/00213, Jun. 14, 1991, abandoned, which is a continuation-in-part of application No. 07/538,322, Jun. 15, 1990, abandoned.

[51] Int. Cl.$^7$ .................................................. A61K 38/00
[52] U.S. Cl. ................................. 514/13; 514/14; 514/15; 514/16; 514/17; 530/325; 530/326; 530/327; 530/328; 530/329; 530/332
[58] Field of Search ........................ 514/13–17; 530/325, 530/329, 332

[56] References Cited

U.S. PATENT DOCUMENTS

| | | | |
|---|---|---|---|
| 5,196,404 | 3/1993 | Maraganore et al. | 514/13 |
| 5,240,913 | 8/1993 | Maraganore et al. | 514/13 |

FOREIGN PATENT DOCUMENTS

| | | |
|---|---|---|
| 43655/85 | 12/1985 | Australia . |
| 0 129 163 | 12/1984 | European Pat. Off. . |
| 0 276 014 | 7/1988 | European Pat. Off. . |
| 0 291 982 | 11/1988 | European Pat. Off. . |
| 0 333 356 | 9/1989 | European Pat. Off. . |
| 0 341 607 | 11/1989 | European Pat. Off. . |
| 0 352 227 | 1/1990 | European Pat. Off. . |
| 0 352 228 | 1/1990 | European Pat. Off. . |
| 91/01142 | 2/1991 | WIPO . |
| 91/01328 | 2/1991 | WIPO . |
| 91/02750 | 3/1991 | WIPO . |

OTHER PUBLICATIONS

Krstenansky et al., Antithrombin Properties of C–Terminus of Hirudin Using Synthetic Unsulfated N$^\alpha$–acetyl–hirudin$_{45-65}$, *FEBS Letters*, vol. 211, No. 1, pp. 10–16 (Jan. 1987).

Krstenansky et al., "Anticoagulant Peptides: Nature of the Interaction of the C–Terminal Region of Hirudin with a Noncatalytic Binding Site on Thrombin," *J. Med. Chem*, vol. 30, No. 9, pp. 1688–1691 (1987).

Dodt et al., "Interaction of Site Specific Hirudin Variants with α–Thrombin,"*FEBS Letters*, vol. 229, No. 1, pp. 87–90 (Feb. 1988).

Markwardt, "Pharmacology of Selective Thrombin Inhibitors", *Nouv. Rev. Fr. Hematol.*, vol. 30, pp. 161–165 (1988).

Braun et al., "Use of Site–Directed Mutagenesis to Investigate the Basis for the Specificity of Hirudin," *Biochemistry*, vol. 27, No. 17, pp. 6517–6522 (1988).

Maraganore et al., "Anticoagulant Activity of Synthetic Hirudin Peptides," *Journal of Biological Chemistry*, vol. 264, No. 15, pp. 8692–8698 (May 1989).

Degryse et al., "Point Mutations Modifying the Thrombin Inhibition Kinetics and Antithrombotic Activity in vivo, of Recombinant Hirudin," *Protein Engineering*, vol. 2, No. 6, pp. 459–465 (1989).

Dodt et al., "Distinct Binding Sites of Ala$^{48}$–Hirudin$^{1-47}$ and Ala$^{48}$–Hirudin$^{48-65}$ on α–Thrombin," *The Journal of Biological Chemistry*, vol. 265, No. 2, pp. 713–718 (Jan. 1990).

Chang et al., "The Structural Elements of Hirudin which Bind to the Fibrinogen Recognition Site of Thrombin Are Exclusively Located within its Acidic C–Terminal Tail," *FEBS Letters*, vol. 261, No. 2, pp. 287–290 (1990).

Dennis et al., "Use of Fragments of Hirudin to Investigate Thrombin–Hirudin Interaction," *Eur. J. Biochem.*, vol. 188, pp. 61–66 (1990).

Stone et al., "Kinetics of the Inhibition of Thrombin by Hirudin," *Biochemistry*, vol. 25, No. 16, pp. 4622–4628 (1986).

Hanson et al., "Interruption of Acute Platelet–Dependent Thrombosis by the Synthetic Antithrombin D–Phenylalanyl–L–Prolyl–L–Arginyl Chloromethyl Ketone," *Proc. Natl. Acad. Sci. USA*, vol. 85, pp. 3184–3188 (1988).

DiMaio et al., "Bifunctional Thrombin Inhibitors Based on the Sequence of Hirudin$^{45-65}$," *The Journal of Biological Chemistry*, vol. 265, No. 35, pp. 21698–21703 (Dec. 1990).

DiMaio et al., "A New Class of Potent Thrombin Inhibitors that Incorporates a Scissile Pseudopeptide Bond," *The Journal of Biological Chemistry*, vol. 282, No. 1, pp. 47–52 (Apr. 1991).

Seemüller et al., "Proteinase Inhibitors of the Leech *Hirudo medicinalis* (Hirudins, Bdellins, Eglins)." No year given.

Hauptmann et al., "Antiocoagulant and Antithrombotic Action of Novel Specific Inhibitors of Thrombin," pp. 118–123, no year given.

Wallis "Hirudins and the Role of Thrombin: Lessons from Leeches," *TIPS*, vol. 9, pp. 425–427 (Dec. 1988).

(List continued on next page.)

*Primary Examiner*—Cecilia J. Tsang
*Assistant Examiner*—C. Delacroix-Muirheid
*Attorney, Agent, or Firm*—Foley & Lardner

[57] ABSTRACT

A thrombin inhibitor comprising a first bulky hydrophobic portion interacting with the catalytic site of thrombin responsible for proteolysis and a second portion at least maintaining the hydrophobic and acidic character of amino acids 55 to 60 of native hirudin at the C-terminal noncatalytic region of N-acetyl-hirudin45–65. Between the first and second portions is a divalent linker moiety having a chain length of at least 10 carbon atoms. Connecting the first bulky hydrophobic portion and the linker is a peptidomimetic bond. Preferably, the bulky hydrophobic portion comprises at least one amino acid of D-configuration. The compounds are useful in the treatment of thrombotic disorders.

53 Claims, 6 Drawing Sheets

OTHER PUBLICATIONS

Bode et al., "The Refined 1.9 Å Crystal Structure of Human α–Thrombin: Interactin with D–Phe–Pro–Arg Chloromethylketone and Significance of the Tyr–Pro–Pro–Trp Insertion Segment," *The EMBO Journal*, vol. 8, No. 11, pp. 3467–3475 (1989).

Grütter et al., "Crystal Structure of the Thrombin–Hirudin Complex: A Novel Mode of Serine Protease Inhibition," *The EMBO Journal*, vol. 9, No. 8, pp. 2361–2365 (1990).

Maraganore et al., "Design and Characterization of Hirulogs: A Novel Class of Bivalent Peptide Inhibitors of Thrombin," *Biochemistry*, vol. 29, No. 30, pp. 7095–7101 (1990).

DiMaio et al., "Design of Bifunctional Thrombin Inhibitors Based on the Sequence of Hirudin$^{45-65}$," *Peptides 1990*, ESCOM, pp. 774–776 (1991).

Cadroy et al., "Selective Inhibition by a Synthetic Hirudin Peptide of Fibrin–Dependent Thrombosis in Baboons," *Proc. Natl. Acad. Sci. USA*, vol. 88, pp. 1177–1181 (Feb. 1991).

Morison & Boyd, Organic Chemistry, pp. 180–181, 585–586.

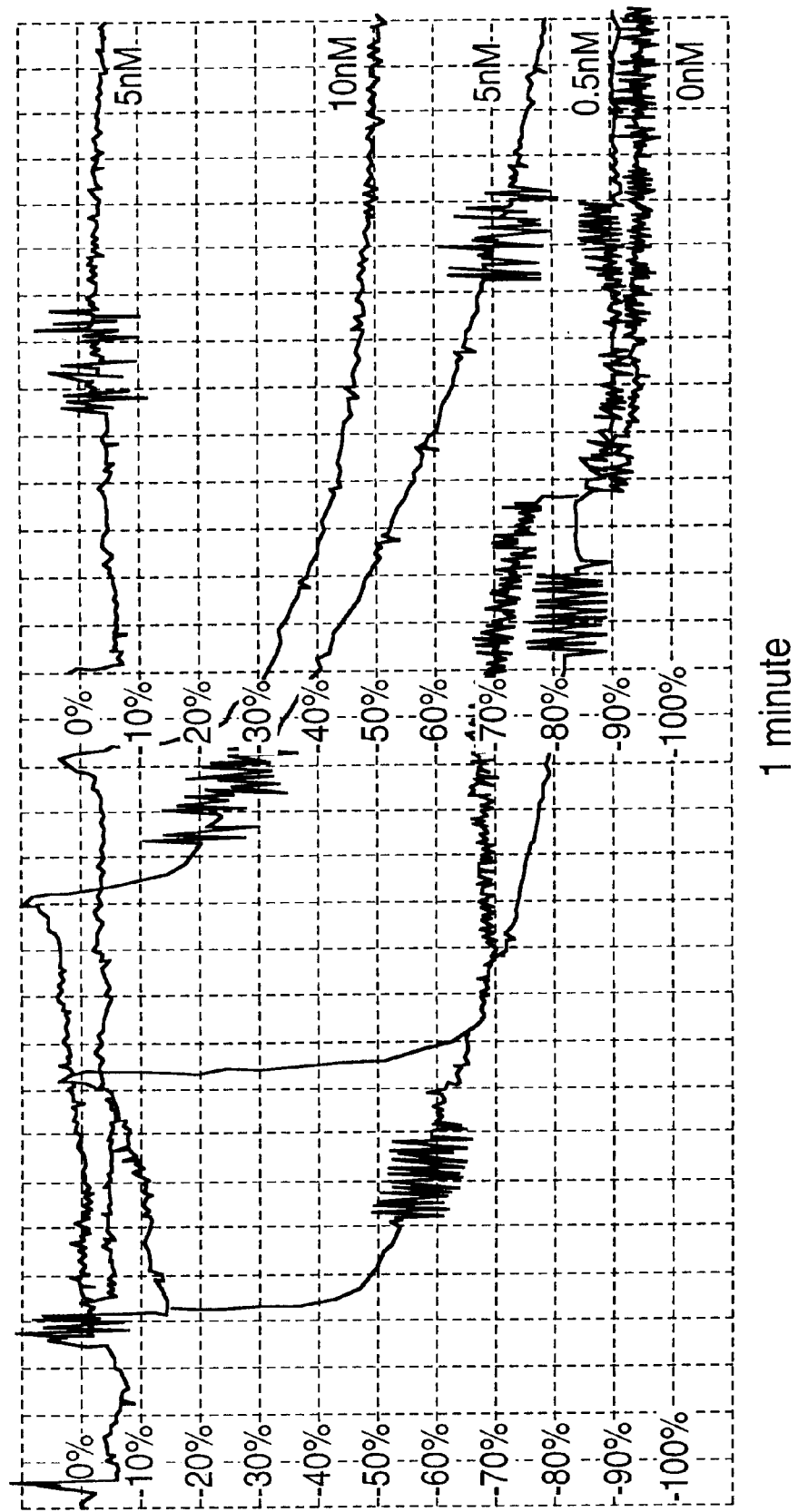

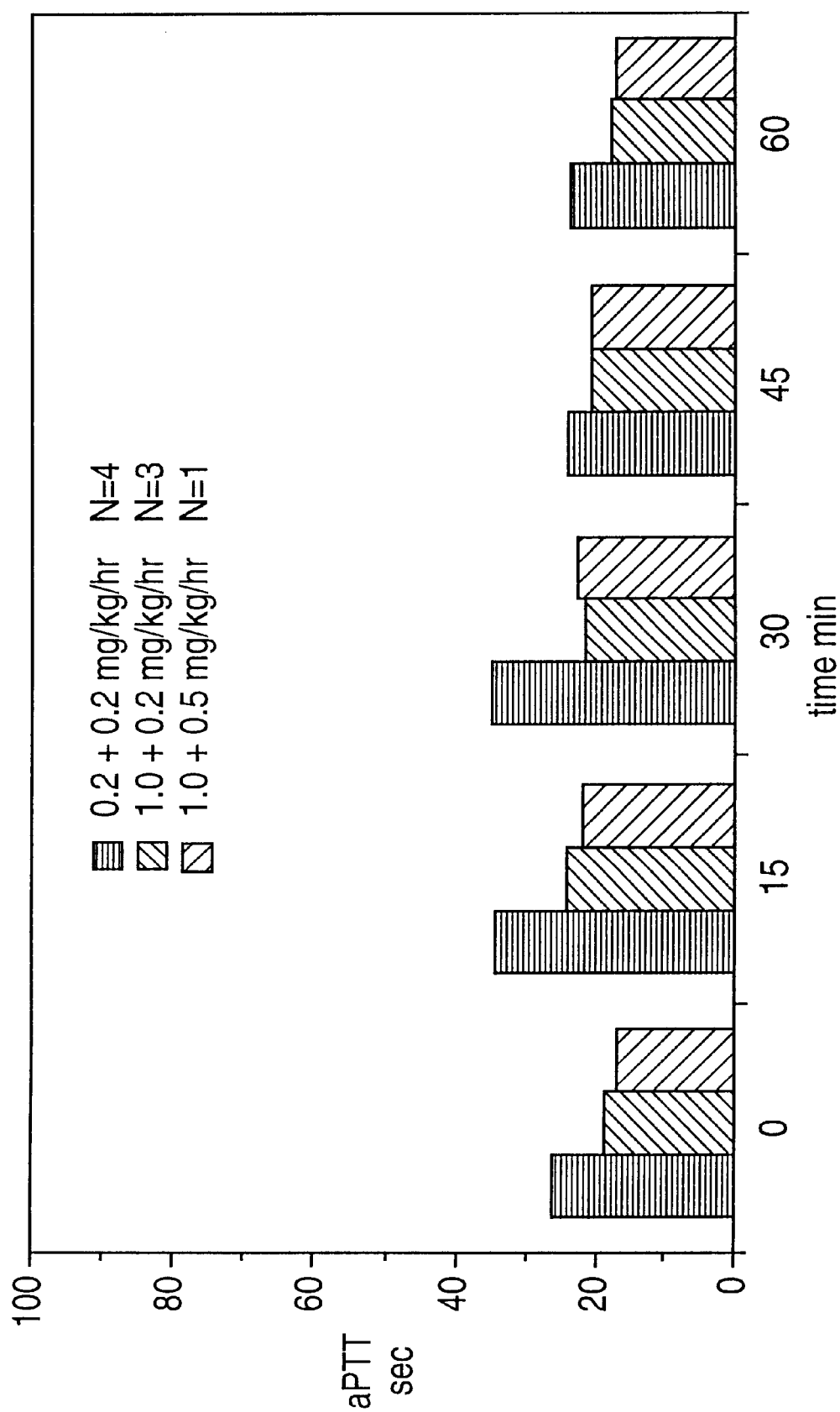

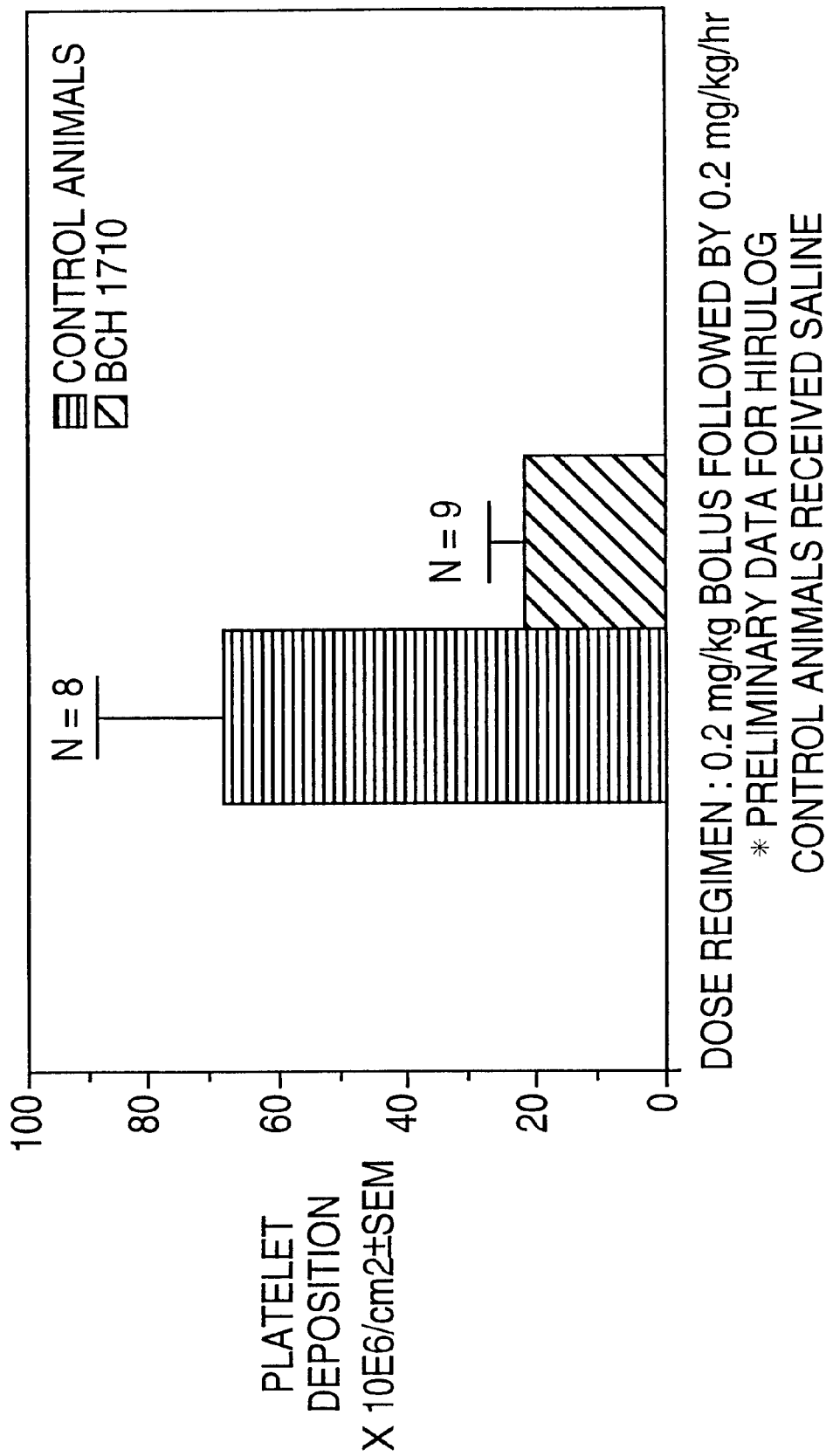

THROMBIN INHIBITORS BASED ON THE AMINO ACID SEQUENCE OF HIRUDIN

This is a continuation-in-part of U.S. application Ser. No. 08/302,245 (hereby incorporated by reference) filed on Sep. 8, 1994, now abandoned, which is a continuation of application Ser. No. 07/960,425 filed Feb. 10, 1993, now abandoned, which is the national stage filing of PCT/CA91/00213 filed on Jun. 14, 1991 now abandoned, which is itself a continuation-in-part of U.S. application Ser. No. 07/538,322 filed on Jun. 15, 1990, now abandoned.

FIELD OF THE INVENTION

The present invention relates to peptide derivatives useful as thrombin inhibitors. The peptides of the present invention are designated "bifunctional" thrombin inhibitors as they attach to two different binding sites on the thrombin molecule.

These peptides are based on the sequence of the segment of hirudin containing amino acids 45 to 65 having appropriate modifications conferring enhanced binding up to six orders of magnitude greater than the corresponding native peptide fragment.

One such modification in the segment of hirudin includes the use of a peptidomimetic bond in the area corresponding to the bond between amino acids 47–48 in the hirudin sequence.

Another such modification is the elimination of an amino acid corresponding to amino acid 48 in the hirudin sequence.

The present invention also relates to methods of treatment of cardiovascular disorders, or prevention of cancer metastases using these peptides. The peptides of the invention may also serve as diagnostic tools in vivo for detecting cardiovascular disorders, for treatment of blood circulating ex vivo, and for in vitro use as anticoagulant for extracorporeal blood.

BACKGROUND OF THE INVENTION

Thrombin is an important serine proteinase component of the blood coagulation cascade. Besides initiating blood clotting by cleaving fibrinogen, thrombin activates other hemocoagulant factors including factors V, VIII and XIII and the anticoagulant enzyme protein C. Thrombin is also a potent platelet activator that impairs thrombolysis mediated by tissue plasminogen activator in vivo. Thus, thrombin's positive feedback regulation serves to amplify hemostatic events but causes life-threatening thrombi in response to aberrations with vascular and cerebrovascular arteries.

Given the diverse functions of this enzyme, its inhibition by potent and specific compounds could provide an invaluable addition to the treatment of disorders related to thrombosis. These include: coronary artery disease, cerebrovascular disease, peripheral arterial occlusive disease, deep vein thrombosis, and pulmonary embolism.

The most potent inhibitor of thrombin known is hirudin, a family of iso-proteins isolated from the glandular secretions of the leech *Hirudo medicinalis*. The anticoagulant properties of hirudin have been known for a long time. However, it has so far been of little therapeutic value since the formulation of this protein in a readily efficient and administrable form seems to be difficult as both enteral and cutaneous absorptions are very low so it has not been possible to produce adequate levels of the protein in the bloodstream.

Furthermore, clinical use of hirudin isolated from leech extracts is unlikely because of its limited quantity, expense, and allergic reactions which may commonly occur upon administration of foreign proteins having the size of hirudin.

In his publication entitled "Pharmacology of selective thrombin inhibitors", (1988), Nouv. Rev. Fr. Hematol., 30, pages 161–165, Markwardt provided further clinical information on hirudin based on results of pharmacological studies performed for both natural and synthetic thrombin inhibitors.

The author makes general observations concerning hirudin, mentioning that the peptide, which contains a highly acidic C-terminal portion, is highly specific for α-thrombin. He then concludes that the C-terminal portion of hirudin is likely to bind to the anionic binding site region of the enzyme whereas the compact N-terminal portion appears to bind to the active site region of the enzyme.

It has been found that native desulfo hirudin$^{45\text{-}65}$ inhibits fibrinogen clotting by both bovine and human α-thrombin in a dose dependent manner. The $IC_{50}$ value of 940±200 nM for bovine α-thrombin is in good agreement with the reported value of plasma fibrin clot formation by the same fragment and three times lower than hirudin$^{55\text{-}65}$, which had been assigned as the minimum core required for anticoagulant activity. It has also been demonstrated that the same peptides were consistently more potent against human α-thrombin than bovine α-thrombin.

Various prior art documents have also demonstrated that the active fragment of the amino acid sequence of hirudin appears to be the amino acid sequence including amino acids 45 to 65. Hence, efforts have been made to enhance the inhibitory activities of the peptide by substituting some of the amino acids present in this sequence.

Krstenansky et al., in "Antithrombin properties of C-terminus of hirudin using synthetic unsulfated Nα-acetyl-hirudin", (1987), Febs Letters, Vol. 211, No. 1, pages 10–16, describe the synthesis of the C-terminal fragment unsulfated Nα-acetyl-hirudin$^{45\text{-}65}$. The authors refer to previous work (Chang, J.-V., FEBS Letters, 164, 307 (1983)) and mention that this fragment could potentially contain two specific binding domains, one binding to the catalytic site of thrombin and the other binding to another recognition site on thrombin. This was concluded not to be the case by either authors.

Still, the authors demonstrated that the 45–65 sequence of hirudin has the ability to inhibit clotting activity as well as the release of fibrinopeptide A by thrombin. They also suggested that the same sequence of hirudin$^{45\text{-}65}$ may not be directly involved in the binding with the catalytic site of thrombin since the amidolytic properties of thrombin toward synthetic substrates is not perturbed.

In the Krstenansky et al. article entitled "Anticoagulant peptides: nature of the interaction of the C-terminal region of hirudin with a noncatalytic site on thrombin", (1987), J. Med. Chem., 30, pages 1688–1691, the authors report that the minimum active sequence at the noncatalytic binding site of thrombin is hirudin$^{56\text{-}64}$. Based on this assumption, the authors report the synthesis of several C-terminal hirudin$^{54\text{-}65}$ analogs and their ability to inhibit thrombin-induced fibrin clot formation for the purpose of establishing the nature of the interaction between hirudin$^{56\text{-}64}$ and a noncatalytic binding site of thrombin.

In their conclusion, the authors mention that the C-terminal region of hirudin may bind to a region of fibrinogen binding on thrombin that is not the region proposed so far in the literature.

In the articles by Dodt et al. (Interaction of site specific hirudin variants with α-thrombin, (1988), Febs Letters, Vol.

229, No. 1, pages 87–90), Degryse et al. (Point mutations modifying the thrombin inhibition kinetics and antithrombotic activity in vivo of recombinant hirudin, (1989), Protein Engineering, Vol. 2, No. 6, pages 459–465) and Braun et al. (Use of site-directed mutagenesis to investigate the basis for the specificity of hirudin, (1988), Biochemistry, 27, pages 6517–6522), the authors report the results of site-directed mutagenesis performed on the hirudin gene. The inhibition of thrombin by mutant hirudin peptides is studied.

In these publications, the authors studied mutations effected on the whole protein and did not restrict themselves to the 45–65 segment of hirudin. Furthermore, the modifications performed on the 45–65 segment were restricted to a single modification, usually at position 47, to illustrate that this residue does not interact with the active site, although these publications also show mutations at positions 51, 57, 58, 61 and 62.

In a similar fashion, the article by Dodt et al. entitled "Distinct binding sites of Ala$^{48}$-Hirudin$^{1-47}$ and Ala$^{48}$-Hirudin$^{48-65}$ on α-thrombin", (1990), The Journal of Biological Chemistry, Vol. 265, No. 2, pp. 713–718, describes experiments aimed at conducting site-directed mutagenesis of hirudin at position 48 in the sequence. The work done by Dodt et al. in this case seems to have been restricted to the substitution of alanine for proline at this position in order to facilitate the required proteolysis necessary for their experiment.

Finally, Maraganore et al., in "Anticoagulant activity of synthetic hirudin peptides", (1989), The Journal of Biological Chemistry, Vol. 264, No. 15, pages 8692–8698, Dennis et al. in "Use of fragments of hirudin to investigate thrombin-hirudin interaction", (1990), Eur. J. Biochem. 188, pages 61–66 and Chang et al. in "The structural elements of hirudin which bind to the fibrinogen recognition site of thrombin are exclusively located within its acidic C-terminal tail", (1990), Febs., Vol. 261, No. 2, pages 287–290, describe the synthesis and anticoagulant properties of a number of peptides whose sequences are based on the sequence of various fragments of native hirudin.

Compounds having anticoagulating properties are valuable therapeutics which may be used in vivo in the treatment of various pathologic states. Among the most important conditions in which an anticoagulant treatment may be useful, there may be mentioned myocardial infarction, pulmonary embolism and cerebral vascular diseases, deep vein thrombosis and other indications of thrombotic disorders.

Currently available anticoagulants are in many respects unsatisfactory. For example, heparin has been employed to inhibit the activity of thrombin and therefore in the treatment of conditions such as venous thrombosis and thrombo embolism. However, heparin exhibits a wide array of undesirable side effects that demonstrate the need for anticoagulants presenting more favorable toxicity levels.

The design of low molecular weight and specific inhibitors of thrombin that utilize accessory binding loci remote from or in conjunction with the catalytic center, similar to the way fibrinogen or hirudin binds to thrombin, constitutes a challenge in protein chemistry. Conceivably, such a multifunctional inhibitor integrates two or more recognitive elements, separated by a suitable spacer, that favor multiple simultaneous interactions and which could manifest enhanced potency and specificity. Incorporation of "foreign" chemical elements embodied in a structure of low molecular weight could confer resistance against proteolysis and favourable bioavailability. Also, because they are smaller than hirudin, these compounds are less likely to stimulate an undesirable immune response in patients treated with them.

PCT application WO 91/02750 indicates that certain thrombin inhibitors possess catalytic site directed moieties that may be cleaved slowly or not cleaved at all. However, all they disclose are modified bonds between the Arg and Gly or Pro such as Arg[psi CH$_2$—NH]-Gly; β-HomoArg-Gly; β-HomoArg-Pro; β-HomoArg-Val; or Arg-[ψCO—CH$_2$]—CH$_2$—(CONH)-Gly. There is no indication that the Gly or Pro amino acid may be completely eliminated and followed by a synthetic linker that is completely resistant to thrombin cleavage.

SUMMARY OF THE INVENTION

The present invention therefore relates to peptides useful as thrombin inhibitors.

It has been found that the native fragment of hirudin comprising residues 45–65 can interact concurrently with two independent and remote sites on thrombin, one site being the putative anion exosite while the other is the catalytic site responsible for proteolysis. This binding mode simulates but is different from the mechanism of the native hirudin molecule which has now been shown to interact with thrombin's active site through its N-terminal three residues. Thus, it appears that residues 45, 46 and 47 do not serve a binding role in the native protein but, in the absence of the N-terminal core, are spatially correctly predisposed to interact, albeit weakly.

Based on this observation, we have synthesized novel peptides that bear modifications in both inhibitory components of the molecule and which exhibit anti-thrombin activity beyond the level of either portion alone. Furthermore, chemical modification of the newly formed scissile bond affords more active compounds that have the advantage of being proteolytically stable to thrombin. The peptides are useful as anticoagulants and as inhibitors of platelet aggregation, thereby decreasing the risk factor in indications of arterial thrombosis and other related cardiovascular disorders. The compounds of the invention may also be used in the treatment of tumor metastasis, such as in the case of carcinomas.

The compounds of this invention may also be employed in compositions and methods for in vivo diagnostic imaging, for storing extracorporeal blood in vitro and coating invasive devices, and for ex vivo treatment of blood.

Hence, the anticoagulant properties of hirudin$^{45-65}$ have been found to be substantially enhanced by modifying the N-terminal catalytic portion of N-acetyl-hirudin$^{45-65}$ to include a bulky hydrophobic portion preferably comprising at least one amino acid of D configuration, by incorporating a non-proteogenic pseudodipeptide, preferably an isostere of arginylglycine in position 47–48, and by at least maintaining the hydrophilic character of amino acids 55 to 60 of native hirudin at the C-terminal non-catalytic portion of N-acetyl-hirudin$^{45-65}$.

The compounds of the present invention therefore comprise peptides that correspond to but are not limited by the carboxyl domain of hirudin comprising residues 45–65.

We have found that shorter peptides, for example, "truncated" peptides lacking amino acids Glu$^{61}$, Glu$^{62}$, Tyr$^{63}$ and Gln$^{65}$ of native hirudin present interesting biological properties. Hence, the "truncated" peptides exhibit better bioavailability as shorter molecules are less likely to cause immune reactions and are less likely to undergo proteolysis. Also, administration of shorter peptides having lower molecular weights is facilitated and absorption is usually better than for longer peptides. It should also be noted that the use of a synthetic linker further prevents degradation of the peptides through proteolysis.

In accordance with the present invention, thrombin inhibitors composed of two portions, a bulky hydrophobic portion and a highly acidic portion linked together by a suitable linker, are provided. In its broadest aspect, the invention relates to peptide derivatives represented by formula (I), or a therapeutically active salt thereof:

AS—Y—Z—A                                          (I)

wherein
AS corresponds to amino acids 45 to 47 of active site directed moiety of hirudin or analogs thereof and wherein the C-terminal carbonyl group is not present;
Y is CO, —CH$_2$—, or —CHOH in the D or L-configuration;
Z is a divalent straight chained link moiety that has a chain length of at least about 10 atoms; and
A is an acidic portion at least maintaining the hydrophobic and acidic character of amino acids 55 to 60 of native hirudin at the C-terminal non-catalytic region of N-acetyl hirudin$^{45-65}$.

For convenience, the peptide derivatives of this invention are designated hereinafter simply as peptides.

The term "residue", when applied to an α-amino acid, means a radical derived from the corresponding α-amino acid by removing the hydroxyl of the carboxyl group and one hydrogen from the α-amino group.

The term "amino acid" used herein includes naturally-occurring amino acids as well as non natural analogs as those commonly used by those skilled in the art of chemical synthesis and peptide chemistry. A list of non natural amino acids may be found in "The Peptides", vol. 5, 1983, Academic Press, Chapter 6 by D. C. Roberts and F. Vellaccio which is incorporated herein by reference.

The term "proteogenic or non-proteogenic α-amino acid" as used in the present application is meant to include those amino acids commonly used by those skilled in the art of peptide chemistry and includes, but is not limited to, naturally occurring α-amino acids. The naturally occurring amino acids are: Glycine (Gly), Alanine (Ala), Valine (Val), Leucine (Leu), Isoleucine (Ile), Serine (Ser), Methionine (Met), Threonine (Thr), Phenylalanine (Phe), Tyrosine (Tyr), Tryptophan (Trp), Cysteine (Cys), Proline (Pro), Histidine (His), Aspartic acid (Asp), Glutamic acid (Glu), Aspargine (Asn), Glutamine (Gln), Arginine (Arg), Ornithine (Orn) and Lysine (Lys).

By a hydrophobic amino acid is usually meant an amino acid that bears an alkyl or aryl group attached to the α-carbon atom. Thus glycine, which has no such group attached to the α-carbon atom, is not a hydrophobic amino acid. The alkyl or aryl groups impart hydrophobic character to the amino acid. The alkyl or aryl group can be substituted, provided that the substituent or substituents present do not detract from the overall hydrophobic character of the acid. Water-solubilizing substituents such as OH, COOH and NH$_2$ are preferably to be avoided. Examples of hydrophobic amino acids include natural amino acid residues such as alanine, histidine, isoleucine, leucine, phenylalanine, tryptophan, tyrosine, valine and unnatural amino acids such as those described in "The Peptides", Vol. 5, 1983, Academic Press, Chapter 6 by D. C. Roberts and F. Vellaccio incorporated herein by reference. For example, one may cite β-(2-and 3-thienyl)alanine, β-(2-and 3-furanyl)alanine, β-(2-and 3- and 4-pyridyl)alanine, cyclohexylalanine and SubPhe. SubPhe represents the phenylalanine residue bearing substituents on the aromatic ring. Common substituents used by those skilled in the art of amino acid chemistry are halogens (fluoride, bromide, chloride), electron withdrawing groups (NO$_2$) or lower alkyl or aryl substituents in the 2, 3 or 4 position. It is to be noted that, unless indicated otherwise, the amino acids used in the context of the present invention are those in the L-configuration.

The term "alkyl" as used herein means alkyl radicals having preferably from 1 to 6 carbon atoms and includes for example: methyl, ethyl, propyl, butyl. Except when otherwise indicated, alkyl groups containing 3 or more carbon atoms can be branched or straight.

IN THE DRAWINGS

FIG. 2 represents the inhibition of thrombin-activated platelet aggregation by peptide P79.

FIG. 5 represents activated partial thromboplastin time for BCH1710 at three dose ranges.

FIG. 6 represents the platelet deposition on pig carotid artery following bilateral angioplasty in the presence of BCH1710.

Figure 1A:
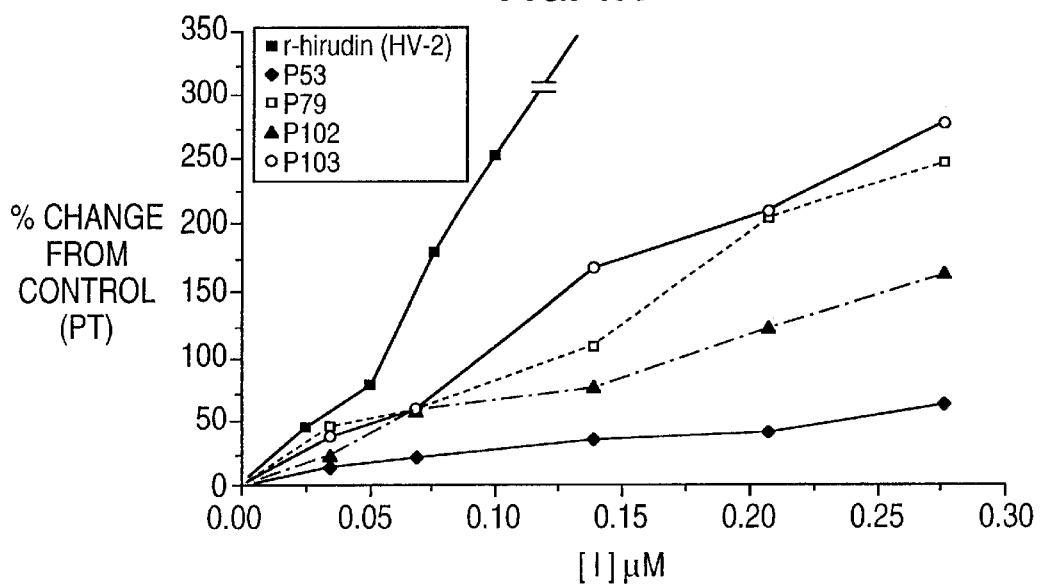
FIG. 1 represents activated partial thromboplastin time and prothrombin time inhibition curves of normal human plasma for peptides P53, P79, P102, P103 and r-hirudin (HV-2).

The present invention will be more readily illustrated by referring to the following description.

DETAILED DESCRIPTION OF THE INVENTION

Preferred compounds of the present invention include those compounds represented by formula (I) wherein Y is carbonyl. Preferred compounds of the present invention include those compounds of formula (I) where Z is a divalent linker moiety composed of a carbon chain that is interrupted by one or more O, S, or NH, and can be substituted by one or more substituents selected from the group consisting of alkyl, alkoxy, alkoxyalkyl, aryl, and aralkyl groups that can in turn be substituted by amide, hydroxy, imidazol, carboxy, or halogen groups. The terminal atom of the chain is a carbon atom that is part of a carbonyl group forming a peptide linkage with said acidic portion A. Z links to Y through a non-peptide bond.

The linker Z to be used in the context of the present invention is required to have sufficient length to permit the peptides of formula I to interact with two different and independent binding sites separated by a critical distance (approximately 15 Å) from each other on the thrombin surface. Preferably, Z is a divalent straight chained linker moiety having a chain length of at least about 10 atoms with the proviso that the initial atom of the chain is not a nitrogen atom forming a peptide linkage with Y.

In some embodiments, Z may be composed, at least in part, of α-amino acids linked by normal peptide linkages, and can be, in part, the amino acids 49 to 54 of native hirudin.

Preferably Z is represented by the formula (II):

—(CH$_2$)$_n$—(CO)$_m$—E,                        (II)

wherein m is 0 or 1.

n is an integer ranging from 0 to 4.

E is a carbon chain that can be interrupted by one or more O, S, NH, that can be substituted by one or more substituents selected from alkyl, alkoxy, alkoxyalkyl, aryl, and aralkyl groups that can in turn be substituted by amide, hydroxy, imidazol, carboxy, or halogen groups. The terminal atom of the chain is a carbon atom that is part of a carbonyl group that forms a peptide linkage with said acidic portion A.

Preferably E is native hirudin[49-54] or analogues thereof. By analogues thereof is meant the native hirudin sequence wherein one or more of the amino acid sequence has been replaced by a conservative substitution. More preferably, E is -Gln-Ser-His-Asn-Asp-Gly-, -Gly-Ser-His-Asn-Asp-Gly-, -[5-aminovaleryl]$_{1-2}$, and (Gly)$_4$.

Also preferably, E can be a synthetic spanner of the general formula (III):

(III)

wherein m is an integer ranging from 1 to 4.

L is a hexapeptide, or saturated or unsaturated alkyl chain corresponding to 18 atoms or less.

More preferably L is —(CH$_{0-2}$)$_{1-4}$—.

Even more preferably L is —(CH$_{0-2}$)$_4$—.

Even further preferably L is —CH$_2$—CH=CH—CH$_2$—.

A preferred L is also —CH$_2$—CH$_2$—CH$_2$—CH$_2$—.

Even more preferably Z is (CH$_2$)$_{2-4}$(CO)-Gln-Ser-His-Asn-Asp-Gly-.

Even further preferably Z is (CH$_2$)$_2$(CO)-Gln-Ser-His-Asn-Asp-Gly-. Even further preferably Z is (CH$_2$)$_3$(CO)-Gln-Ser-His-Asn-Asp-Gly-. Even further preferably Z is (CH$_2$)$_4$(CO)-Gln-Ser-His-Asn-Asp-Gly-.

Even further preferably Z is (CH$_2$)$_4$CO—[NH—CH$_2$—CH=CH—CH$_2$—CO]$_{1-3}$. Further preferably Z is (CH$_2$)$_4$CO—[NH—CH$_2$—CH=CH—CH$_2$— CO]$_1$. Further preferably Z is (CH$_2$)$_4$CO—[NH—CH$_2$—CH=CH—CH$_2$—CO]$_2$. Further preferably Z is (CH$_2$)$_4$CO—[NH—CH$_2$—CH=CH—CH$_2$—CO]$_3$.

E can also be a carbon chain that can be interrupted by one or more O, S, or NH, and can be substituted by one or more substituents selected from the group consisting of alkyl, alkoxy, alkoxyalkyl, aryl, and aralkyl groups that can in turn be substituted by amide, hydroxy, imidazol, carboxy, or halogen groups wherein said alkyl, alkoxy, and alkoxyalkyl groups can join the carbon chain at two points to form an aromatic or non-aromatic ring within the carbon chain.

Further preferably E is pyridylacetyl-R$^{15}$ wherein R$^{15}$ is 1–4 amino acids.

More preferably E is 4-pyridylacetyl-(R$^{20}$)$_{0-1}$-R$^{30}$. R$^{20}$, if present, is NH(CH$_2$)$_n$CO where n is 1–6 and R$^{30}$ is (Gly)$_{1-4}$. Included within this definition of R$^{20}$ is, for example, the non natural amino acids Abu, Ava, Aca, and Aha.

Even more preferably R$^{20}$ is not present, and R$^{30}$ is (Gly)$_{2-4}$.

Preferred compounds of formula (I) include those compounds where the AS portion is a bulky hydrophobic portion comprising a hydrophobic radical which can bind to a complementary hydrophobic region at the catalytic site of thrombin responsible for proteolysis.

Preferably AS is also represented by the formula (IV):

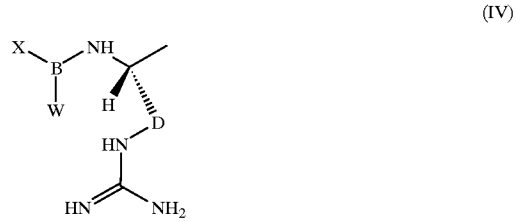
(IV)

wherein

X is a hydrophobic group.

B is a residue of a hydrophobic amino acid.

W is H or a branched or straight chained alkyl, aryl, or aralkyl radical.

D is phenylmethyl, phenylethyl, or a linear carbon chain having 2 to 4 carbon atoms which can be substituted by lower alkyl.

Other preferred compounds include those where X is a hydrophobic α-amino acid in the D-configuration, optionally where the α-amino group is neutralized by acetylation or benzoylation, attached by a peptide linkage to B.

Preferably X is D-Phe, D-4FPhe, or D-4ClPhe wherein the α-amino group is neutralized by acetylation or benzoylation. Further preferably X is D-Phe wherein the α-amino group is neutralized by acetylation or benzoylation.

Other preferred compounds include those where X is a hydrophobic α-amino acid in the D-configuration, attached by a peptide linkage to B.

Preferably X is D-Phe, D-4FPhe, or D-4ClPhe.

Further preferably X is D-Phe.

Preferably B is a residue of a hydrophobic α-amino acid of the L-configuration or a cyclic imino acid which can bear one or more alkyl substituents attached to the ring, wherein said substituents may bridge to form a cyclic structure.

Further preferably B is valine, pipecolic acid, or proline. Even further preferably B is proline.

Preferably W is hydrogen or a lower alkyl, aryl, or aralkyl and may be substituted on the 3, 4, or 5 position of the piperidine or pyrrolidine ring of B when B contains a ring.

Further preferably W is hydrogen or a lower alkyl, aryl, or aralkyl substituent and may be substituted on the 3, 4, or 5 position of the ring when B is proline or pipecolic acid.

Important aspects of the —D—NH—(CNH)—NH$_2$ moiety are its length and its basicity. If in the synthesis of a compound of formula I there is used L-arginine, there will be obtained a compound of formula I of the required stereochemistry in which D is 1,3-propylene. If L-homoarginine is used, there will be obtained a compound in which D is 1,4-butylene. If L-norarginine is used, there will be obtained a compound in which D is 1,2-ethylene. If 4-guanidyl-L-phenylalanine is used, there will be obtained a compound in which D is a p-phenylmethyl group. If 4-guanidyl-L-homophenylalanine is used, there will be obtained a compound in which D is a p-phenylethyl group.

Preferably D is phenylmethyl, phenylethyl, ethylene, butylene, or propylene.

Further preferably D is propylene or phenylmethyl.

Further preferably D is propylene.

Preferred compounds of formula (I) include those wherein A is represented by the formula (V):

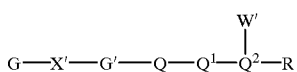
(V)

wherein
G and G' are independently L-α-amino acid having a pk value of about 5 or below.
X' is a L-α-amino acid.
Q is a residue of a L-α-amino acid or a cyclic L-imino acid.
$Q^1$ and $Q^2$ are different and are selected from Ile or Pro;
W' is hydrogen, or a branched or straight chained alkyl, aryl, or aralkyl radical with the proviso that W' is linked to either $Q^1$ or $Q^2$ and is linked to proline.
R is a hydrophobic group comprising 1 to 5 amino acids or an alkyl, aryl, or aralkyl radical which can be substituted by a carboxyl or amide function.

One of G, G', X', and Q may not be present with the proviso that A is at least 6 amino acids in length.

Preferably, G, G', X', and Q are present and are as defined above, $Q^1$ is Ile, and $Q^2$ is Pro.

Preferably G and G' are independently Asp, Glu,

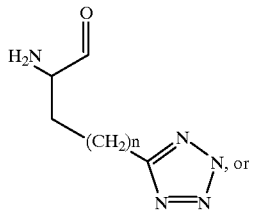

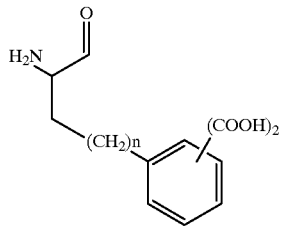

wherein n is 0 or 2.

Further preferably G and G' are independently Asp, Glu, or Phe.

Even further preferably G is Asp. Even further preferably G' is Glu.

Preferably X' is L-Phe, L-4FPhe, or L-4ClPhe, Phe, Glu, or Tyr.

Further preferably X' is L-Phe, L-4FPhe, or L-4ClPhe.

Even further preferably X' is Phe.

Preferably Q is proline, pipecolic acid, sarcosine, or glutamic acid.

Further preferably Q is proline, pipecolic acid, or Glu.

Even further preferably Q is proline, or Q is Glu.

Preferably W' is hydrogen or a lower alkyl, aryl, or aralkyl substituent and may be substituted on the 3, 4, or 5 position of the pyrrolidine ring of $Q^1$ or $Q^2$.

Further preferably W' is hdyrogen or a branched or straight chained lower alkyl.

Even further preferably W' is hydrogen, n-butyl, or methyl.

Preferably R is Leu-R', Glu-Glu-Ala-R', or

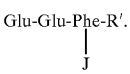

Preferably R' is hydroxyl radical of the COOH terminus of the preceding amino acid, a group comprising 1 to 2 amino acid, or an amine group having the following formula:

wherein $R_2$ and $R_3$ are each independently hydrogen, lower alkyl, aryl, or alkoxyalkyl. $R_2$ and $R_3$ may also be joined to form a ring of 5–6 members, which ring can optionally contain an additional heteroatom selected from O, S, and NH, or pharmaceutically acceptable salts thereof.

Even further preferably R is Leu-R',

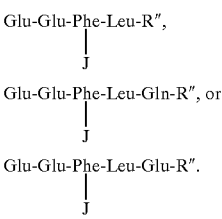

Even further preferably R' and R" are hydroxyl radical of the COOH terminus of the preceding amino acid, any amino acid, or an amine group having the following formula:

wherein $R_2$ and $R_3$ are each independently hydrogen, lower alkyl, aryl, or alkoxyalkyl, or $R_2$ and $R_3$ may be joined to form a ring of 5–6 members, which ring can optionally contain an additional heteroatom selected from O, S, and NH, or pharmaceutically acceptable salts thereof.

More preferably R is Leu-R' or

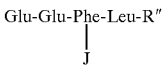

More preferably R' and R" are hydroxyl group radical of the COOH terminus of the preceding amino acid, any amino acid, or an amine group.

Even more preferably R is Glu-Glu-Tyr-Leu-Gln-OH, Leu-OH, or Glu-Glu-Tyr-Leu-OH.

Most preferably R is Glu-Glu-Tyr-Leu-Gln-OH, or Leu-OH.

Preferably J is H, or OH substituted at the para position of the phenyl ring.

Preferred compounds of formula (I) may also be expressed as:

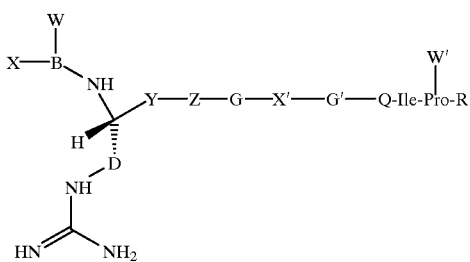

(VI)

wherein

X is a hydrophobic group.

B is a residue of a hydrophobic amino acid.

D is a linear carbon chain having 2 to 4 carbon atoms which can be substituted by lower alkyl, or D is a p-phenylmethyl or a p-phenylethyl group.

Y is carbonyl, hydroxymethyl of either D or L configuration or —CH$_2$—.

Z is a divalent straight chained link moiety having a chain length of at least about 10 atoms. In the case where Y is carbonyl or hydroxymethyl, the atom adjacent to the carbon atom of Y may be unsubstituted or mono- or di-fluoro-substituted. Z can be composed of a carbon chain that is interrupted by one or more O, S, NH, carbonyl, ester, or amide groups and can be substituted by one or more substituents selected from alkyl, alkoxy, alkoxyalkyl, aryl, and aralkyl groups that can in turn be substituted by amide, hydroxy, imidazol, carboxy or halogen groups. The terminal atom of the chain is a carbon atom that is part of a carbonyl group that forms a peptide linkage with the L-α-amino acid G.

G and G' are the same or different and are an L-α-amino acid having a pk value of about 5 or below.

X' is a hydrophobic L-α-amino acid.

Q is a residue of a L-α-amino acid or a cyclic L-imino acid.

W is H, or a branched or straight chain alkyl, aryl, or aralkyl radical.

R is a hydrophobic group comprising 1 to 5 amino acids or an alkyl, aryl, or aralkyl radical which can be substituted by a carboxyl or amide function.

R is

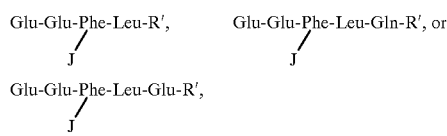

wherein J is H, OH,

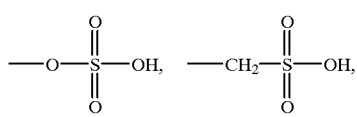

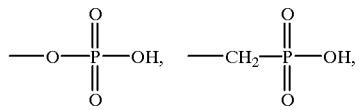

substituted at the para position of the phenyl ring.

R and R' are the same or different and are an amino acid or an amine group having the following formula:

wherein R$_2$ and R$_3$ are each independently hydrogen, lower alkyl, aryl or alkoxyalkyl, and may be joined to form a ring of 5–6 members, which ring can optionally contain an additional heteroatom selected from O, S, and NH, and pharmaceutically acceptable salts thereof.

R' may also be a hydroxyl group attached to Leu to form a carboxyl group, or a therapeutically acceptable salt thereof.

Further preferred compounds are those wherein

X is a hydrophobic α-amino acid in the D-configuration, attached by a peptide linkage to substituent B or a hydrophobic group attached to the nitrogen atom of substituent B.

B is a residue of a hydrophobic α-amino acid of the L-configuration or a cyclic imino acid, which can bear one or more alkyl substituents attached to the ring, which substituents may bridge to form a cyclic structure.

D is p-phenylmethyl, p-phenylethyl, ethylene, butylene, or propylene.

Y is carbonyl.

Z has a chain length ranging between 12 and 40 and preferably 20 atoms.

G and G' are the same or different and are Asp, Glu,

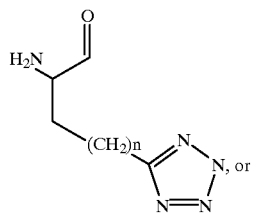

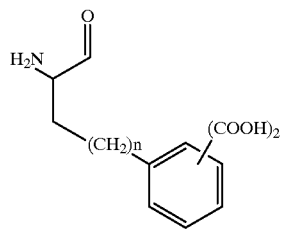

wherein n is 1 or 2.

X' is L-Phe, L-4FPhe or L-4ClPhe.

Q is proline, pipecolic acid, sarcosine or Glu.

W is H or a lower alkyl, aryl or aralkyl substituent on the 3, 4 or 5 position of the piperidine or pyrrolidine ring.

R is

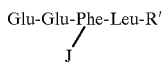

J is H, OH,

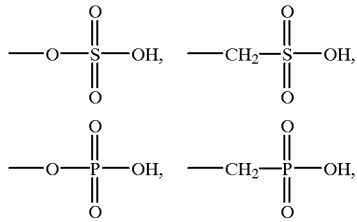

substituted in the para position.

R' is a hydroxyl group or

wherein $R_2$ and $R_3$ are straight chain or branched alkyl chains having 1 to 6 carbon atoms and may be joined to form a ring of 5–6 members.

Even further preferred compounds are those wherein

X is D-Phe, D-4FPhe or D-4ClPhe.

B is Val, pipecolic acid or Pro.

W is hydrogen or a lower alkyl, aryl or aralkyl substituent on the 3,4 or 5 position.

D is propylene of the ring when B is Pro or pipecolic acid or phenylmethyl.

Y is carbonyl.

Z is

wherein n is an integer ranging from 1 to 4, the native hirudin48–54 sequence, or a synthetic spanner of the general formula

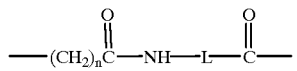

wherein n is an integer ranging from 1 to 4.

L is a hexapeptide or saturated or unsaturated alkyl chain corresponding to 18 atoms or less of a hexapeptide.

R is Glu-Glu-Tyr-Leu-Gln-OH, Leu-OH or Glu-Glu-Tyr-Leu-R' wherein R' is a hydroxyl group or a group having the following formula:

wherein $R_2$ is —$CH_3$ or phenylethyl, $R_3$ is H or —$CH_3$ or $R_2$ and $R_3$ may be joined together to form —$CH_2$—$CH_2$—$CH_2$—$CH_2$—, —$CH_2$—$CH_2$—$CH_2$—$CH_2$—$CH_2$— or —$CH_2$—$CH_2$—O—$CH_2$—$CH_2$—.

Alternatively, a preferred group of compounds of formula I include those listed below where Y is (CO) and is included within the "Arg" designation. The compounds incorporate a peptidomimetic bond ψ($COCH_2$) connecting the Arg of the active site portion with the linker portion. The $P_1$–$P_1'$ bond is represented in italics:

P79 (SEQ ID NO:1) (BCH-1709): Ac(D-Phe)-Pro-Arg-$(CH_2)_2$(CO)-QSHNDGDFEEIPEEYLQ-OH;

P102 (SEQ ID NO:2): Ac(D-Phe)-Pro-Arg-$(CH_2)_3$(CO)-QSHNDGDFEEIPEEYLQ-OH;

P103 (SEQ ID NO:3): Ac(D-Phe)-Pro-Arg-$(CH_2)_4$(CO)-QSHNDGDFEEIPEEYLQ-OH;

P109 (SEQ ID NO:4) (BCH-1711): Ac(D-Phe)-Pro-Arg-$CH_2$(CO)-GSHNDGDFEEIPEEYLQ-OH;

P183 (SEQ ID NO:5): Ac(D-Phe)-Pro-Arg-$(CH_2)_4$(CO)—[NH—$CH_2$—CH=CH—$CH_2$—(CO)]-DFEPIPL-OH;

P184 (SEQ ID NO:6) (BCH-1710): Ac(D-Phe)-Pro-Arg-$(CH_2)_4$(CO)—[NH—$CH_2$—CH=CH—$CH_2$—(CO)]$_2$-DFEPIPL-OH;

P185 (SEQ ID NO:7): Ac(D-Phe)-Pro-Arg-$(CH_2)_4$(CO)—[NH—$CH_2$—CH=CH—$CH_2$—(CO)]$_3$-DFEPIPL-OH;

P290 (SEQ ID NO:8) (BCH-1719) Ac(D-Phe)-thioPro-Arg-$(CH_2)_2$(CO)-QSHNDGDFEEIPEEYLQ-OH;

P311 (SEQ ID NO:9) (BCH-1721): Ac(D-Cha)-Pro-Arg-$(CH_2)_2$(CO)-QSHNDGDFEEIPEEYLQ-OH;

P314 (SEQ ID NO:10) (BCH-1726): Ac(D-Cha)-Pro-Arg-$(CH_2)_2$(CO)-QSHNDGDFEPIPEEY-(Cha)-Q-OH;

P536 (SEQ ID NO:11): (D-Cha)-Pro-Arg-$CH_2$N($COCH_3$) $CH_2$(CO)-$(Gly)_4$-DYEPIPEEY-(Cha)-D-OH;

P574 (SEQ ID NO:12): (D-Phe)-Pro-Arg-$CH_2$-(4-pyridylacetyl)-$(Gly)_4$-DFEEIPEEYLQ-OH;

P596 (SEQ ID NO:13) (BCH-2773): (D-Cha)-Pro-Arg-$CH_2$-(4-pyridylacetyl)-$(Gly)_4$-DYEPIPEEACha-(D)Glu-OH;

P597 (SEQ ID NO:14): (D-Cha)-Pro-Arg-$CH_2$-(4-pyridylacetyl)-$(Gly)_4$-DFEEIPEEYLQ-OH;

P603 (SEQ ID NO:15): (D-Cha)-Pro-Arg-$CH_2$-(4-pyridylacetyl)-Abu-Gly-DYEPIPEEA-(Cha)-(D-Glu)-OH;

P604 (SEQ ID NO:16): (D-Cha)-Pro-Arg-$CH_2$-(4-pyridylacetyl)-Ava-Gly-DYEPIPEEA-(Cha)-(D-Glu)-OH;

P605 (SEQ ID NO:17): (D-Cha)-Pro-Arg-$CH_2$-(4-pyridylacetyl)-Aca-Gly-DYEPIPEEA-(Cha)-(D-Glu)-OH;

P606 (SEQ ID NO:18) (BCH-2774): (D-Cha)-Pro-Arg-$CH_2$-(4-pyridylacetyl)-Aha-Gly-DYEPIPEEA-(Cha)-(D-Glu)-OH;

P609 (SEQ ID NO:19): (D-Cha)-Pro-Arg-$CH_2$-(4-pyridylacetyl)-$(Gly)_4$-DYEPIPEEA-(Cha)-(D-Glu)-OH;

P617 (SEQ ID NO:20) (BCH-2772): H-(D-Phe)-Pro-Arg-$CH_2SCH_2$ (CO)-$(Gly)_4$-DFEEIPEEYLQ-OH;

P618 (SEQ ID NO:21): Ac(D-Phe)-Pro-Arg-$CH_2SCH_2$(CO)-$(Gly)_4$-DFEEIPEEYLQ-OH;

P658 (SEQ ID NO:22): (D-Cha)-Pro-Arg-$CH_2$-(4-pyridylacetyl)-NH$(CH_2)_2$CO-Gly-DYEPIPEEA-(Cha)-(D-Glu)-OH;

P659 (SEQ ID NO:23 ): (D-Cha)-Pro-Arg-$CH_2$-(4-pyridylacetyl)-Gly-Gly-DYEPIPEEA-(Cha)-(D-Glu)-OH;

P660 (SEQ ID NO:24): (D-Cha)-Pro-Arg-$CH_2$-(4-pyridylacetyl)-$NH(CH_2)_3CO$-DYEPIPEEA-(Cha)-(D-Glu)-OH;

P661 (SEQ ID NO:25): (D-Cha)-Pro-Arg-$CH_2$-(4-pyridylacetyl)-$NH(CH_2)_2CO$-DYEPIPEEA-(Cha)-(D-Glu)-OH;

BCH-2408 (SEQ ID NO:26): Ac(D-Phe)-Pro-Arg-$(CH_2)_2$(CO)-QSHNDGDFEPIPEEY-(Cha)-Q-OH;

BCH-2414 (SEQ ID NO:27): Ac(D-Phe)-Pro-Arg-$(CH_2)_4$(CO)-[NH—$CH_2$—CH=CH—$CH_2$—(CO)]$_2$-DEFPIPY-OH;

BCH-2423 (SEQ ID NO:28): succinyl(D-Phe)-Pro-Arg-$(CH_2)_2$(CO)-QSHNDGDFEEIPEEYLQ-OH;

BCH-2739 (SEQ ID NO:29): Ac(D-Phe)-Pro-Arg-$(CH_2)_4$(CO)—[$NH(CH_2)_4(CO)$]$_2$-DFEPIPL-OH;

BCH-2757 (SEQ ID NO:30): alpha-N-(Ac) (D-Phe)-Pro-Arg-$(CH_2)_4$(CO)—[$NH(CH_2)_4(CO)$]-NGDFEPIPL-TFA salt;

BCH-2758 (SEQ ID NO:31): (D-Phe)-Pro-Arg-$(CH_2)_4$(CO)—[$NH(CH_2)_4(CO)$]$_2$-DF-(4-thiahomoGlu)-PIPL-TFA salt;

BCH-2763 (SEQ ID NO:32): (D-Phe)-Pro-Arg-$(CH_2)_4$(CO)—[$NH(CH_2)_4CO$]$_2$-DFEPIPL-TFA salt; and BCH-2767 (SEQ ID NO:33): (D-Phe)-Pro-Arg-$(CH_2)_4$(CO)—[$NH(CH_2)_4CO$]$_2$-FEPIPL-TFA salt.

Alternatively, further preferred compounds of the invention comprise those where Z is a chain interrupted with a sulfur atom or a nitrogen atom:

P536 (SEQ ID NO:11): (D-Cha)-Pro-Arg-$CH_2N$(acetyl)$CH_2$(CO)-(Gly)$_4$-DYEPIPEEY-(Cha)-D-OH;

P617 (SEQ ID NO:20): (BCH-2772): H-(D-Phe)-Pro-Arg-$CH_2SCH_2$(CO)-(Gly)$_4$-DFEEIPEEYLQ-OH; and P618 (SEQ ID NO:21): Ac(D-Phe)-Pro-Arg-$CH_2SCH_2$(CO)-(Gly)$_4$-DFEEIPEEYLQ-OH.

Other preferred compounds of the invention include those wherein Z includes pyridylacetic acid residue:

P574 (SEQ ID NO:12): (D-Phe)-Pro-Arg-$CH_2$-(4-pyridylacetyl)-(Gly)$_4$-DFEEIPEEYLQ-OH;

P596 (SEQ ID NO:13) (BCH-2773): (D-Cha)-Pro-Arg-$CH_2$-(4-pyridylacetyl)-(Gly)$_4$-DYEPIPEEACha-(D)Glu-OH;

P597 (SEQ ID NO:14): (D-Cha)-Pro-Arg-$CH_2$-(4-pyridylacetyl)-(Gly)$_4$-DFEEIPEEYLQ-OH;

P603 (SEQ ID NO:15): (D-Cha)-Pro-Arg-$CH_2$-(4-pyridylacetyl)-Abu-Gly-DYEPIPEEA-(Cha)-(D-Glu)-OH;

P604 (SEQ ID NO:16): (D-Cha)-Pro-Arg-$CH_2$-(4-pyridylacetyl)-Ava-Gly-DYEPIPEEA-(Cha)-(D-Glu)-OH;

P605 (SEQ ID NO:17): (D-Cha)-Pro-Arg-$CH_2$-(4-pyridylacetyl)-Aca-Gly-DYEPIPEEA-(Cha)-(D-Glu)-OH;

P606 (SEQ ID NO:18) (BCH-2774): (D-Cha)-Pro-Arg-$CH_2$-(4-pyridylacetyl)-Aha-Gly-DYEPIPEEA-(Cha)-(D-Glu)-OH;

P609 (SEQ ID NO:19): (D-Cha)-Pro-Arg-$CH_2$-(4-pyridylacetyl)-(Gly)$_4$-DYEPIPEEA-(Cha)-(D-Glu)-OH;

P658 (SEQ ID NO:22): (D-Cha)-Pro-Arg-$CH_2$-(4-pyridylacetyl)-$NH(CH_2)_2CO$-Gly-DYEPIPEEA-(Cha)-(D-Glu)-OH;

P659 (SEQ ID NO:23): (D-Cha)-Pro-Arg-$CH_2$-(4-pyridylacetyl)-Gly-Gly-DYEPIPEEA-(Cha)-(D-Glu)-OH;

P660 (SEQ ID NO:24): (D-Cha)-Pro-Arg-$CH_2$-(4-pyridylacetyl)-$NH(CH_2)_3CO$-DYEPIPEEA-(Cha)-(D-Glu)-OH; and P661 (SEQ ID NO:25): (D-Cha)-Pro-Arg-$CH_2$-(4-pyridylacetyl)-$NH(CH_2)_2CO$-DYEPIPEEA-(Cha)-(D-Glu)-OH.

Other preferred compounds of the invention include those where the linker amino acid portion of native hirudin is partially or completely substituted with a linear chain as indicated in bold:

P183 (SEQ ID NO:5): Ac(D-Phe)-Pro-Arg-$(CH_2)_4$(CO)—[NH—$CH_2$—CH=CH—$CH_2$—(CO)]-DFEPIPL-OH;

P184 (SEQ ID NO:6) (BCH-1710): Ac(D-Phe)-Pro-Arg-$(CH_2)_4$(CO)—[NH—$CH_2$—CH=CH—$CH_2$—(CO)]$_2$-DFEPIPL-OH;

P185 (SEQ ID NO:7): Ac(D-Phe)-Pro-Arg-$(CH_2)_4$(CO)—[NH—$CH_2$—CH=CH—$CH_2$—(CO)]$_3$-DFEPIPL-OH;

BCH-2414 (SEQ ID NO:27): Ac(D-Phe)-Pro-Arg-$(CH_2)_4$(CO)—[NH—$CH_2$—CH=CH—$CH_2$—(CO)]$_2$-DEFPIPY-OH;

BCH-2739 (SEQ ID NO:29): Ac(D-Phe)-Pro-Arg-$(CH_2)$(CO)—[NH—$(CH_2)_4$—(CO)]$_2$-DFEPI-PL-OH;

BCH-2757 (SEQ ID NO:30): alpha-N-(Ac)(D-Phe)-Pro-Arg-$(CH_2)_4$(CO)-[5-aminovaleryl]-NGDFEPIPL-TFA salt;

BCH-2758 (SEQ ID NO:31): (D-Phe)-Pro-Arg-$(CH_2)_4$(CO)-[5-aminovaleryl]$_2$-DF-(4-thiahomoGlu)-PIPL-TFA salt;

BCH-2763 (SEQ ID NO:32): (D-Phe)-Pro-Arg-$(CH_2)_4$(CO)—[$NH(CH_2)_4CO$]$_2$-DFEPIPL-TFA salt; and BCH-2767 (SEQ ID NO:33): (D-Phe)-Pro-Arg-$(CH_2)_4$(CO)-[5-aminovaleryl]$_2$-FEPIPL-TFA salt.

More preferred compounds of the invention are those that have a Ki of about 0.5 nM or lower:

P79 (SEQ ID NO:1) (BCH-1709): Ac(D-Phe)-Pro-Arg-$(CH_2)_2$ (CO)-QSHNDGDFEEIPEEYLQ-OH;

P103 (SEQ ID NO:3): Ac(D-Phe)-Pro-Arg-$(CH_2)_4$(CO)-QSHNDGDFEEIPEEYLQ-OH;

P311 (SEQ ID NO:9) (BCH-1721): Ac(D-Cha)-Pro-Arg-$(CH_2)_2$(CO)-QSHNDGDFEEIPEEYLQ-OH;

P314 (SEQ ID NO:10) (BCH-1726): Ac(D-Cha)-Pro-Arg-$(CH_2)_2$(CO)-QSHNDGDFEPIPEEY-(Cha)-Q-OH;

BCH-2408 (SEQ ID NO:26): Ac(D-Phe)-Pro-Arg-$(CH_2)_2$(CO)-QSHNDGDFEPIPEEY-(Cha)-Q-OH;

BCH-2414 (SEQ ID NO:27): Ac(D-Phe)-Pro-Arg-$(CH_2)_4$(CO)—[NH—$CH_2$—CH=CH—$CH_2$—(CO)]$_2$-DEFPIPY-OH;

BCH-2423 (SEQ ID NO:28): succinyl(D-Phe)-Pro-Arg-$(CH_2)_2$ (CO)-QSHNDGDFEEIPEEYLQ-OH;

BCH-2763 (SEQ ID NO:32): (D-Phe)-Pro-Arg-$(CH_2)_4$(CO)—[$NH(CH_2)_4CO$]$_2$-DFEPIPL-TFA salt;

P596 (SEQ ID NO:13) (BCH-2773): (D-Cha)-Pro-Arg-$CH_2$-(4-pyridylacetyl)-(Gly)$_4$-DYEPIPEEACha-(D)Glu-OH; and P606 (SEQ ID NO:18) (BCH-2774): (D-Cha)-Pro-Arg-$CH_2$-(4-pyridylacetyl)-Aha-Gly-DYEPIPEEA-(Cha)-(D-Glu)-OH.

Further preferred compounds of the invention are those that have a $K_i$ of about 50 pM or lower:

P314 (SEQ ID NO:10) (BCH-1726): Ac(D)Cha-Pro-Arg-$(CH_2)_2$(CO)-QSHNDGDFEPIPEEY-(Cha)-Q-OH;

BCH-2408 (SEQ ID NO:26): Ac(D)Phe-Pro-Arg-$(CH_2)_2$ (CO)-QSHNDGDFEPIPEEY-(Cha)-Q-OH;

BCH-2763 (SEQ ID NO:32): (D)Phe-Pro-Arg-$(CH_2)_4$(CO)—[$NH(CH_2)_4CO$]$_2$-DFEPIPL-TFA salt;

P596 (SEQ ID NO:13) (BCH-2773): (D)Cha-Pro-Arg-$CH_2$-(4-pyridylacetyl)-(Gly)$_4$-DYEPIPEEACha-(D)Glu-OH; and P606 (SEQ ID NO:18) (BCH-2774): (D-Cha)-Pro-Arg-$CH_2$-(4-pyridylacetyl)-Aha-Gly-DYEPIPEEA-(Cha)-(D-Glu)-OH.

Most preferred compound of the invention is BCH-2763 (SEQ ID NO:33): (D)Phe-Pro-Arg-$(CH_2)_4$(CO)—$[NH(CH_2)_4CO]_2$-DFEPIPL-TFA salt.

The present invention also relates to a composition for treating indications of thrombotic disorders. This composition comprises an effective amount of a peptide derivative of formula I in admixture with a pharmaceutically acceptable carrier.

Also within the scope of the present invention is a method for the treatment or prophylaxis of vascular diseases related to thrombosis. The method comprises administering to a patient an effective amount of a composition comprising a peptide derivative of formula I in admixture with a pharmaceutically acceptable carrier.

The invention also relates to a method for decreasing reperfusion time or increasing reocclusion time in a patient treated with a thrombolytic agent. The method comprises administering to a patient an effective amount of a composition comprising a peptide derivative of formula I and a thrombolytic agent in admixture with a pharmaceutically acceptable carrier.

According to another aspect of the present invention, these compounds may be used in the treatment of tumor metastases. The efficacy of the thrombin inhibitors of this invention for the treatment of tumor metastases is manifested by the inhibition of metastatic growth. This is based upon the presence of a procoagulant enzyme in certain cancer cells. This enzyme activates the conversion of Factor X and Factor Xa in the coagulation cascade, resulting in fibrin deposition which, in turn, serves as a substrate for tumor growth. By inhibiting fibrin deposition through inhibition of thrombin, the molecules of the present invention serve as effective anti-metastatic tumor agents. Examples of metastatic tumors which may be treated by the thrombin inhibitors of this invention include, but are not limited to, carcinoma of the brain, carcinoma of the liver, carcinoma of the lung, osteocarcinoma and neoplastic plasma cell carcinoma.

According to an alternate embodiment of this invention, thrombin inhibitors may be used in compositions and methods for coating the surfaces of invasive devices, resulting in a lower risk of clot formation or platelet activation in patients receiving such devices. Surfaces that may be coated with the compositions of this invention include, for example, prostheses, artificial valves, vascular grafts, stents and catheters. Methods and compositions for coating these devices are known to those of skill in the art. These include chemical cross-linking or physical adsorption of the thrombin inhibitor-containing compositions to the surface of the devices.

According to a further embodiment of the present invention, thrombin inhibitors may be used for diagnostic thrombus imaging in a patient. In this embodiment, the thrombin inhibitor is labeled with a radioisotope. The choice of radioisotope is based upon a number of well-known factors, for example, toxicity, biological half-life, and detectability. Preferred isotopes include, but are not limited to, $^{125}I$, $^{123}I$, and $^{111}In$. Techniques for labeling the thrombin inhibitor are well known in the art. Most preferably, the radioisotope is 123I and the labeling is achieved using $^{123}I$-Bolton-Hunter Reagent. The labeled thrombin inhibitor is administered to a patient and allowed to bind to the thrombin contained in a clot. The clot is then observed by utilizing well-known detecting means, such as a camera capable of detecting radioactivity coupled to a computer imaging system. This technique also yields images of platelet-bound thrombin and meizothrombin.

This invention also relates to the use of the above-described thrombin inhibitors, or compositions comprising them, as anticoagulants for ex vivo treatment of blood or extracorporeal (in vitro) blood. As used herein, the term "ex vivo" treatment includes blood removed in line from a patient, subjected to extracorporeal treatment, and then returned to the patient such as dialysis procedures, blood filtration, or blood bypass during surgery. As used herein, the term "extracorporeal blood" refers to blood products that are stored extracorporally for eventual administration to a patient and blood collected from a patient to be used for various assays. Such products include whole blood, plasma, or any blood fraction in which inhibition of coagulation is desired.

Pharmaceutical Compositions

The peptides of the present invention may be obtained in the form of therapeutically acceptable salts. Since the peptides of the present invention have residues that function both as acids and/or bases, then salts of organic acids (e.g. acetic, lactic, succinic or malic) or bases (e.g. sodium, potassium or calcium) could be derived. These salts of the peptides of formula I are fully biologically active. Therapeutically acceptable salts may be converted from one salt form to another by employing a suitable ion exchange resin in a manner described by R. A. Boissonas et al., Helv. Chim. Acta. 43, 1849 (1960).

The peptides of the present invention, or their therapeutically acceptable salts, are employed alone or in combinations for the treatment of prophylaxis of vascular diseases due to thromboses. They are administered systemically to warm blooded animals, e.g. humans, horses, or dogs, with pharmaceutically acceptable carriers, the proportion of composition of which depends on solubility and chosen route of administration. The peptides of the present invention are administered either intravenously, subcutaneously or by intramuscular injection in combination with pharmaceutically acceptable carriers. Examples of suitable carriers are found in standard pharmaceutical texts, e.g. "Remington's Pharmaceutical Sciences", 16th edition, Mack Publishing Company, Easton, Pa., 1980.

The dosage of the peptides will vary depending on the form of administration and particular compound. In the case of an injection, the therapeutically effective dose of peptide is in a dosage range of approximately 0.05 mg/kg to 10 mg/kg body weight. In addition to the active ingredient, the compositions usually also contain suitable buffers, for example phosphate buffer, to maintain an appropriate pH and sodium chloride, glucose or mannitol to make the solution isotonic.

The peptides of the present invention may be administered alone or in combination with other pharmaceuticals. For example, the peptides may be administered in combination with tissue plasminogen activator to prevent reocclusion of coronary arteries. Alternatively, the peptides of the present invention could be administered with heparin or low molecular weight heparin, a combination which could advantageously lower the dosage of heparin or low molecular weight heparin.

Synthesis of the Peptide Derivatives of the Present Invention

The peptides of the present invention may be synthesized using a variety of methods which are well known to those skilled in the art. For example, the peptides may be synthesized by the solid phase method such as that described by Stewart et al. in "Solid phase peptide synthesis", Freeman & Co., San Francisco, 1969 on a suitable peptide synthesizer.

In some instances however, regions (i), (ii), or (iii) of the peptides of the present invention may be a synthetic moiety for which chemical synthesis is required prior to linking this moiety with other amino acids to yield the desired peptide through conventional solid phase synthesis. Examples 1 to 6 appearing further in the specification illustrate the type of chemical synthesis needed to synthesize one of the preferred embodiments in region (i) while example 7, 8, and 9 describe the synthesis of a synthetic linker to be used in region (iii). It will be appreciated by those skilled in the art that a skilled organic chemist can readily prepare the chemical moiety which may be required for regions (i), (ii), and (iii) of the peptides of the present invention.

Some of the peptides of the present invention were specifically synthesized on an Applied Biosystems 430A peptide synthesizer. BOC-GlnPAM resin (Applied Biosystems; 0.64 mmol/gram) was used as the solid phase support. Amino acid coupling was mediated by dicyclohexylcarbodiimide/N-hydroxybenzoltriazole and deprotection was carried out with 50% trifluoroacetic acid (TFA) in methylene chloride for 3 minutes followed by an additional 20 minute cycle. Side chain protecting groups were as follows: Asp(Chx), Glu(Bzl), His(Bom), Arg(Tos), Tyr(2-BrZ), Ser(Bzl). The fully protected peptide resin was then treated with liquid hydrogen fluoride containing anisole and dimethyl sulfide (10% by volume) at −5° C. for 60 minutes. Excess HF was removed under a stream of nitrogen and the residual solid was extracted with ether and filtered. The resin was extracted three times with glacial acetic acid and water followed by lyophilization.

Within the scope of the present invention is a process for the preparation of compounds of formula I comprising the steps of:

a) reacting a compound of formula IIc

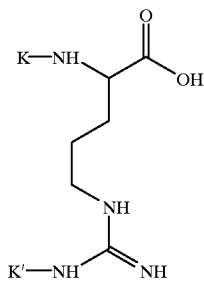

(IIc)

wherein K and K' are the same or different suitable protecting groups such as Boc or Tos,
with a compound of formula HCl N(CH$_3$)OCH$_3$ in the presence of BOP to obtain a compound of formula IIb:

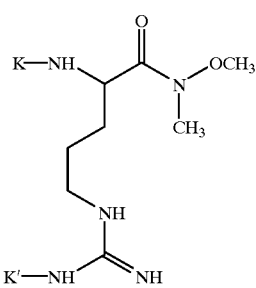

(IIb)

b) reacting the compound of formula IIb with Grignard's reagent MgBr CH$_2$(CH$_2$)$_{n-1}$CH=CH$_2$ to obtain a compound of formula IIa:

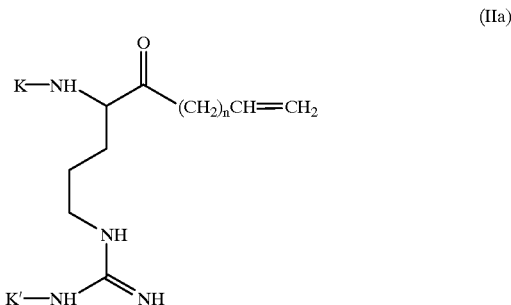

(IIa)

wherein n is an integer from 1 to 4,
and c) oxidizing the compound of formula IIa with an oxidant having the ability to oxidize double bonds to obtain an intermediate of formula II:

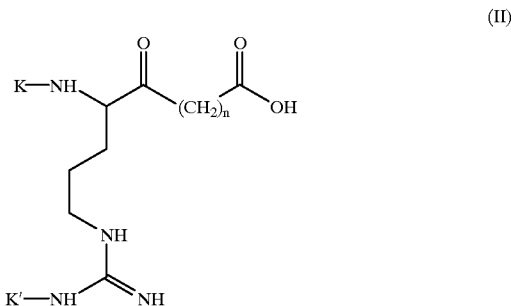

(II)

wherein n, K, and K' are as defined above.
The process further comprises the steps of
d) esterifying a compound of formula IIIb:

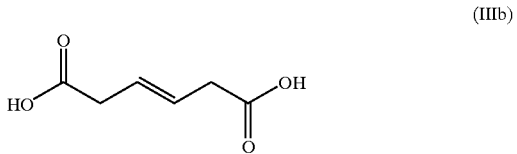

(IIIb)

to obtain a compound of formula IIIa:

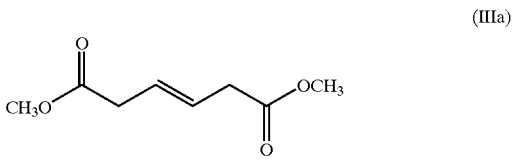

(IIIa)

and e) treating the compound of formula IIIa with an enzyme having the ability to effect removal of one methyl group, such as pig liver esterase, to recover an intermediate of formula III:

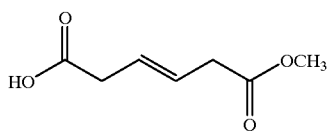

(III)

Finally, the process further comprises the steps of:

f) modifying the compound of formula III to obtain a compound of formula IV:

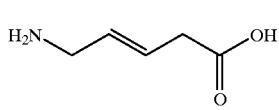

(IV)

and g) coupling the compound of formula IV with the compound of formula II to obtain compounds of formula Ia:

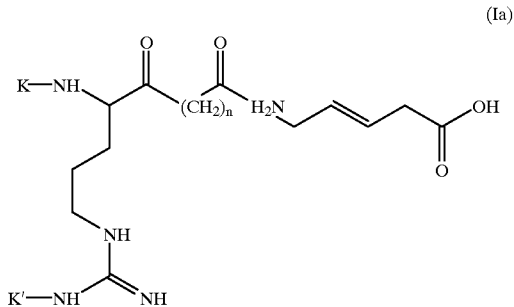

(Ia)

and then deprotecting the protected groups to obtain compounds of formula (I).

Purification and Analysis of the Synthetic Peptides

The resulting lyophilized crude peptides may be purified to homogeneity by using generally accepted peptide purification techniques. One suitable technique is reverse phase chromatography on a Vydac octadecyl silica glass column (15 Å, 1.5×30 cm, 40 psi) using a linear gradient of the solvent system: A, 500 ml 500 ml 0.1% TFA/H2O and B, 1 L 60% Acetonitrite/H2O containing 0.1% TFA. The fractions are analyzed by reverse phase HPLC on a Varian LC using a Vydac C18 analytical column and 215 nm detection. Fractions corresponding to greater than 99% purity may be pooled and lyophilized. Peptide content is determined by amino acid analysis on a Beckman model 6300 amino acid analyzer. Samples are then dried in a Waters Pico-Tag Work Station. Constant boiling HCl (200 μl) containing 1% phenol was added to the vial and alternatively purged (with dry nitrogen) and evacuated after three purges. Finally, the vial containing the sample is heated at 150° C. for 1 hour under vacuum. Mass spectral analyses were carried out on a SCIEX® API III spectrometer equipped with an ionspray inlet source.

Thus, the structure and sequence of the peptides synthesized in the context of the present invention may be confirmed by correct amino acid composition and mass spectra in order to show agreement with the calculated molecular weights.

The following examples are provided to further illustrate rather than limit the scope of the present invention.

Abbreviations used in the examples include BOC: tert-butoxycarbonyl; Tos: p-toluene sulfonyl; $CH_2Cl_2$: methylene chloride; TEA: triethylamine; BOP: benzotriazolyl N-oxytrisdimethylamino phosphonium hexafluorophosphate; DMF: dimethyl formamide; EtOAc: ethyl acetate; DCC: N,N'-dicyclohexylcarbodiimide; DPPA: diphenylphosphoryl azide; THF: tetrahydrofuran; HF: hydrogen fluoride, CBZ: benzyloxycarbonyl.

EXAMPLE 1

Synthesis of (2S)-2-(BOC)-N-methoxy-N-methyl-5-tosylguanadinopentanamide

To a solution of Nα-BOC-NG-Tosyl Arginine (428 mg, 1 mmol) in 30 ml of DMF, at 0° C. in an ice bath, containing TEA (0.4 ml, 3 mmol) and N,O-dimethylhydroxyl-amine hydrochloride (146 mg, 1.5 mmol) was added BOP reagent (500 mg, 1.1 mmol) (B. Castro, J. R. Dormoy, G. Elvin, C. Selve, Tetrahedron Letters # 14, pp. 1219–1222, 1975). The reaction was stirred for 15 hours at 4° C. after which the solvent was evaporated under high vacuum. The residue was dissolved in 50 ml of EtOAc and washed with $H_2O$. The organic phase was extracted further with 5% $NaHCO_3$ (3 times), 1N HCl (3 times) and dried over $Na_2SO_4$. The solvent was filtered over celite and concentrated in vacuo. Addition of a small amount of hexane to the concentrate deposited a white solid (500 mg) corresponding to the title compound. Mass spectral analysis: M/Z=472 (M+H)+.

EXAMPLE 2

Synthesis of 6-BOC-9-tosylguanidino-1-nonen-5-one

To a solution of the product from example 1 (600 mg, 1.3 mmol) in 25 ml of THF was added 10 equivalents of the Grignard reagent prepared from 4-bromo-1-butene (Note on preparation: 312 mg of Magnesium turnings (13 mmol) in 50 ml of anhydrous ether was treated with 1.75 g of 4-bromo-1-butene dropwise to maintain a gentle reflux) after total consumption of the metal the Grignard solution was transferred by syringe under argon to the THF mixture. The entire THF mixture was quenched with aqueous $NH_4Cl$ after TLC showed disappearance of starting material (TLC was performed on Kieselgel® 60F 254, Merck, glass plates). The phases were separated and the organic phase was washed further with 1N HCl and $H_2O$, dried ($Na_2SO_4$) and evaporated under vacuum. Chromatography on silica gel (eluting with 4:1 EtOAc/hexane afforded a clear oil corresponding to the title compound. Mass spectral analysis M/Z=469 (M+H)+.

EXAMPLE 3

Synthesis of 5-BOC-4-oxo-8-tosylguanidinooctanoic acid

The product from example 2 (2.5 g, 5.3 mmol) was dissolved in 50 ml of acetonitrile followed by addition of sodium periodate (8 g, 37.5 mmol) dissolved in 50 ml of water. The whole mixture was treated with 100 mg of ruthenium chloride. After one hour vigorous stirring at room temperature, no starting material was observed by TLC. The mixture was diluted with 100 ml of $H_2O$ and 100 ml of ether. The phases were separated and the aqueous phase was extracted further with ether. The combined organic extracts were washed with $H_2O$, dried (($Na_2SO_4$) and evaporated to dryness affording 1.5 g of a foam corresponding to the title compound. M/Z=485 (M+H)+.

EXAMPLE 4

Synthesis of 6-BOC-5-oxo-9-tosylguanidinononanoic acid

The title compound of this example was synthesized in a manner analogous to examples 1 to 3. Briefly the product from example 1 was reacted with a Grignard reagent prepared from Magnesium and 5-bromo-1-pentene. The resulting adduct isolated as an oil analogous to example 3 was subsequently treated with a combination of sodium periodate and ruthenium chloride to afford the title homologue of this example. M/Z=499 (M+H)+.

EXAMPLE 5

Synthesis of 7-BOC-6-oxo-10-tosylguanidinodecanoic acid

The title compound of this example was prepared in a manner analogous to examples 1 to 4. In this example, the product from example 1 was reacted with the Grignard reagent prepared from Magnesium and 6-bromo-1-hexene. Following isolation of the adduct by silica gel chromatography as described in example 2, the adduct was reacted with sodium periodate and ruthenium chloride. Isolation of the product afforded the title compound as an oil. M/Z=513 (M+H)+.

EXAMPLE 6

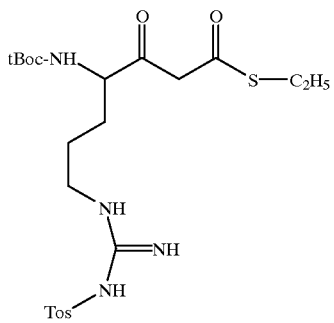

Ethyl; 4N-t-BOC-3-oxo-7-tosylguanidine thioheptanoate (mixed anhydride method)

Formation of mixed anhydride: To a stirring solution of 1 g(2.4 mmol) of (L)-Nα-BOC-Arg(Nw)TOS)OH and 0.66 ml(0.48 mmol) of triethylamine in 15 ml of anhydrous tetrahydrofuran at −20° C. was added 0.40 ml(0.3 mmol) of isobutylchloroformate dropwise over 15 minutes. After 1 hour the mixture was diluted with 15 ml of ether and the precipitated solid was filtered. The filtrate containing the mixed anhydride was stored at 0° C.

Meanwhile, to a stirred solution of diisopropylamine (3.4 ml, 24 mmol) in 25 ml of anhydrous ether under argon at 0° C. was treated with one equivalent of N-But Li in THF dropwise over 30 minutes. After, the reaction mixture was cooled to −60° C. and treated with 2.5 ml of ethyl thioacetate. After stirring at −60° C. for 30 minutes, the mixture was treated with 6 g of $MgBr_2$ etherate and stirred for an additional 30 minutes. Finally, this mixture was treated with the preformed mixed anhydride and stirring was continued for 5 hours until reaction was complete by HPLC.

The reaction mixture was treated dropwise with 6 M $NH_4Cl$ and the phases were separated. The organic phase was diluted with 50 ml of EtOAc and extracted with 1N HCl (3×), $H_2O$ (3×) dried with $Na_2SO_4$ and evaporated under high vacuum affording the title compound as an oil M/Z= 515 (M+H)+.

EXAMPLE 7

Coupling of the thioester from Example 6 to α-amino acid esters and deprotected amino acyl polystyrene resins The protected arginyl statone from example 6 (2 equivalents) was dissolved in $CH_2Cl_2$ and added to a mixture of α-amino acid ester (1 equivalent) or polystyrene resin containing the growing polypeptide chain. To this mixture was added Cuprous Iodide (2 equivalents) and triethyl amine (2 equivalents). The reaction is monitored by HPLC in the case of amino acid ester or by conventional ninhydrin test in the case of polystyrene bound peptides.

EXAMPLE 8

Synthesis of the peptide having the formula:

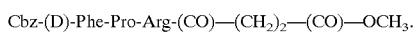

Cbz-(D)-Phe-Pro-Arg-(CO)—$(CH_2)_2$—(CO)—$OCH_3$.

The amino acid from example 3 (200 mg, 0.4 mmol) was dissolved in 10 ml of EtOAc and treated with an ethereal solution of diazomethane until gas evolution ceased. The methyl ester thus formed was isolated by evaporation and deprotected with 10 ml of 50% $TFA/CH_2Cl_2$ at 0° C. for one hour. Evaporation of the solvent under high vacuum afforded 200 mg of a viscous oil that resisted crystallization and was used directly. The obtained oil (200 mg, 0.33 mmol) was dissolved in 20 ml of DMF cooled in an ice bath and treated with 158 mg (0.4 mmol) of Cbz-(D)-Phe-Pro-OH, 0.14 ml (1 mmol) of TEA and 110 mg (0.4 mmol) of DPPA. The whole solution was allowed to stand at 4° C. for 15 hours and evaporated under high vacuum. The residue was partitioned between water and EtOAc and the phases were separated. The organic phase was treated further as described in example 3 and after evaporation of the solvent, a residue was obtained which was purified by silica gel chromatography (150 mg).

The protecting groups were removed by treatment of the peptide with liquid hydrogen fluoride at 0° C. for 1 hour. Following evaporation of excess HF, the residue was dissolved in 50 ml of 10% AcOH and extracted with ether (3 times). The aqueous phase was lyophilized affording a powder corresponding to the title compound of this example. M/Z=489.2 (M+H)+.

EXAMPLE 9

Preparation of the subunit of the synthetic spacer of formula II:

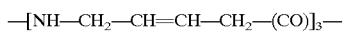

—[NH—$CH_2$—CH=CH—$CH_2$—(CO)]$_3$—

The synthesis was modeled upon Cox M. T., Heston D. W. and Horbury J., J. Chem. Soc. Chem. Comm., 1980, 799–800 with major modifications. The complete process is outlined as follows:

a) Synthesis of trans-B-hydromuconic acid dimethyl ester 22 g (153 mmol) of trans-β-hydromuconic acid was dissolved in 200 ml of benzene containing 500 mg of p-toluene sulfonic acid and 100 ml of methanol. The solution was maintained at reflux for 6 hours and treated with 100 ml of water. The phases were separated and the organic layer was extracted further with 5% $NaHCO_3$ and $H_2O$. After drying ($Na_2SO_4$), the solvent was evaporated under vacuum and the residue was distilled (83–85° C.) 0.5 mm Hg) affording 19 g of the title compound.

b) Synthesis of trans-β-hydromuconic acid monomethyl ester 5 g (27.5) mmol) of the product from step a) was suspended in 100 ml of a solution of 0.1 M $KH_2PO_4$ followed by addition of 20 mg of pig liver esterase. The pH of the solution was maintained at 7 by dropwise addition of a solution of 1 M NaOH. Following the addition of 1 M NaOH corresponding to 1 mole equivalent of the diester, the solution was treated with charcoal, stirred for 5 minutes and filtered over celite. The filtrate was extracted with ether and the combined organic extracts were discarded. The aqueous phase was made acidic with 3 N HCl and reextracted with ether. The combined ethereal extracts were dried ($Na_2SO_4$) and evaporated in vacuo. The residue was distilled under reduced pressure (105–110° C., 0.5 mmHg) leaving 4 g of an oil corresponding to the title compound.

c) Synthesis of 4-methoxycarbonyl-2-dehydro butyl isocyanate 1.22 g (7.3 mmol) of the mono ester from step b) was dissolved in 25 ml of benzene. 0.76 ml (8.7 mmol) of oxalyl chloride was added dropwise over 15 minutes and the solution was stirred vigorously for 3 hours. The solution was evaporated under vacuum. The residue dissolved in 10 ml of acetone was added to a precooled solution (0° C.) of sodium azide 1 g in 20 ml 50% water/acetone. After 30 minutes the mixture was diluted with water (50 ml) and extracted 3 times with 20 ml portions of benzene. The combined organic extracts were dried ($Na_2SO_4$) and filtered. The filtrate was heated in an oil bath at 80° C. until no further nitrogen evolution was observed. The solvent was evaporated under vacuum and the residue distilled under reduced pressure (80–85° C., 0.5 mmHg) affording 700 mg of the title compound.

d) Synthesis of 4-N-Butyloxycarbonyl-pent-3-en-oic acid

Tert-butanol 890 mg (12.2 mmol) was added to a solution containing the product from step c) (1 g, 6.1 mmol) in 25 ml of benzene. The whole solution was refluxed for 10 hours after which it was evaporated under vacuum. The residue was treated with pig liver esterase as described in step b) and work up as described in that step afforded 700 mg of the title compound.

The product from step d) is then used as a unit in the preparation of synthetic spacer II. These units are assembled to form spacer (II) using techniques that are well known to those skilled in the art.

EXAMPLE 10

Synthesis of Various Peptides

The peptides P24, P51, P53, P73, P52 and P54, which are shown in Table I below, were synthesized using the standard procedure described previously under the heading "Synthesis of the peptides".

Also, peptide P79, corresponding to synthetic peptide of formula I where:

X is D-Phe, Z is $(CH_2)_2$—(CO)—, D is propyl, Y is CO, W is H, and R is -Glu-Gly-Tyr-Leu-Gln-OH, was prepared by first chemically synthesizing 5-BOC-4-oxo-8-tosylguinadinooctanoic acid as described in example 3, followed by appropriate peptide assembly using the procedure described under the heading "Synthesis of the peptides".

EXAMPLE 11

Preparation of P79 (SEQ ID NO:1) (BCH-1709)

Ac-(D) Phe-Pro$^{45}$-Arg -ψ[(CO)—$CH_2$]$CH_2$—(CO)-Gln-Ser$^{50}$-His-Asn-Asp-Gly-Asp$^{55}$-Phe-Glu-Glu-Ile-Pro$^{60}$-Glu-Glu-Tyr-Leu-GlnOH 1 g of tert-Butyloxycarbonyl-Gln phenylacetamidomethyl resin (Applied Biosystems; 0.64 mmol/g) was carried through 16 cycles of synthesis involving nα-side chain deprotection (50% TFA in $CH_2Cl_2$ and coupling using 2.5 meq of protected amino acid/DCC and N-hydroxybenzo-triazole. Side chain protecting groups of standard amino acids were as follows: Asp (cyclohexyl), Glu (benzyl), His (benzyloxymethyl), Tyr (bromobenzyl), Ser (benzyl).

The synthetic protected amino acid from example 3 was coupled to Gln$^{49}$ also using DCC/N-hydroxybenzo-triazole. For optimum results, N-BOC-(D)-Phe-Pro-OH could be added at a single unit instead of individual amino acids.

The fully protected peptide resin (500 mg) was treated with hydrogen fluoride in a teflon vessel containing anisole and dimethyl sulfide (10% by volume) at −5° C. for 60 minutes. Excess HF was removed under a stream of $N_2$ and the residual mass was extracted with ether and filtered. The resin was extracted three times with glacial acetic acid and water, followed by lyophilization.

The lyophilized crude peptide was purified to homogeneity by reverse phase chromatography on an octadecyl silica (15 Å, Vydac) glass column (1.5×30 cm), 40 psi using a linear gradient of a solvent system consisting of (a) 500 ml of 0.1% TFA/$H_2O$ and (B) 1 liter of 60% acetonitrile $H_2O$ containing 0.1% TFA. Fractions corresponding to 98% purity or higher were pooled and lyophilized.

Amino acid analysis indicated: Asp (3), Ser (1), Glu (6), Gly (1), Ile (1), Leu (1), Tyr (1), Phe (2), His (1), Pro (2).

The resulting peptide showed a pseudo molecular ion corresponding to 2548.6.

EXAMPLE 12

Preparation of P102 (SEQ ID NO:2)

Ac-(D) Phe-Pro-Arg ψ[(CO)—$CH_2$]$CH_2CH_2$—(CO)-Gln-Ser-His-Asn-Asp-Gly-Asp-Phe-Glu-Glu-Ile-Pro-Glu-Glu-Tyr-Leu-Gln-OH

Amino acid analysis indicated: Asp (3.20), Ser (0.86), Gly (6.60), Gly (0.8), Ile (1.00), Leu (1.06), Tyr (0.86), Phe (1.84), His (0.88), Pro (2.10).

Pseudo molecular ion: 2562.4.

EXAMPLE 13

Preparation of P103 (SEQ ID NO:3)

Ac-(D)-Phe-Pro-Arg-ψ[(CO)—$CH_2$]—$CH_2CH_2CH_2$—(CO)-Gln-Ser-His-Asn-Asp-Gly-Asp-Phe-Glu-Glu-Ile-Pro-Glu-Glu-Tyr-Leu-Gln-OH

Amino acid analysis indicated: Asp (3.15), Ser (0.84), Gly (6.84), Gly (1.00), Ile (1.04), Leu (1.26), Tyr (0.99), Phe (2.12), His (1.00), Pro (1.55).

Pseudo molecular ion: 2576.8.

EXAMPLE 14

Preparation of P183 (SEQ ID NO:5)

Ac-(D)-Phe-Pro-Arg-ψ[(CO)—$CH_2$]—$CH_2CH_2CH_2$—(CO)—[NH—$CH_2$—CH=CH—$CH_2$—(CO)]-Asp-Phe-Glu-Pro-Ile-Pro-Leu-OH

The title peptide of this example was synthesized and purified essentially as described for P79 and its homologs with minor modifications. For example, the solid phase synthesis began with tert-butyloxycarbonyl-Leu phenylacetamidomethyl polystyrene resin (Applied Biosystems, 0.64 mmol/g). For deprotection of the t-BOC group following the Asp residue, 50% TFA in CH$_2$Cl$_2$ containing 10% ethylmethyl sulfide was used. In this way, the yield of the title peptide was optimized to greater than 60%, by HPLC (UV absorption at 215 nm).

Amino acid analysis indicated: Asp (1.00), Glu (1.07), Ile (0.94), Leu (1), Phe (1.82), Pro (3.29).

Pseudo molecular ion: 1455.

EXAMPLE 15

Preparation of P184 (SEQ ID NO:6) (BCH-1710)

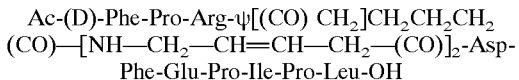

Amino acid analysis indicated: Asp (1.00), Glu (1.08), Ile (0.96), Leu (1.01), Phe (1.91), Pro (3.48).

Pseudo molecular ion: 1553.

EXAMPLE 16

Preparation of P185 (SEQ ID NO:7)

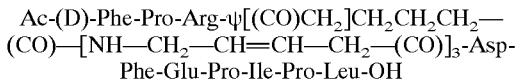

Amino acid analysis indicated: Asp (1.00), Glu (1.06), Ile (0.93), Leu (0.98), Phe (1.88), Pro (3.6).

Pseudo molecular ion: 1647.

EXAMPLE 17

Synthesis of P596 (SEQ ID NO:13) (BCH-2773)

P596 has the formula H-(D-Cha)-Pro-Arg-ψ[(CO)—CH$_2$]-(4-pyridylacetyl)-(Gly)$_4$-Asp-Tyr-Glu-Ile-Pro-Glu-Glu-Ala-Cha-(D-Glu)-OH.

P596 was synthesized using a mixed homogeneous/solid phase procedure. The C-terminal pentadecapeptide was synthesized by standard solid-phase synthesis on Pam-resin using Boc-strategy and BOP as coupling reagent. 4-Pyridylacetic acid (4-Paa) was attached to the pentadecapeptide, while still on the resin with side chain protecting groups, using BOP as coupling reagent. Boc-(D-Cha)-Pro-Arg(Z$_2$)—CH$_2$I (6 fold excess), which was prepared as described below, was then coupled to the peptide. The reaction mixture was shaken for 3 days at room temperature with a shield of light. The peptide was then cleaved from the resin using HF and was purified on reverse phase LC C$_4$ and C$_{18}$ columns.

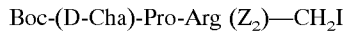

8.68 g (16 mmol) of Boc-Arg(Z$_2$)—OH (Bachem Bioscience Inc.) was stirred with 16.8 mmol N-methylmorpholinone (Aldrich) in 100 mL anhydrous tetrahydrofuran (THF) at room temperature. Then, the reaction solution was cooled to —15° C. and 16.8 mmol isobutylchloroformate (Aldrich) was added. After 10 minutes, salts were removed from the mixed anhydride by filtration, and the THF solution was cooled to –78° C. Diazomethane was generated in a mixture of 35 mL ether and 10 mL 2-methoxyethanol by adding 6.42 g (30 mmol)Diazald (Aldrich) and treatment with 5 mL ethanol and 5 mL of 70% KOH solution at 0° C. Diazomethane was distilled at 30° C. into the mixed anhydride solution and reacted overnight at 0° C. THF was then evaporated and the solid material was redissolved in 150 mL of THF, cooled to 0° C. and treated with 8 mL of 4N HCl in dioxane in small portions. Within 10 minutes the diazomethylketone was converted to the chloromethylketone. THF was evaporated, and the solid material was redissolved in ethylacetate and washed with 5% KHSO$_4$ and saturated NaHCO$_3$ solutions and neutralized by washing with NaCl saturated water and dried with Na$_2$SO$_4$. The product was crystallized from ethylacetate/hexane and recrystallized from ethanol. The overall yield was 58.3%, m.p. 67–69° C., $[\alpha]D^{23}$=–17.1 (c=0.5 acetic acid), Rt 53.5 min, M+ 575; $\delta_C$ (125.8 MHz, CDCl$_3$) ( $\underline{C}$H$_3$)$_3$C 28.26; (CH$_3$)$_3$$\underline{C}$ 80.15; (CH$_3$)$_3$C—O$\underline{C}$O 160.49; $\underline{C}$H$_2$Cl 46.91; $\underline{C}$OCH$_2$Cl 201.68; C$_\alpha$ 57.23; C$_\beta$ 26.86; C$_\gamma$ 24.54; C$_\delta$ 44.02; C$_{Guanidino}$ 163.53; for Z groups: $\underline{C}$O—OCH$_2$ 155.67+155.58; CO—$\underline{C}$H$_2$ 69.04+67.26; aromatic 136.49, 134.49, 128.94, 128.84, 128.47, 128.37, 128.12, and 128.06.

The Boc-group of Boc-Arg(Z$_2$)—CH$_2$Cl (8.7 mmol) was deprotected in HCl/Dioxane, and the product was precipitated with ether. The chloromethylketone was then coupled with a mixed anhydride prepared from 9 mmol Boc-(D-Cha)-Pro-OH [which was synthesized by mixed-anhydride coupling of Boc-(D-Cha)-OH with Pro-benzylester with following hydrogenation catalysed by Pd (5%) on activated carbon in methanol] and 9 mmol B-methylmorpholine and 9 mmol isobutylchloroformate. The solvent was then evaporated, and the residue was redissolved in ethylacetate and washed with 5% KHSO$_4$— and saturated NaHCO$_3$ and NaCl-solutions. After drying with Na$_2$SO$_4$ the solvent was evaporated. The crude tripeptidyl chloromethylketone was converted into a iodinemethylketone by stirring with 10 g of NaI in 200 mL DMF under light protection at 30–35° C. for 24 h. After evaporating DMF, the oily residue was redissolved in ethylacetate and washed with water to remove salts and dried over Na$_2$SO$_4$ and the solvent was evaporated. The oily crude Boc-(D-Cha)-Pro-Arg(Z$_2$)—CH$_2$I was coupled without further purification to the peptide on the resin as described above.

EXAMPLE 18

Synthesis of P617 (SEQ ID NO:20) (BCH-2772)

P617 has the formula: H-(D-Phe)-Pro-Arg-ψ[(CO)—CH$_2$]—S—CH$_2$—CO-(Gly)$_4$-Asp-Phe-Glu-Glu-Ile-Pro-Glu-Glu-Tyr-Leu-Gln.

P617 was synthesized using a mixed homogeneous/solid phase procedure. The C-terminal pentadecapeptide was synthesized by standard solid-phase synthesis on Pam-resin using Boc-strategy and BOP as coupling reagent. Then, Boc-Arg(Z$_2$)—CH$_2$—S—CH$_2$—COOH, of which synthesis is described below, was coupled followed by another coupling of Boc-(D-Phe)-Pro-OH (synthesized as described for Boc(D-Cha)-Pro-OH for P596). BOP and a standard coupling protocol were used in both couplings. The peptide was cleaved from resin using HF and purified as described for P596.

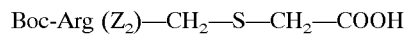

1 g (1.74 mmol) of Boc-Arg(Z$_2$)—CH$_2$Cl which was synthesized as described above was dissolved in 20 mL of anhydrous THF and treated with 17.4 mmol of mercaptoacetic acid. The reaction mixture was stirred for 48 h at room temperature and the solvent was evaporated. Under this conditions, the chloromethylketone was converted nearly quantitatively to the product, Boc-Arg(Z$_2$)—CH$_2$—S—

$CH_2$—COOH, which was then coupled to the pentadecapeptidyl-resin.

EXAMPLE 19

Following the procedure outlined in example 11, the following peptides were synthesized:

P79 (SEQ ID NO:1) (BCH-1709): Ac(D-Phe)-Pro-Arg-$(CH_2)_2(CO)$-QSHNDGDFEEIPEEYLQ-OH;

P102 (SEQ ID NO:2): Ac(D-Phe)-Pro-Arg-$(CH_2)_3(CO)$-QSHNDGDFEEIPEEYLQ-OH;

P103 (SEQ ID NO:3): Ac(D-Phe)-Pro-Arg-$(CH_2)_4(CO)$-QSHNDGDFEEIPEEYLQ-OH;

P109 (SEQ ID NO:4) (BCH-1711): Ac(D-Phe)-Pro-Arg—$CH_2(CO)$-GSHNDGDFEEIPEEYLQ-OH;

P290 (SEQ ID NO:8) (BCH-1719) Ac(D-Phe)-thioPro-Arg-$(CH_2)_2(CO)$-QSHNDGDFEEIPEEYLQ-OH;

P311 (SEQ ID NO:9) (BCH-1721): Ac(D-Cha)-Pro-Arg-$(CH_2)_2(CO)$-QSHNDGDFEEIPEEYLQ-OH;

P314 (SEQ ID NO:10) (BCH-1726): Ac(D-Cha)-Pro-Arg-$(CH_2)_2(CO)$-QSHNDGDFEPIPEEY-(Cha)-Q-OH;

BCH-2408 (SEQ ID NO:26): Ac(D-Phe)-Pro-Arg-$(CH_2)_2(CO)$-QSHNDGDFEPIPEEY-(Cha)-Q-OH; and BCH-2423 (SEQ ID NO:28): succinyl (D-Phe)-Pro-Arg-$(CH_2)_2(CO)$-QSHNDGDFEEIPEEYLQ-OH.

Following the procedure outlined in example 18, the following compounds were synthesized:

P536 (SEQ ID NO:11): (D-Cha)-Pro-Arg-$CH_2N$ (acetyl) $CH_2(CO)$-$(Gly)_4$-DYEPIPEEY-(Cha)-D-OH;

P617 (SEQ ID NO:20) (BCH-2772): H-(D-Phe)-Pro-Arg-$CH_2SCH_2(CO)$-$(Gly)_4$-DFEEPIEEYLQ-OH; and P618 (SEQ ID NO:21): Ac(D-Phe)-Pro-Arg-$CH_2SCH_2(CO)$-$(Gly)_4$-DFEEIPEEYLQ-OH.

Following the procedure outlined in example 17, the following compounds were synthesized:

P574 (SEQ ID NO:12): (D-Phe)-Pro-Arg-$CH_2$-(4-pyridylacetyl)-$(Gly)4$-DFEEIPEEYLQ-OH;

P596 (BCH-2773) (SEQ ID NO:13): (D-Cha)-Pro-Arg-$CH_2$-(4-pyridylacetic acid)-$(Gly)_4$-DYEPIPEEA-Cha-Glu-OH;

P597 (SEQ ID NO:14): (D-Cha)-Pro-Arg-$CH_2$-(4-pyridylacetyl)-$(Gly)_4$-DFEEIPEEYLQ-OH;

P603 (SEQ ID NO:15): (D-Cha)-Pro-Arg-$CH_2$-(4-pyridylacetyl)-Abu-Gly-DYEPIPEEA-(Cha)-(D-Glu)-OH;

P604 (SEQ ID NO:16): (D-Cha)-Pro-Arg-$CH_2$-(4-pyridylacetyl)-Ava-Gly-DYEPIPEEA-(Cha)-(D-Glu)-OH;

P605 (SEQ ID NO:17): (D-Cha)-Pro-Arg-$CH_2$-(4-pyridylacetyl)-Aca-Gly-DYEPIPEEA-(Cha)-(D-Glu)-OH;

P606 (SEQ ID NO:18) (BCH-2774): (D-Cha)-Pro-Arg-$CH_2$-(4-pyridylacetyl)-Aha-Gly-DYEPIPEEA-(Cha)-(D-Glu)-OH; and P609 (SEQ ID NO:19): (D-Cha)-Pro-Arg-$CH_2$-(4-pyridylacetyl)-$(Gly)_4$-DYEPIPEEA-(Cha)-(D-Glu)-OH.

Following the procedures outlined in examples 14, 15 or 16, the following compounds were synthesized:

P183 (SEQ ID NO:5): Ac(D-Phe)-Pro-Arg-$(CH_2)_4(CO)$—[N—$CH_2$—CH=CH—$CH_2$—(CO)]-DFEPIPL-OH;

P184 (SEQ ID NO:6) (BCH-1710): Ac(D-Phe)-Pro-Arg-$(CH_2)_4(CO)$—[NH—$CH_2$—CH=CH—$CH_2$—$(CO)]_2$-DFEPIPL-OH;

P185 (SEQ ID NO:7): Ac(D-Phe)-Pro-Arg-$(CH_2)_4(CO)$—[NH—$CH_2$—CH=CH—$CH_2$—$(CO)]_3$-DFEPIPL-OH;

BCH-2414 (SEQ ID NO:27): Ac(D-Phe)-Pro-Arg-$(CH_2)_4(CO)$—[NH—$CH_2$—CH=CH—$CH_2$—$(CO)]_2$-DEFPIPY-OH;

BCH-2739 (SEQ ID NO:29): Ac(D-Phe)-Pro-Arg-$(CH_2)_4(CO)$—[NH—$(CH_2)_4$—$(CO)]_2$-DFEPI-PL-OH;

BCH-2757 (SEQ ID NO:30): alpha-N-(Ac)(D-Phe)-Pro-Arg-$(CH_2)_4(CO)$-[5-aminovaleryl]-NGDFEPIPL-TFA salt;

BCH-2758 (SEQ ID NO:31): (D-Phe)-Pro-Arg-$(CH_2)_4(CO)$-[5-aminovaleryl]$_2$-DF-(4-thiahomoGlu)-PIPL-TFA salt;

BCH-2763 (SEQ ID NO:32): (D-Phe)-Pro-Arg-$(CH_2)_4(CO)$—[NH$(CH_2)_4$CO]$_2$-DFEPIPL-TFA salt; and BCH-2767 (SEQ ID NO:33): (D-Phe)-Pro-Arg-$(CH_2)_4(CO)$-[5-aminovaleryl]$_2$-FEPIPL-TFA salt.

EXAMPLE 20

Biological Data

Amidolytic Assay of Thrombin Activity

Thrombin-catalyzed hydrolysis of Tos-Gly-Pro-Arg-pNA was monitored at 405 nm on a Varian Cary 2000 double beam spectrophotometer using substrate concentrations of 2.5, 3.5, 5 and 10 $\mu$M in a final volume of 1 mL. The hydrolytic reactions were performed at 25° C. in 0.1 N Tris-HCl buffer, pH 7.8, containing 0.1 M NaCl and 0.1% PEG 6000. The reactions were initiated by addition of the substrate dissolved in 0.1 M Tris-HCl buffer, pH 7.8 to a preincubated solution of enzyme (0.4 or 0.04 nM) and variable concentrations of inhibitor dissolved in the same buffer. Initial velocities were recorded and $K_i$ values were determined graphically by weighted linear regression of Dixon plots in the case of competitive inhibition, or by the method of Baici (Baici, 1981) for hyperbolic inhibition. Fluorogenic assays were conducted using the same conditions and instrument as above operating in the fluorescence mode in the Ratio ($\lambda$ex=383 nm, $\lambda$em=455 nm). Fluorescence intensities were calibrated with 7-amino-4-methyl coumarin solution of known concentration. The specificity of the synthetic peptides of the present invention for human $\alpha$-thrombin may also be determined by comparing their relative inhibitory activities towards both human $\alpha$-thrombin and bovine $\alpha$-thrombin and trypsin by comparing Ki values obtained in the amidolytic assay of thrombin activity.

Hence, the inhibitory activity of the synthetic peptides of the present invention towards thrombin may also be assayed by determination of prothrombin time (PT, extrinsic pathway) or activated partial thromboplastin time (APTT, intrinsic pathway) of pooled reconstituted normal human plasma using a Coag-A-Mate 2001 instrument (General Diagnostics Inc., Morris Planes, N.J.) or other suitable spectrophotometer.

Thus, for the determination of prothrombin time, 50 $\mu$l of reconstituted citrated normal human plasma (Sigma, St-Louis, Mo.) is mixed with 50 $\mu$l of thromboplastin solution at 37° C. in a 400 $\mu$l cuvette. The mixture is then treated with either 200 $\mu$l of Tris-HCl buffer pH 7.8 (containing 0.1M NaCl, 0.1% PEG 6000) or variable concentrations of inhibitor in the same buffer. The clotting time is recorded following recalcification with 100 $\mu$l of 25 mM $CaCl_2$. The clotting time in the absence of inhibitor was between 19–22 sec.

The same procedure is adopted for the determination of activated partial thromboplastin time except that reconstituted plasma is activated for 3 minutes with cephalin (Sigma, St-Louis, Mo.).

Figure 1B:
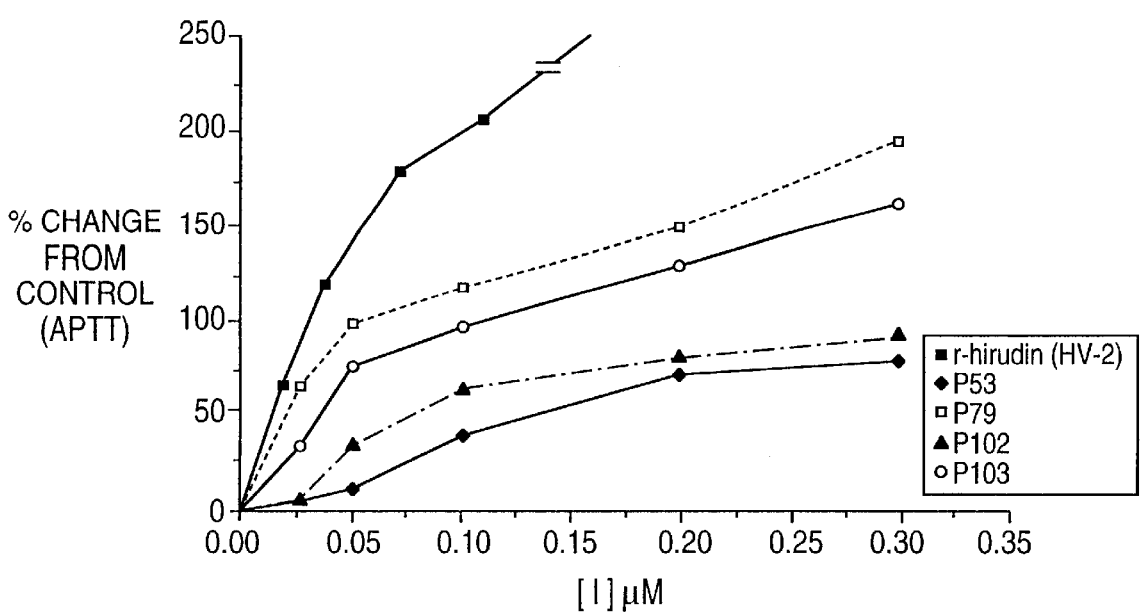
Figure 4:
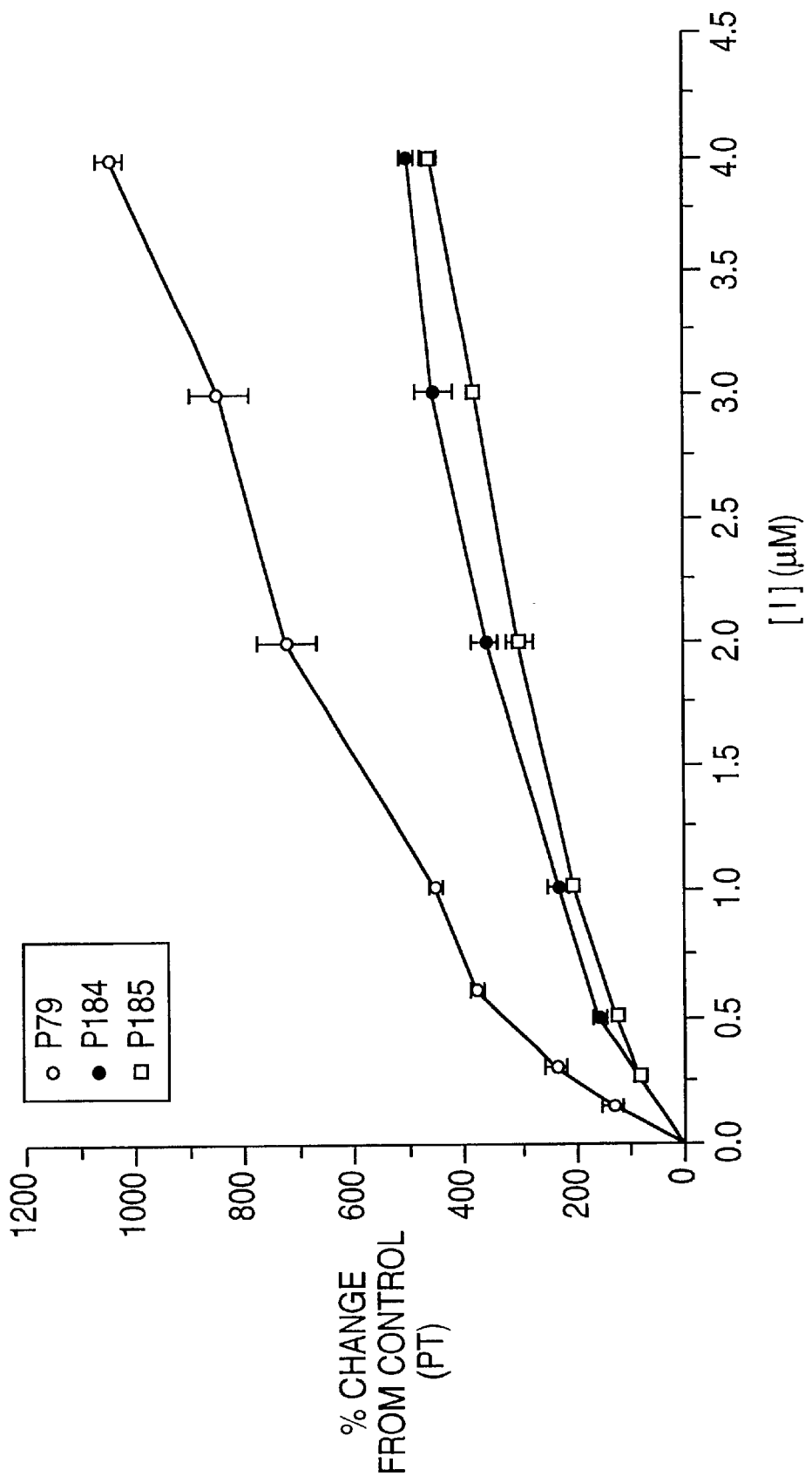
FIG. 4 represents the prothrombin time inhibition curves of normal human plasma for peptides P79, P184 and P185.

Typical APTT and PT inhibition curves are shown in FIGS. 1 and 4.

The inhibitory activity of some of the peptides of the present invention toward thrombin is reflected by their ability to inhibit thrombin-mediated platelet aggregation as shown in FIG. 2. Platelet rich plasma containing variable concentrations of P79 is treated with thrombin. Platelet aggregation, reflected by increased light transmittance is measured on a Bio Data PAP-4 aggregometer.

reactions may be prepared by mixing a thrombin solution with a Tris-HCl, pH 7.4, NaCl buffer.

These assays, when performed using some of the synthetic peptides of the present invention, demonstrated that these peptides act as bifunctional inhibitors of thrombin. Indeed, it was demonstrated that the incorporation of the two critical regions of the peptides separated by a suitable spacer provided strong thrombin inhibitors. Results are shown in Table I.

TABLE I

Inhibitory dissociation constants for the bovine and human α-thrombin mediated hydrolysis of Tosyl-Gly-Pro-Arg-AMC by hirudin peptides.

| | Analog[c] | Bovine $K_i$ $nM^b$ | Human $K_i$ $nM^b$ |
|---|---|---|---|
| | r-Hirudin HV2 | | 0.00038 ± 0.00005 |
| P24 | hirudin$^{55-65}$ | ni[a] | ni[a] |
| P51 | hirudin$^{45-55}$ | 720 ± 130 | 110 ± 3 |
| P53 | [D-Phe$^{45}$, Arg$^{47}$]hirudin$^{45-65}$ | 31 ± 6 | 2.8 ± 0.9 |
| P73 | [D-Phe$^{45}$, Ala$^{47}$]hirudin$^{45-65}$ | ni[a] | 41 ± 15 |
| P52 | [D-Phe$^{45}$, Arg$^{47}$, D-Pro$^{48}$]hirudin$^{45-65}$ | 470 ± 180 | 46 ± 3 |
| P54 | [Thr$^{45}$, Arg$^{47}$, D-Pro$^{48}$]hirudin$^{45-65}$ | 320 ± 100 | 72 ± 32 |
| P109 | [D-Phe$^{45}$, Arg$^{47}$, ψ(COCH$_2$)CO$^{47}$]hirudin$^{45-65}$ | — | Nd[d] |
| P79 (SEQ ID NO: 1) | [D-Phe$^{45}$, Arg$^{47}$, ψ(COCH$_2$)CH$_2$CH$_2$CO$^{47}$]hirudin$^{45-65}$ | — | 0.33 ± 0.03 |
| P102 (SEQ ID NO: 2) | [D-Phe$^{45}$, Arg$^{47}$, ψ(COCH$_2$)CH$_2$CH$_2$CH$_2$CO$^{47}$]hirudin$^{45-65}$ | — | 0.56 ± 0.14 |
| P103 (SEQ ID NO: 3) | [D-Phe$^{45}$, Arg$^{47}$, ψ(COCH$_2$)CH$_2$CH$_2$CH$_2$CH$_2$CO$^{47}$]hirudin$^{45-65}$ | — | 0.14 ± 0.02 |
| P183 (SEQ ID NO: 5) | [D-Phe$^{45}$, Arg$^{47}$, ψ(COCH$_2$)(CH$_2$)$_3$CO$^{47}$-(NHCH$_2$CH=CHCH$_2$CO), Pro$^{58}$, Leu$^{61}$]hirudin$^{45-61}$ | — | 300 |
| P184 (SEQ ID NO: 6) | [D-Phe$^{45}$, Arg$^{47}$, ψ(COCH$_2$)(CH$_2$)$_3$CO$^{47}$-(NHCH$_2$CH=CHCH$_2$CO)$_2$, Pro$^{58}$, Leu$^{61}$]hirudin$^{45-61}$ | — | 3.5 ± 1.8 |
| P185 (SEQ ID NO: 7) | [D-Phe$^{45}$, Arg$^{47}$, ψ(COCH$_2$)(CH$_2$)$_3$CO$^{47}$-(NHCH$_2$CH=CHCH$_2$CO)$_3$, Pro$^{58}$, Leu$^{61}$]hirudin$^{45-61}$ | — | 3.2 ± 1.1 |

[a]ni: not inhibited;
[b]mean of three determinations ± SEM;
[c]all peptides had correct amino acid analysis and showed correct pseudo molecular ions;
[d]Nd: not determined.

Fibrinogen Clotting Assay

Inhibition of fibrinogen clot formation was measured spectrophotometrically at 405 nm on a Varian DMS 90 at 37° C. 300 μL of 0.1% fibrinogen (Sigma) in 0.1M Tris-HCl, pH 7.8, containing 0.1M NaCl, 0.1% PEG 600 and variable concentrations of inhibitor in the same buffer were mixed in polystyrene cuvettes and the reaction was initiated by the addition of the enzyme (human or bovine α-thrombin 0.4 nM) in a total volume of 1 mL. The time from mixing to inflection due to clot formation was recorded for various inhibitor concentrations and IC50 values were calculated by log probit analysis. The concentrations of the inhibitors in the assays was based on the peptide content.

Various other assays may be used to determine the anti-coagulant activity of the peptides of the present invention. Hence, the inhibitory activity of the synthetic peptides of the present invention towards thrombin may also be assayed by the inhibition of activated partial thromboplastin times (APTT intrinsic pathway or prothrombin time PT extrinsic pathway). Thus, the anticoagulant activity may be determined by assaying APTT of pooled, normal human plasma with a Coag-A-Mate 2001 instrument (General Diagnostics Inc., Morris Planes, N.J.).

Furthermore, the synthetic peptides of the present invention may be tested for inhibition of thrombin-catalyzed hydrolysis of the tripeptidyl P-nitroanilide substrate tosyl-Gly-Pro-Arg-P-nitroanilide (Chromozym TH, Boehringer-Mannheim, Indianapolis, Ind.) spectrophotometrically at 420 nm on a Cary 219 double-beam spectrophotometer. The Therefore, the enhanced enzyme affinity and in vitro anticoagulant effect may be attributed directly to a cooperative intramolecular binding mechanism. For example, if substituent X of the compound of formula I is D-Phe, this will render region (i) suitable to bind with the extended hydrophobic region of the active site of thrombin. The requirements for region (ii) to bind to a non-catalytic site of thrombin are different from those of region (i).

It is clear that the incorporation of these two regions into a single molecule separated by a suitable linker substantially increases the affinity of the compounds for thrombin. In fact, the combination of separate $IC_{50}$ doses of the two independent regions results in the exact doubling of the clotting time whereas greater activity is obtained if the two regions are joined by a linker. It therefore appears that dual cooperative binding of the bifunctional inhibitors of the present invention takes place when these are contacted with thrombin. The linker serves as a suitable spacer for the bridging of an auxiliary site (region (ii)) and a catalytic site (region (i)) as well as an apolar binding site adjacent to the catalytic site.

The various experiments have also demonstrated that while D-Phe-Pro-Arg-Pro-OH and Nα-acetyl desulfo hirudin$^{55-65}$ independently inhibited fibrin clot formation by bovine α-thrombin with $IC_{50}$ values of 250 μM and 3.5 μM respectively, their incorporation into a single molecule separated by a spacer corresponding to hirudin residues 49–54 afforded an inhibitor with an $IC_{50}$=70±20 nM (bovine α-thrombin) and 4±0.8 nM (human α-thrombin). The effect of combining separate $IC_{50}$ doses of hirudin[45-65] and D-Phe-Pro-Arg-Pro-OH resulted only in the doubling of the fibrinogen clotting time, while the contribution of the spacer was negligible. The synergistic effect observed for P53 in the clotting assay was corroborated by results of the fluorogenic assay where this analog emerged as a pure competitive inhibitor compared to P51 with Ki values almost 50 fold lower than the latter. Interesting thrombin inhibitory activities have been obtained with peptides P79, P102, P103 as well as "truncated" peptides P184 and P185.

Antithrombotic Activity in the Arteriovenous Shunt Model

Experimental Procedure

The rat anaesthetized with urethane was fixed in supine position on a temperature-controlled heating plate. The right carotid artery and the left jugular vein were catheterized with short polyethylene catheters (Portex, PE 50). The catheters were filled with physiological saline solution and clamped. The two ends of the catheters were connected with a 2-cm glass capillary (internal diameter 1.0 mm) acting as a thrombogenic surface, 5 min after intravenous administration of the test substance or its solvent (control) the clamps occluding the arteriovenous shunt are opened. The blood flowing through the shunt led to a rapid rise in temperature of the glass capillary from room temperature to body temperature. The temperature of the capillary served as an indicator for the patency of the shunt. The temperature was measured by means of a NiCrNi-thermo-couple.

Results

Antithrombotic effect of P79 compared to recombinant hirudin in the arteriovenous shunt model in rats 5 min. after intravenous administration (n=number of animals used). Results are shown in Table II below.

TABLE II

| Substance | *ED15 mg/kg | (95% confidence limits) | n |
|---|---|---|---|
| P79 (SEQ ID NO:1) (BCH-1709) | 0.42 | (0.27–1.19) | 15 |
| r-hirudin | 1.42 | (1.14–1.92) | 32 |

*dose which causes a prolongation of the time until occlusion of the shunt by 15 min.

Stability of Polypeptides in Plasma

The peptides of this invention were evaluated for in vitro plasma stability against proteolysis. The results in the accompanying figure are an illustrative example of the comparative stability of P53 and P79 (SEQ ID NO:1) (otherwise designated as hirutonin II).

600 μg of peptide was mixed with 250 μl of reconstituted normal human plasma, 250 μl of thromboplastin, 600 μg of calcium chloride and 50 mM $NaHPO_4$ buffer pH 7.8 to a final volume of 900 μl.

The mixture was incubated at 37° C. and 100 μl aliquots were removed at designated time intervals. 20 μl of 10% trichloroacetic acid was added to individual aliquot and centrifuged at 12×K for 10 minutes. The supernatant was injected on a C18 analytical column and chromatographed by standard elution procedure (i.e. at 60% 0.1% TFA/H2O to 0.1 TFA in $CH_3CN$).

Figure 3:
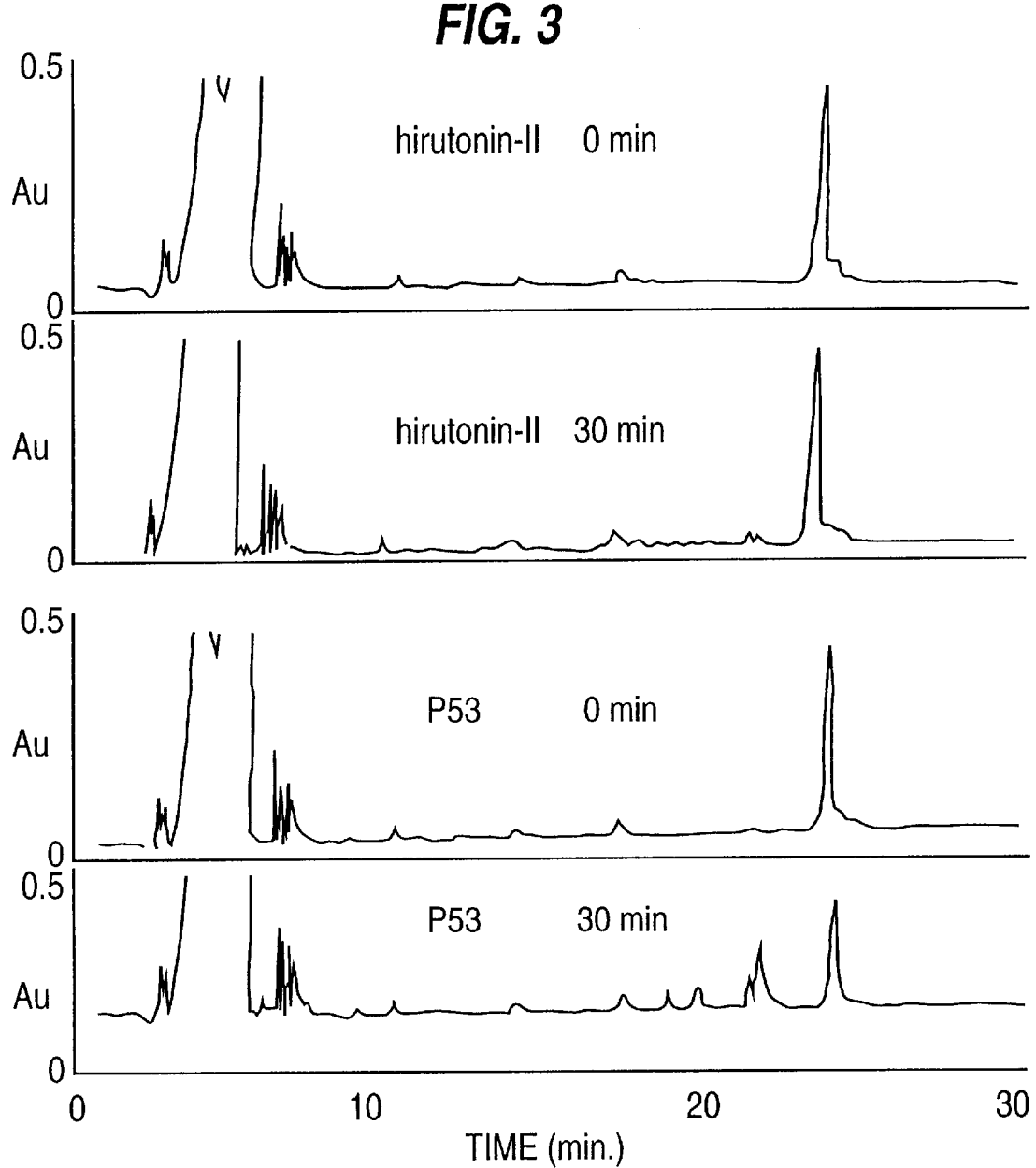
FIG. 3 represents the stability of various polypeptides in plasma.

The comparative results shown in FIG. 3 illustrate that whereas P53 is greater than 50% degraded after 30 minutes, P79 (hirutonin II) showed minimal or no proteolysis.

Ferric Chloride Injury-induced Thrombosis Model

Species: Rat, male, Sprague-Dawley.

Weight: 375–450g

Experimental Study

The $FeCl_3$ induced arterial injury model assays were conducted according to Kurz, K. D., Main, R. W., Sandusky, G. E., Thrombosis Research 60; 269–280, 1990 and Schumacher, W. A. et al. J. pharmacology and experimental therapeutics 267; 1237–1242, 1993.

Male, Sprague-Dawley (375–450 g) were anesthetized with Urethane (1500 mg\kg IP). Animals were laid on a heating pad which was maintained at 37° C. The carotid artery was approached through a midline cervical incision. Carefully blunt dissection was used to expose and isolate the vessel from the carotid sheath. Using forceps, the artery was lifted to provide clearance to insert two small polyethylene tubing (PE-205) underneath it. The temperature probe (Physitemp MT23/3)™ was placed between the PE-205 and the artery. The vessel temperature was monitored for 60 minutes after application of $FeCl_3$. Vessel temperature changes were recorded on a thermister (Cole-Palmer Model 08533-41). Injury was induced by application of a small disc (3 mm dia.) of Whatman™ No.1 filter paper previously dipped in a 35% solution of $FeCl_3$ on the carotid artery above the temperature probe. The site of the experiment was covered with aluminum foil in order to protect the $FeCl_3$ from degradation by light.

The time between the Ferric Chloride application and the time at which the vessel temperature decreases abruptly (>2.4° C.), was recorded as the time to occlusion (TTO) of the vessel.

Before the start of the experiment, one blood sample was drawn (1 ml) in a tube of 0.105M buffered citrate solution (from the eye's sinus or cannulated jugular or femoral vein) and the animal was exsanguinated at the end. All the samples were kept on ice and centrifuged as soon as possible at 2000 Rpm for 10 min., 4° C. The plasma was analyzed in duplicate for activated partial thromboplastin time on a haemostasis analyzer (STAGO ST4™).

From a group of four animals, two arteries were stored at −80° C. for further analysis. The others were observed under a light microscope at 40× (Leica™) for quantification of the occlusion (complete, partial, no occlusion).

In some studies, the animal was receiving the compound by i.v. infusion instead of a bolus. In this case, the jugulars and femoral veins were cannulated with Sylastic tubing (I.D. 0.025IN). This left jugular was used for blood sampling and the right one for the infusion line. The compound was infused 30 minutes before injury and then for an other 30 minutes post-injury. Blood samples were taken at time 0, 30 and 60 minutes for APTT test and thrombin test (1 ml of blood/90 ul of citrated buffer).

TABLE III

Effect on antithrombin activity in vitro and on antithrombotic activity in vivo in a model of ferric chloride injury-induced thrombosis in carotid artery in rats.

| P number (BCH number) | Ki (pM) | IC50 dTT (nM)* | IC50 plasma clotting time (nM)** | Dose to double patency time (mg/kg) | IC50 thrombin-induced platelet aggregation (nM) |
|---|---|---|---|---|---|
| P79 (SEQ ID NO: 1) (1709) | 500 | 1.9 | 9 | 1 | 2 |
| (1710) (SEQ ID NO: 6) | 1500 | 10.5 | 52 | 1–2 | 6 |

TABLE III-continued

Effect on antithrombin activity in vitro and on antithrombotic activity in vivo in a model of ferric chloride injury-induced thrombosis in carotid artery in rats.

| P number (BCH number) | Ki (pM) | IC50 dTT (nM)* | IC50 plasma clotting time (nM)** | Dose to double patency time (mg/kg) | IC50 thrombin-induced platelet aggregation (nM) |
|---|---|---|---|---|---|
| P109 (SEQ ID NO: 4) (1711) | 2250 | ND | 38 | ND | ND |
| P290 (SEQ ID NO: 8) (1719) | 900 | ND | 11 | ND | ND |
| P311 (SEQ ID NO: 9) (1721) | 160 | 1.35 | 3 | ND | ND |
| P314 (SEQ ID NO: 10) (1726) | 20 | 1.3 | 1.4 | 1 | 4.5 |
| P582 | 0.053 | ND | ND | ND | ND |
| P596 (SEQ ID NO: 13) | 0.046 0.051$^2$ | ND | ND | ND | ND |
| P603 (SEQ ID NO: 15) | 0.067 | ND | ND | ND | ND |
| P604 (SEQ ID NO: 16) | 0.050 | ND | ND | ND | ND |
| P605 (SEQ ID NO: 17) | 0.068 | ND | ND | ND | ND |
| P606 (SEQ ID NO: 18) | 0.040 0.073$^2$ | ND | ND | ND | ND |
| (2408) (SEQ ID NO: 26) | 75 | 1 | 1.8 | 0.5 | 11 |
| (2414) (SEQ ID NO: 27) | 1000 | 6.23 | 10.5 | ND | ND |
| (2423) (SEQ ID NO: 28) | 450 | 1.15 | 10 | 1 | 135 |
| (2739) (SEQ ID NO: 29) | 4000 | 14.5 | 78 | 1 | 20 |
| (2757) (SEQ ID NO: 30) | 11000 | 25.5 | 190 | >2 | 50 |
| (2758) (SEQ ID NO: 31) | 950 | 4.9 | 30 | 4 | 10 |
| (2763) (SEQ ID NO: 32) | 100 | 1.3 | 3.1 | 1 | 0.7 |
| (2767) (SEQ ID NO: 33) | 40000 | 165 | 700 | >2 | ND |
| r-Hirudin | 0.4 | ND | ND | 1 | ND |

The dose of heparin needed to cause a doubling in patency time is 200 U/kg.
ND denotes not determined. Values are means for 3–5 observations.
Patency time in control (saline-treated) rats is 19 ± 1 min (n = 11).
*Concentration of compound required to double thrombin time in buffer containing fibrinogen.
**Concentration of compound required to inhibit human plasma clotting time by 50%.
1 - first test; 2 - second test Venous Thrombosis Model (Balloon Catheter Induced-injury Model.)

Rats ranging in weight from 350 g–450 g were anaesthetized with urethane [50%] at 1500 mg/kg IP. The abdomen and neck were shaved and prepared for surgery.

An incision was made from the base of the sternum to approximately 10–20 mm up from the penile sheath. Another incision was made across the end of the incision (90 degree) to create a flap to be hemostat open. All intestines were moved to one side and applicator sticks were used to clear away any adventicia from around the abdominal aorta as well as the inferior vena cava. Two sutures were loosely looped around the vein(1) and the vein and artery(2), just posterior to the renal veins and arteries. All other branches coming off dorsally from the vena cava were ligated as well as any other veins which may branch of this vein (approximately 4–6 depending on rat). Two more sutures were looped around the vein(1) and artery and vein(2) at the bifurcation of the femoral vein and artery. The right jugular vein was isolated, for later injection of compound.

An incision in the upper interior leg was made and the femoral vein and artery were exposed. The femoral vein was isolated and two sutures were looped around it. One suture was ligated distally, and the other one was pulled tight (proximal) to stop blood flow through the vessel. A very small incision was made into the vein and a 2F fogarty catheter was inserted. The catheter was fed up the femoral vein to the upper sutures (near the renal veins). At this point, inject the compound via the isolated right jugular vein and wait 1 minute. At 1 minute inflate the fogarty catheter with enough saline to distend the vena cava, but still allowing the catheter to be pulled back down to the point of femoral bifurcation without bursting the vessel. This procedure was repeated 3 times. After the third passage, the catheter was removed and as quickly as possible, the femoral incision was ligated with the proximal suture and the suture which was looped around only the vena cava was ligated to stop return flow and allow thrombus growth and the timer was set for 30 minutes.

At this point, the intestines may be placed back in the body cavity, and moistened with saline if any drying has occurred, and skin kept closed with hemostat.

At approximately 2–3 minutes before "incubation" is up, the hemostat was removed, and intestines were once again moved from the body cavity. The sutures at both ends (two at each end) of the vena cava were prepared for ligation being careful not to disturb the area of vena cava where thrombus was being formed. At the end of 30 minutes, sutures were ligated, and that whole section of the vena cava was removed.

The vena cava was carefully split, and the formed thrombus was taken out and placed on a preweighed piece of weigh paper. The wet weight was taken and then the thrombus was allowed to dry overnight at room temperature. The dry weight of the thrombus was taken, and also noted.

Results are recorded in Table IV below. As is shown, BCH2408 and 2763 achieve patency with a minimum bolus similar to that of hirulog BCH1724.

TABLE IV

Effect of compounds given as i.v. bolus on venous thrombosis induced in vena cava following balloon catheter injury and stasis in rats.

| BCH number | N | Minimum Bolus dose needed to achieve patency (mg/kg) |
|---|---|---|
| Hirulog (1724) | 4 | 0.05–0.125 |
| 2408 (SEQ ID NO:26) | 4 | 0.0125–0.05 |
| 1710 (SEQ ID NO:6) | 4 | 0.5–2 |

TABLE IV-continued

Effect of compounds given as i.v. bolus on venous thrombosis induced in vena cava following balloon catheter injury and stasis in rats.

| BCH number | N | Minimum Bolus dose needed to achieve patency (mg/kg) |
|---|---|---|
| 2739 (SEQ ID NO:29) | 4 | 0.05–2 |
| 2763 (SEQ ID NO:32) | 4 | 0.05–0.5 |

Dose of heparin needed to achieve patency is 10–15 U.
N= number of rats tested.

Increase in APTT

INFUSION MODEL 1

Pharmacodynamic: Time Curve of APTT

Rat (Sprague-Dawley), male, ranging from 450–500 g were anaesthetized with urethane [50%] at 1500 mg/kg IP. Animal was laid on a heated pad at 37° C. An incision was made on the neck and the right jugular was isolated from surrounding tissue cannulated with Sylastic tubing (I.D.O.0.025 in) for blood sampling. The right femoral vein was cannulated for the infusion with the same size of tubing. The compound was infused for an hour at a rate of 1 ml/hr. The dose for the bolus and the infusion was established by previous test. First, blood sample was taken and then the femoral line was hooked to the pump. The bolus was injected by the jugular and then the infusion was started.

A volume of 0.5 ml of blood was taken into 50 ul of sodium citrate buffer at 0.105M at specific times: 0, 1, 5, 15, 30, 40, 50, 60 and 90 minutes. The samples were centrifuged and plasmas were analyzed on a ST4 BIO de DIAGNOSTICA STAGO.

Activated Partial Thromboplastin Time Test

Cuvette-strips and balls were placed in incubation area for prewarming for at least 3 minutes. The plasma and the PTT Automate (cat.NO.00480) were combined in the cuvette for an incubation of 180 sec. After the incubation, the cuvettes were transferred in the test column area and the calcium chloride sol. [0.025M] prewarmed at 37° C. was added to it.

INFUSION MODEL 2

Combine with Ferric Chloride [35%] Induced Arterial Thrombosis Model

Rats (Sprague-Dawley), male, ranging from 375–410 g were anaesthetized with Urethane [50%] at 1500 mg/kg IP. Animal was laid on an heated pad at 37° C. to keep his body temperature. The carotid artery was approached through a midline cervical incision. Careful blunt dissection was used to expose and isolate the vessel from the carotid sheath. The right jugular was isolated and cannulated with Sylastic tubing (I.D. 0.025IN) for blood sampling. The right femoral was cannulated with the same size of tubing for infusion line. The animal was placed on the heated pad and the first blood sample was taken in citrated buffer (1 ml/100 ul buffer). The line from the femoral was hooked to the pump and with forceps, the carotid was lifted and two small polypropylene tubing (PE-205) was inserted underneath it. The temperature probe was placed between the tubing and the artery.

Temperature was recorded for 90 minutes. First the bolus was given and then the infusion was started. After 30 minutes of infusion, a second blood sample was taken and then the ferric chloride disc was placed on the artery above the temperature probe. The injured site was covered with aluminum foil. At the end of a further 60 minutes, the third sample was taken and the animal was sacrificed.

All the samples were kept on ice. At the end, they were centrifuged and analyzed on the STAGO BIO4 for the APTT and thrombin time tests.

Activated Partial Thromboplastin Time Test:

Cuvette-strips and balls were placed in incubation area for prewarming for at least 3 minutes. The plasma and the PTT Automate (cat.NO.00480) were combined in the cuvette for an incubation of 180 sec. After the incubation, the cuvettes were transferred in the test column area and the calcium chloride sol. [0.025M] prewarmed at 37° C. was added to it.

Thrombin Time Test:

Cuvette-strips and balls were placed in incubation area for prewarming for at least 3 minutes. The plasma was incubated for 60 seconds and then transferred to the test column area where the thrombin prest was dispensed.

The results are reported in Table V. The dose ranging APTT for BCH1710 is shown in FIG. 5.

TABLE V

Intravenous dose (bolus followed by infusion) of thrombin inhibitors needed to cause 2–4 fold increase in APTT.

| P number (BCH number) | N | Bolus Dose (mg/kg) | Infusion Dose (mg/kg/min) |
|---|---|---|---|
| P79 (SEQ ID NO:1) | 3 | 0.15 | 20 |
| (1710) (SEQ ID NO:6) | 2 | 1 | 125 |
| (2408) (SEQ ID NO:26) | 3 | 0.15 | 15 |
| (2739) (SEQ ID NO:29) | 3 | 1 | 100 |
| (2759) | 1 | 1 | 100 |
| (2763) (SEQ ID NO:32) | 3 | 0.25 | 20 |
| r-Hirudin | 2 | 0.15 | 15 |

To achieve the same increase in APTT, heparin is needed to be given as 25 U bolus and 0.5 U/kg/min infusion.

Pig Angioplasty Model

The study investigates the dose range required to inhibit platelet deposition on arterial media and aggregation ex vivo in the pig using a bolus and infusion regimen of the compounds of the invention. The study was carried out according to Lam, J. Y. T. et al., Circulation 84:2, August 1991, 814–820. A brief outline of the protocol follows.

Normal 3–4 month old pigs were used. In all pigs, autologous platelets were labeled with 300–400 $\mu$Ci $^{111}$In-tropolone 18–24 hours before angioplasty. The pigs were sedated with 300 mg i.m. ketamine. After inhalation of the ether, the pigs were intubated, mechanically ventilated with room air by a respirator and maintained anesthetized with 0.5% halothane. Immediately after catheter insertion, a single bolus of heparin was administered to animals receiving platelet-inhibitor therapy and their matching controls corresponding to a dose less than 3.1 units/kg/min. Heparin was not administered to animals receiving hirudin or their matching controls.

An 8F balloon dilation catheter was advanced under fluoroscopic control through a right femoral cut down into the left and right common carotid arterial segment between the fifth and fourth vertebrae. Five inflations were performed, 30 seconds each at 6 atm with 60 seconds between inflations. The angiographic lumen diameter before dilation ranged from 5 to 6 mm during dilation, the diameter of the inflated balloon within the artery was not more than 10% greater than the original arterial lumen.

The pigs were given an overdose of pentobarbital and perfused with 2% glutaraldehyde and 1% paraformaldehyde in 0.1M cacodylate physiological pressure for 15 minutes to fix the arteries in situ. The carotid arteries were then removed, cleaned, and prepared for analysis. The dilated portion of the fixed carotid artery was divided into two equal segments, and a similar-sized segment was taken from the adjacent proximal and distal ends.

The platelet deposition on each dilated artery was calculated from the platelet counts and $^{111}$In activity on the arterial wall and in the blood obtained. The percentage of radioactivity bound to platelets was determined and the number of platelets per counts per minute was calculated from known blood platelet counts. The number of platelets deposited on the arterial segments per square centimeter was calculated by dividing the arterial segment counts per minute by both the number of platelets per counts per minute and the arterial surface area.

The results are indicated in Table VI below for BCH1710, and in FIG. 6 for a comparison of the inhibition of BCH1710, and controls.

TABLE VI

EX vivo platelet deposition on arterial media superfusion chamber (mean of three determination per animal) of BCH-1710 after an intravenous bolus of 0.2 mg/kg followed by infusion at 0.2 mg/kg/hr.

| animal | baseline platelet deposition (%) | after drug infusion (% of control) |
|---|---|---|
| 1 | 100 | 31.9 |
| 2 | 100 | 23.7 |
| 3 | 100 | 3.7 |
| 4 | 100 | 84.3 |

X±SEM=39.8±12.7% of control; paired T P=0.0001

After four animals studied, BCH-1710 decrease platelet deposition on arterial media by a mean of 61.2% relative to baseline control.

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 20 amino acids
      (B) TYPE: amino acid
      (D) TOPOLOGY: unknown (ii) MOLECULE TYPE: peptide (ix) FEATURE:
      (A) NAME/KEY: Modified-site
      (B) LOCATION: 1
      (D) OTHER INFORMATION: /label= Acetyl-D-config
        /note= "An acetyl group is attached to the
        N-terminal of Phenylalanine which is in the
        D-configuration. "

(ix) FEATURE:
      (A) NAME/KEY: Modified-site
      (B) LOCATION: 3..4
      (D) OTHER INFORMATION: /label= Linker
        /note= "Portion of the linker is  -(CH2)2(CO)-,
        and is used to link the third residue, Arginine,
        to the forth residue, Glutamine."

(xi) SEQUENCE DESCRIPTION: SEQ ID NO:1:

Phe Pro Arg Gln Ser His Asn Asp Gly Asp Phe Glu Glu Ile Pro Glu
1            5                   10                15

Glu Tyr Leu Gln
        20

(2) INFORMATION FOR SEQ ID NO:2:

(i) SEQUENCE CHARACTERISTICS:
      (A) LENGTH: 20 amino acids
      (B) TYPE: amino acid
      (D) TOPOLOGY: unknown (ii) MOLECULE TYPE: peptide (ix) FEATURE:
      (A) NAME/KEY: Modified-site
      (B) LOCATION: 1

```
            (D) OTHER INFORMATION: /label= Acetyl-D-config
                /note= "An acetyl group is attached to the
                N-terminal of Phenylalanine which is in the
                D-configuration."

(ix) FEATURE:
            (A) NAME/KEY: Modified-site
            (B) LOCATION: 3..4
            (D) OTHER INFORMATION: /label= Linker
                /note= "Portion of the linker is  -(CH2)3(CO)-,
                and is used to link the third residue, Arginine,
                to the fourth residue, Glutamine."

(xi) SEQUENCE DESCRIPTION: SEQ ID NO:2:

Phe Pro Arg Gln Ser His Asn Asp Gly Asp Phe Glu Glu Ile Pro Glu
1               5                   10                  15

Glu Tyr Leu Gln
            20

(2) INFORMATION FOR SEQ ID NO:3:

(i) SEQUENCE CHARACTERISTICS:
            (A) LENGTH: 20 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= Acetyl-D-config
                /note= "An acetyl group is attached to the
                N-terminal of Phenylalanine which is in the
                D-configuration."

(ix) FEATURE:
            (A) NAME/KEY: Modified-site
            (B) LOCATION: 3..4
            (D) OTHER INFORMATION: /label= Linker
                /note= "Portion of the linker is  -(CH2)4(CO)-,and
                is used to link the third residue, Arginine, to
                the fourth residue, Glutamine."

(xi) SEQUENCE DESCRIPTION: SEQ ID NO:3:

Phe Pro Arg Gln Ser His Asn Asp Gly Asp Phe Glu Glu Ile Pro Glu
1               5                   10                  15

Glu Tyr Leu Gln
            20

(2) INFORMATION FOR SEQ ID NO:4:

(i) SEQUENCE CHARACTERISTICS:
            (A) LENGTH: 20 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= Acetyl-D-config
                /note= "An acetyl group is attached to the
                N-terminal of Phenylalanine which is in the
                D-configuation."

(ix) FEATURE:
            (A) NAME/KEY: Modified-site
            (B) LOCATION: 3..4
```

(D) OTHER INFORMATION: /label= Linker
            /note= "Portion of the linker is -(CH2)(CO)- and
            is used to link the third residue Arginine to the
            fourth residue Glycine."

(xi) SEQUENCE DESCRIPTION: SEQ ID NO:4:

Phe Pro Arg Gly Ser His Asn Asp Gly Asp Phe Glu Glu Ile Pro Glu
1               5                   10                  15

Glu Tyr Leu Gln
            20

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= Acetyl-D-config
            /note= "An acetyl group is attached to the
            N-terminal of Phenylalanine which is in the
            D-configuration."

(ix) FEATURE:
        (A) NAME/KEY: Modified-site
        (B) LOCATION: 3..4
        (D) OTHER INFORMATION: /label= Linker
            /note= "Portion of the linker is
            -(CH2)4(CO)-[NH-CH2-CH=CH-CH2-(CO)]- and is used
            to link the third residue Arginine to the fourth (xi) SEQUENCE DESCRIPTION: SEQ ID NO:5:

Phe Pro Arg Asp Phe Glu Pro Ile Pro Leu
1               5                   10

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= Acetyl-D-config
            /note= "Acetyl group is attached to the N-terminal
            of Phenylalanine which is in the D-configuration."

(ix) FEATURE:
        (A) NAME/KEY: Modified-site
        (B) LOCATION: 3..4
        (D) OTHER INFORMATION: /label= Linker
            /note= "Portion of the linker is
            (CH2)4(CO)-[NH-CH2-CH=CH-CH2-CO]2 and is used to
            link the third residue Arginine to the fourth (xi) SEQUENCE DESCRIPTION: SEQ ID NO:6:

Phe Pro Arg Asp Phe Glu Pro Ile Pro Leu
1               5                   10

(2) INFORMATION FOR SEQ ID NO:7:

(i) SEQUENCE CHARACTERISTICS:
       (A) LENGTH: 10 amino acids
       (B) TYPE: amino acid
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION: /label= Acetyl-D-config
           /note= "Acetyl group is attached to the N-terminal
           of Phenylalanine which is in the D-configuration."

(ix) FEATURE:
       (A) NAME/KEY: Modified-site
       (B) LOCATION: 3..4
       (D) OTHER INFORMATION: /label= Linker
           /note= "Linker is
           (CH2)4(CO)-[NH-CH2-CH=CH-CH2-CO]3 and is used to
           link the third residue Arginine to the forth (xi) SEQUENCE DESCRIPTION: SEQ ID NO:7:

Phe Pro Arg Asp Phe Glu Pro Ile Pro Leu
1               5                   10

(2) INFORMATION FOR SEQ ID NO:8:

(i) SEQUENCE CHARACTERISTICS:
       (A) LENGTH: 20 amino acids
       (B) TYPE: amino acid
       (D) TOPOLOGY: unknown (ii) MOLECULE TYPE: peptide (ix) FEATURE:
       (A) NAME/KEY: Modified-site
       (B) LOCATION: 1
       (D) OTHER INFORMATION: /label= Acetyl-D-config
           /note= "Acetyl group is attached to the N-terminal
           of Phenylalanine which is in the D-configuration."

(ix) FEATURE:
       (A) NAME/KEY: Modified-site
       (B) LOCATION: 3..4
       (D) OTHER INFORMATION: /label= Linker
           /note= "Portion of the linker is (CH2)2(CO)- and
           is used to link the third residue Arginine to the
           fourth residue Glutamine. "

(ix) FEATURE:
       (A) NAME/KEY: Modified-site
       (B) LOCATION: 2
       (D) OTHER INFORMATION: /label= thio
           /note= "The second residue Proline is substituted
           with sulfur to form thio..."

(xi) SEQUENCE DESCRIPTION: SEQ ID NO:8:

Phe Pro Arg Gln Ser His Asn Asp Gly Asp Phe Glu Glu Ile Pro Glu
1               5                   10                  15

Glu Tyr Leu Gln
            20

(2) INFORMATION FOR SEQ ID NO:9:

(i) SEQUENCE CHARACTERISTICS:
       (A) LENGTH: 19 amino acids
       (B) TYPE: amino acid
       (D) TOPOLOGY: unknown (ii) MOLECULE TYPE: peptide

```
    (ix) FEATURE:
         (A) NAME/KEY: Modified-site
         (B) LOCATION: 1
         (D) OTHER INFORMATION: /label= Acetyl-D-Cha
             /note= "Acetyl group is attached to the N-terminal
             of Cyclohexylalanine which is in the
             D-configuration. D-Cha is attached to the first (ix) FEATURE:
         (A) NAME/KEY: Modified-site
         (B) LOCATION: 2..3
         (D) OTHER INFORMATION: /label= Linker
             /note= "Portion of the linker is (CH2)2(CO)- and
             is used to link the second residue Arginine to the
             third residue Glutamine. "

(xi) SEQUENCE DESCRIPTION: SEQ ID NO:9:

Pro Arg Gln Ser His Asn Asp Gly Asp Phe Glu Glu Ile Pro Glu Glu
1               5                   10                  15

Tyr Leu Gln (2) INFORMATION FOR SEQ ID NO:10:

(i) SEQUENCE CHARACTERISTICS:
         (A) LENGTH: 18 amino acids
         (B) TYPE: amino acid
         (D) TOPOLOGY: unknown (ii) MOLECULE TYPE: peptide (ix) FEATURE:
         (A) NAME/KEY: Modified-site
         (B) LOCATION: 1
         (D) OTHER INFORMATION: /label= Acetyl-D-Cha
             /note= "Acetyl group is attached to the N-terminal
             of Cyclohexylalanine which is in the
             D-configuration. D-Cha is attached to the first (ix) FEATURE:
         (A) NAME/KEY: Modified-site
         (B) LOCATION: 2..3
         (D) OTHER INFORMATION: /label= Linker
             /note= "Portion of the linker is (CH2)2(CO)- and
             is used to link the second residue Arginine to the
             third residue Glutamine. "

(ix) FEATURE:
         (A) NAME/KEY: Modified-site
         (B) LOCATION: 17..18
         (D) OTHER INFORMATION: /label= Cha
             /note= "Cyclohexylalanine is included within the
             peptide chain between the 17th reside Tyrosine and
             the 18th residue Glutamine by peptide linkage."

(xi) SEQUENCE DESCRIPTION: SEQ ID NO:10:

Pro Arg Gln Ser His Asn Asp Gly Asp Phe Glu Pro Ile Pro Glu Glu
1               5                   10                  15

Tyr Gln (2) INFORMATION FOR SEQ ID NO:11:

(i) SEQUENCE CHARACTERISTICS:
         (A) LENGTH: 16 amino acids
         (B) TYPE: amino acid
         (D) TOPOLOGY: unknown (ii) MOLECULE TYPE: peptide (ix) FEATURE:
         (A) NAME/KEY: Modified-site
         (B) LOCATION: 1
```

(D) OTHER INFORMATION: /label= D-Cha
                /note= "Cyclohexylalanine in the D-configuration
                is attached to the N-terminal of the first residue
                Proline through peptide linkage."

(ix) FEATURE:
            (A) NAME/KEY: Modified-site
            (B) LOCATION: 2..3
            (D) OTHER INFORMATION: /label= Linker
                /note= "Portion of the linker is
                CH2N(COCH3)CH2(CO)- and is used to link the second
                residue Arginine to the third residue Glycine. "

(ix) FEATURE:
            (A) NAME/KEY: Modified-site
            (B) LOCATION: 15..16
            (D) OTHER INFORMATION: /label= Cha
                /note= "Cyclohexylalanine is included within the
                peptide chain and is between the 15th residue
                Tyrosine and the 16th residue Aspartic acid (xi) SEQUENCE DESCRIPTION: SEQ ID NO:11:

Pro Arg Gly Gly Gly Gly Asp Tyr Glu Pro Ile Pro Glu Glu Tyr Asp
1               5                   10                  15

NFORMATION FOR SEQ ID NO:12:

(i) SEQUENCE CHARACTERISTICS:
            (A) LENGTH: 18 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= D-configuration
                /note= "The first residue Phenylalanine is in the
                D-configuration."

(ix) FEATURE:
            (A) NAME/KEY: Modified-site
            (B) LOCATION: 3..4
            (D) OTHER INFORMATION: /label= Linker
                /note= "Portion of the linker is
                CH2(4-pyridylacetyl)- and is used to link the
                third residue Arginine to the fourth residue (xi) SEQUENCE DESCRIPTION: SEQ ID NO:12:

Phe Pro Arg Gly Gly Gly Gly Asp Phe Glu Glu Ile Pro Glu Glu Tyr
1               5                   10                  15
Leu Gln (2) INFORMATION FOR SEQ ID NO:13:

(i) SEQUENCE CHARACTERISTICS:
            (A) LENGTH: 16 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= D-Cha
                /note= "Cyclohexylalanine in the D-configuration
                is attached to the N-terminal of the first residue
                Proline by peptide linkage."

(ix) FEATURE:
            (A) NAME/KEY: Modified-site
            (B) LOCATION: 2..3

```
          (D) OTHER INFORMATION: /label= Linker
              /note= "Portion of the linker is
              CH2(4-pyridylacetyl)- and is used to link the
              second residue Arginine to the third residue (ix) FEATURE:
          (A) NAME/KEY: Modified-site
          (B) LOCATION: 15..16
          (D) OTHER INFORMATION: /label= Cha
              /note= "Cyclohexylalanine is included within the
              peptide chain between the 15th residue Alanine and
              the 16th residue Glutamic acid and is attached by (ix) FEATURE:
          (A) NAME/KEY: Modified-site
          (B) LOCATION: 16
          (D) OTHER INFORMATION: /label= D-configuration
              /note= "The 16th residue Glutamic acid is in the
              D-configuration."

(xi) SEQUENCE DESCRIPTION: SEQ ID NO:13:

Pro Arg Gly Gly Gly Gly Asp Tyr Glu Pro Ile Pro Glu Glu Ala Glu
1               5                   10                  15

NFORMATION FOR SEQ ID NO:14:

(i) SEQUENCE CHARACTERISTICS:
          (A) LENGTH: 17 amino acids
          (B) TYPE: amino acid
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION: /label= D-Cha
              /note= "Cyclohexylalanine in the D-configuration
              is attached to the N-terminal of the first residue
              Proline by peptide linkage."

(ix) FEATURE:
          (A) NAME/KEY: Modified-site
          (B) LOCATION: 2..3
          (D) OTHER INFORMATION: /label= Linker
              /note= "Portion of the linker is
              CH2(4-pyridylacetyl)- and is used to link the
              second residue Arginine to the third residue (xi) SEQUENCE DESCRIPTION: SEQ ID NO:14:

Pro Arg Gly Gly Gly Gly Asp Phe Glu Glu Ile Pro Glu Glu Tyr Leu
1               5                   10                  15
Gln (2) INFORMATION FOR SEQ ID NO:15:

(i) SEQUENCE CHARACTERISTICS:
          (A) LENGTH: 13 amino acids
          (B) TYPE: amino acid
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION: /label= D-Cha
              /note= "Cyclohexylalanine in the D-configuration
              is attached to the N-terminal of the first residue
              Proline by peptide linkage."

(ix) FEATURE:
          (A) NAME/KEY: Modified-site
          (B) LOCATION: 2..3
```

```
            (D) OTHER INFORMATION: /label= Linker
                /note= "Portion of the linker is
                CH2(4-pyridylacetyl)-(Abu) and is used to link the
                second residue Arginine to the third residue (ix) FEATURE:
            (A) NAME/KEY: Modified-site
            (B) LOCATION: 12..13
            (D) OTHER INFORMATION: /label= Cha
                /note= "Cyclohexylalanine is included within the
                peptide chain between the 12th residue Alanine and
                the 13th residue Glutamic acid and is attached by (ix) FEATURE:
            (A) NAME/KEY: Modified-site
            (B) LOCATION: 13
            (D) OTHER INFORMATION: /label= D-configuration
                /note= "The 13th residue Glutamic acid is in the
                D-configuration."

(xi) SEQUENCE DESCRIPTION: SEQ ID NO:15:

Pro Arg Gly Asp Tyr Glu Pro Ile Pro Glu Glu Ala Glu
1               5                   10

NFORMATION FOR SEQ ID NO:16:

(i) SEQUENCE CHARACTERISTICS:
            (A) LENGTH: 13 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= D-Cha
                /note= "Cyclohexylalanine in the D-configuration
                is attached to the N-terminal of the first residue
                Proline by peptide linkage."

(ix) FEATURE:
            (A) NAME/KEY: Modified-site
            (B) LOCATION: 2..3
            (D) OTHER INFORMATION: /label= Linker
                /note= "Portion of the linker is
                CH2(4-pyridylacetyl)-(Ava) and is used to link the
                second residue Arginine to the third residue (ix) FEATURE:
            (A) NAME/KEY: Modified-site
            (B) LOCATION: 12..13
            (D) OTHER INFORMATION: /label= Cha
                /note= "Cyclohexylalanine is included within the
                peptide chain between the 12th residue Alanine and
                the 13th residue Glutamic acid and is attached by (ix) FEATURE:
            (A) NAME/KEY: Modified-site
            (B) LOCATION: 13
            (D) OTHER INFORMATION: /label= D-configuration
                /note= "The 13th residue Glutamic acid is in the
                D-configuration."

(xi) SEQUENCE DESCRIPTION: SEQ ID NO:16:

Pro Arg Gly Asp Tyr Glu Pro Ile Pro Glu Glu Ala Glu
1               5                   10

NFORMATION FOR SEQ ID NO:17:

(i) SEQUENCE CHARACTERISTICS:
            (A) LENGTH: 13 amino acids
            (B) TYPE: amino acid
            (D) TOPOLOGY: unknown
```

(ii) MOLECULE TYPE: peptide (ix) FEATURE:
              (A) NAME/KEY: Modified-site
              (B) LOCATION: 1
              (D) OTHER INFORMATION: /label= D-Cha
                  /note= "Cyclohexylalanine in the D-configuration
                  is attached to the N-terminal of the first residue
                  Proline by peptide linkage."

(ix) FEATURE:
              (A) NAME/KEY: Modified-site
              (B) LOCATION: 2..3
              (D) OTHER INFORMATION: /label= Linker
                  /note= "Portion of the linker is
                  CH2(4-pyridylacetyl)-(Aca) and is used to link the
                  second residue Arginine to the third residue (ix) FEATURE:
              (A) NAME/KEY: Modified-site
              (B) LOCATION: 12..13
              (D) OTHER INFORMATION: /label= Cha
                  /note= "Cyclohexylalanine is included within the
                  peptide chain between the 12th residue Alanine and
                  the 13th residue Glutamic acid and is attached by (ix) FEATURE:
              (A) NAME/KEY: Modified-site
              (B) LOCATION: 13
              (D) OTHER INFORMATION: /label= D-configuration
                  /note= "The 13th residue Glutamic acid is in the
                  D-configuration."

(xi) SEQUENCE DESCRIPTION: SEQ ID NO:17:

Pro Arg Gly Asp Tyr Glu Pro Ile Pro Glu Glu Ala Glu
1               5                   10

NFORMATION FOR SEQ ID NO:18:

(i) SEQUENCE CHARACTERISTICS:
              (A) LENGTH: 13 amino acids
              (B) TYPE: amino acid
              (D) TOPOLOGY: unknown (ii) MOLECULE TYPE: peptide (ix) FEATURE:
              (A) NAME/KEY: Modified-site
              (B) LOCATION: 1
              (D) OTHER INFORMATION: /label= D-Cha
                  /note= "Cyclohexylalanine in the D-configuration
                  is attached to the N-terminal of the first residue
                  Proline by peptide linkage."

(ix) FEATURE:
              (A) NAME/KEY: Modified-site
              (B) LOCATION: 2..3
              (D) OTHER INFORMATION: /label= Linker
                  /note= "Portion of the linker is
                  CH2(4-pyridylacetyl)-(Aha) and is used to link the
                  second residue Arginine to the third residue (ix) FEATURE:
              (A) NAME/KEY: Modified-site
              (B) LOCATION: 12..13
              (D) OTHER INFORMATION: /label= Cha
                  /note= "Cyclohexylalanine is included within the
                  peptide chain between the 12th residue Alanine and
                  the 13th residue Glutamic acid and is attached by (ix) FEATURE:
              (A) NAME/KEY: Modified-site
              (B) LOCATION: 13
              (D) OTHER INFORMATION: /label= D-configuration
                  /note= "The 13th residue Glutamic acid is in the
                  D-configuration."

-continued (xi) SEQUENCE DESCRIPTION: SEQ ID NO:18:

Pro Arg Gly Asp Tyr Glu Pro Ile Pro Glu Glu Ala Glu
1               5                  10

NFORMATION FOR SEQ ID NO:19:

(i) SEQUENCE CHARACTERISTICS:
            (A) LENGTH: 16 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= D-Cha
                /note= "Cyclohexylalanine in the D-configuration
                is attached to the N-terminal of the first residue
                Proline by peptide linkage."

(ix) FEATURE:
            (A) NAME/KEY: Modified-site
            (B) LOCATION: 2..3
            (D) OTHER INFORMATION: /label= Linker
                /note= "Portion of the linker is
                CH2(4-pyridylacetyl) and is used to link the
                second residue Arginine to the third residue (ix) FEATURE:
            (A) NAME/KEY: Modified-site
            (B) LOCATION: 15..16
            (D) OTHER INFORMATION: /label= Cha
                /note= "Cyclohexylalanine is included within the
                peptide chain between the 15th residue Alanine and
                the 16th residue Glutamic acid by peptide (ix) FEATURE:
            (A) NAME/KEY: Modified-site
            (B) LOCATION: 16
            (D) OTHER INFORMATION: /label= D-configuration
                /note= "The 16th residue Glutamic acid is in the
                D-configuration."

(xi) SEQUENCE DESCRIPTION: SEQ ID NO:19:

Pro Arg Gly Gly Gly Gly Asp Tyr Glu Pro Ile Pro Glu Glu Ala Glu
1               5                  10                  15

NFORMATION FOR SEQ ID NO:20:

(i) SEQUENCE CHARACTERISTICS:
            (A) LENGTH: 18 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= D-configuration
                /note= "The first residue Phenylalanine is in the
                D-configuration."

(ix) FEATURE:
            (A) NAME/KEY: Modified-site
            (B) LOCATION: 3..4
            (D) OTHER INFORMATION: /label= Linker
                /note= "Portion of the linker is CH2SCH2CO and is
                used to link the third residue Arginine to the
                fourth residue Glycine. "

(xi) SEQUENCE DESCRIPTION: SEQ ID NO:20:

Phe Pro Arg Gly Gly Gly Gly Asp Phe Glu Glu Pro Ile Glu Glu Tyr
1               5                   10                  15

Leu Gln (2) INFORMATION FOR SEQ ID NO:21:

(i) SEQUENCE CHARACTERISTICS:
          (A) LENGTH: 18 amino acids
          (B) TYPE: amino acid
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION: /label= Acetyl-D-config
              /note= "An acetyl group is attached to the
              N-terminal of the first residue Phenylalanine
              which is in the D-configuration."

(ix) FEATURE:
          (A) NAME/KEY: Modified-site
          (B) LOCATION: 3..4
          (D) OTHER INFORMATION: /label= Linker
              /note= "Portion of the linker is CH2SCH2CO and is
              used to link the third residue Arginine to the
              fourth residue Glycine. "

(xi) SEQUENCE DESCRIPTION: SEQ ID NO:21:

Phe Pro Arg Gly Gly Gly Gly Asp Phe Glu Glu Ile Pro Glu Glu Tyr
1               5                   10                  15

Leu Gln (2) INFORMATION FOR SEQ ID NO:22:

(i) SEQUENCE CHARACTERISTICS:
          (A) LENGTH: 13 amino acids
          (B) TYPE: amino acid
          (D) TOPOLOGY: unknown (ii) MOLECULE TYPE: peptide (ix) FEATURE:
          (A) NAME/KEY: Modified-site
          (B) LOCATION: 1
          (D) OTHER INFORMATION: /label= D-Cha
              /note= "Cyclohexylalanine in the D-configuration
              is attached to the N-terminal of the first residue
              Proline through a peptide linkage."

(ix) FEATURE:
          (A) NAME/KEY: Modified-site
          (B) LOCATION: 2..3
          (D) OTHER INFORMATION: /label= Linker
              /note= "Portion of the linker is
              CH2-(4-pyridylacetyl)-NH(CH2)2CO- and is used to
              link the second residue Arginine to the third (ix) FEATURE:
          (A) NAME/KEY: Modified-site
          (B) LOCATION: 12..13
          (D) OTHER INFORMATION: /label= Cha
              /note= "Cyclohexylalanine is included within the
              peptide chain between the 12th residue Alanine and
              13th residue Glutamic acid and is attached by (ix) FEATURE:
          (A) NAME/KEY: Modified-site
          (B) LOCATION: 13

```
            (D) OTHER INFORMATION: /label= D-configuration
                /note= "The 13th residue Glutamic acid is in the
                D-configuration."

(xi) SEQUENCE DESCRIPTION: SEQ ID NO:22:

Pro Arg Gly Asp Tyr Glu Pro Ile Pro Glu Glu Ala Glu
1               5                   10

NFORMATION FOR SEQ ID NO:23:

(i) SEQUENCE CHARACTERISTICS:
        (A) LENGTH: 14 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= D-Cha
                /note= "Cyclohexylalanine in the D-configuration
                is attached to the N-terminal of the first residue
                Proline through peptide linkage."

(ix) FEATURE:
        (A) NAME/KEY: Modified-site
        (B) LOCATION: 2..3
        (D) OTHER INFORMATION: /label= Linker
                /note= "Portion of the linker is
                CH2-(4-pyridylacetyl) and is used to link the
                second residue Arginine to the third residue (ix) FEATURE:
        (A) NAME/KEY: Modified-site
        (B) LOCATION: 13..14
        (D) OTHER INFORMATION: /label= Cha
                /note= "Cyclohexylalanine is included within the
                peptide chain between the 13th residue Alanine and
                the 14th residue Glutamic acid and is attached by (ix) FEATURE:
        (A) NAME/KEY: Modified-site
        (B) LOCATION: 14
        (D) OTHER INFORMATION: /label= D-configuration
                /note= "The 14th residue Glutamic acid is in the
                D-configuration."

(xi) SEQUENCE DESCRIPTION: SEQ ID NO:23:

Pro Arg Gly Gly Asp Tyr Glu Pro Ile Pro Glu Glu Ala Glu
1               5                   10

NFORMATION FOR SEQ ID NO:24:

(i) SEQUENCE CHARACTERISTICS:
        (A) LENGTH: 12 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= D-Cha
                /note= "Cyclohexylalanine in the D-configuration
                is attached to the N-temrinal of the first residue
                Proline through peptide linkage."

(ix) FEATURE:
        (A) NAME/KEY: Modified-site
        (B) LOCATION: 2..3
```

```
            (D) OTHER INFORMATION: /label= Linker
                /note= "Portion of the linker is
                CH2-(4-pyridylacetyl)-NH(CH2)3CO- and is used to
                link the second residue Arginine to the third (ix) FEATURE:
            (A) NAME/KEY: Modified-site
            (B) LOCATION: 11..12
            (D) OTHER INFORMATION: /label= Cha
                /note= "Cyclohexylalanine is included within the
                peptide chain between the 11th residue Alanine and
                12th residue Glutamic acid and is attached by (ix) FEATURE:
            (A) NAME/KEY: Modified-site
            (B) LOCATION: 12
            (D) OTHER INFORMATION: /label= D-configuration
                /note= "The 12th residue Glutamic acid is in the
                D-configuration."

(xi) SEQUENCE DESCRIPTION: SEQ ID NO:24:

Pro Arg Asp Tyr Glu Pro Ile Pro Glu Glu Ala Glu
1               5                   10

NFORMATION FOR SEQ ID NO:25:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= D-Cha
                /note= "Cyclohexylalanine in the D-configuration
                is attached to the N-terminal of the first residue
                Proline through a peptide linkage."

(ix) FEATURE:
            (A) NAME/KEY: Modified-site
            (B) LOCATION: 2..3
            (D) OTHER INFORMATION: /label= Linker
                /note= "Portion of the linker is
                CH2-(4-pyridylacetyl)-NH(CH2)2CO- and is used to
                link the second residue Arginine to the third (ix) FEATURE:
            (A) NAME/KEY: Modified-site
            (B) LOCATION: 11..12
            (D) OTHER INFORMATION: /label= Cha
                /note= "Cyclohexylalanine is included within the
                peptide chain between the 11th residue Alanine and
                the 12th residue Glutamic acid and is attached by (ix) FEATURE:
            (A) NAME/KEY: Modified-site
            (B) LOCATION: 12
            (D) OTHER INFORMATION: /label= D-configuration
                /note= "The 12th residue Glutamic acid is in the
                D-configuration."

(xi) SEQUENCE DESCRIPTION: SEQ ID NO:25:

Pro Arg Asp Tyr Glu Pro Ile Pro Glu Glu Ala Glu
1               5                   10

NFORMATION FOR SEQ ID NO:26:

(i) SEQUENCE CHARACTERISTICS:
            (A) LENGTH: 19 amino acids
            (B) TYPE: amino acid
            (D) TOPOLOGY: unknown
```

```
       (ii) MOLECULE TYPE: peptide (ix) FEATURE:
            (A) NAME/KEY: Modified-site
            (B) LOCATION: 1
            (D) OTHER INFORMATION: /label= Acetyl-D-config
                /note= "An acetyl group is attached to the
                N-terminal of the first residue Phenylalanine
                which is in the D-configuration."

(ix) FEATURE:
            (A) NAME/KEY: Modified-site
            (B) LOCATION: 3..4
            (D) OTHER INFORMATION: /label= Linker
                /note= "Portion of the linker is -(CH2)2CO- and is
                used to link the third residue Arginine to the
                fourth residue Glutamine. "

(ix) FEATURE:
            (A) NAME/KEY: Modified-site
            (B) LOCATION: 18..19
            (D) OTHER INFORMATION: /label= Cha
                /note= "Cyclohexylalanine is included within the
                peptide chain between the 18th residue Tyrosine
                and 19th residue Glutamine and is attached by (xi) SEQUENCE DESCRIPTION: SEQ ID NO:26:

Phe Pro Arg Gln Ser His Asn Asp Gly Asp Phe Glu Pro Ile Pro Glu
1               5                   10                  15

Glu Tyr Gln (2) INFORMATION FOR SEQ ID NO:27:

(i) SEQUENCE CHARACTERISTICS:
            (A) LENGTH: 10 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= Acetyl-D-config
                /note= "An acetyl group is attached to
                theN-terminal of the first residue Phenylalanine
                which is in the D-configuration."

(ix) FEATURE:
            (A) NAME/KEY: Modified-site
            (B) LOCATION: 3..4
            (D) OTHER INFORMATION: /label= Linker
                /note= "Portion of the linker is
                -(CH2)4CO-[NH-CH2-CH=CH-CH2-CO]2- and is used to
                link the third residue Arginine to the fourth (xi) SEQUENCE DESCRIPTION: SEQ ID NO:27:

Phe Pro Arg Asp Glu Phe Pro Ile Pro Tyr
1               5                   10

NFORMATION FOR SEQ ID NO:28:

(i) SEQUENCE CHARACTERISTICS:
            (A) LENGTH: 20 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
```

(D) OTHER INFORMATION: /label= succinyl
                /note= "Succinyl is attached to the N-terminal of
                the first residue Phenylalanine which is in the
                D-configuration."

(ix) FEATURE:
            (A) NAME/KEY: Modified-site
            (B) LOCATION: 3..4
            (D) OTHER INFORMATION: /label= Linker
                /note= "Portion of the linker is -(CH2)2CO- and is
                used to link the third residue Arginine to the
                fourth residue Glutamine."

(xi) SEQUENCE DESCRIPTION: SEQ ID NO:28:

Phe Pro Arg Gln Ser His Asn Asp Gly Asp Phe Glu Glu Ile Pro Glu
1               5                   10                  15

Glu Tyr Leu Gln
            20

(2) INFORMATION FOR SEQ ID NO:29:

(i) SEQUENCE CHARACTERISTICS:
            (A) LENGTH: 10 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= Acetyl-D-config
                /note= "An acetyl group is attached to the
                N-terminal of the first residue Phenylalanine
                which is in the D-configuration."

(ix) FEATURE:
            (A) NAME/KEY: Modified-site
            (B) LOCATION: 3..4
            (D) OTHER INFORMATION: /label= Linker
                /note= "Portion of the linker is
                -(CH2)4CO-[NH(CH2)4(CO)]2 and is used to link the
                third residue Arginine to the fourth residue (xi) SEQUENCE DESCRIPTION: SEQ ID NO:29:

Phe Pro Arg Asp Phe Glu Pro Ile Pro Leu
1               5                   10

NFORMATION FOR SEQ ID NO:30:

(i) SEQUENCE CHARACTERISTICS:
            (A) LENGTH: 12 amino acids
            (B) TYPE: amino acid
            (D) TOPOLOGY: unknown (ii) MOLECULE TYPE: peptide (ix) FEATURE:
            (A) NAME/KEY: Modified-site
            (B) LOCATION: 1
            (D) OTHER INFORMATION: /label= Acetyl-D-config
                /note= "An alpha-N-acetyl group is attached to the
                N-terminal of the first residue Phenylalanine
                which is in the D-configuration."

(ix) FEATURE:
            (A) NAME/KEY: Modified-site
            (B) LOCATION: 3..4
            (D) OTHER INFORMATION: /label= Linker
                /note= "Portion of the linker is
                -(CH2)4(CO)-[NH(CH2)4(CO)] and is used to link the
                third residue Arginine to the fourth residue (xi) SEQUENCE DESCRIPTION: SEQ ID NO:30:

Phe Pro Arg Asn Gly Asp Phe Glu Pro Ile Pro Leu
1               5                   10

NFORMATION FOR SEQ ID NO:31:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= D-config
            /note= "The first residue Phenylalanine is in the
            D-configuration."

(ix) FEATURE:
        (A) NAME/KEY: Modified-site
        (B) LOCATION: 3..4
        (D) OTHER INFORMATION: /label= Linker
            /note= "Portion of the linker is
            -(CH2)4(CO)-[NH(CH2)4(CO)]2 and is used to link
            the third residue Arginine to the fourth residue (ix) FEATURE:
        (A) NAME/KEY: Modified-site
        (B) LOCATION: 6
        (D) OTHER INFORMATION: /label= thiahomoGlu
            /note= "The sixth residue Glutamic acid is
            substituted to become thiahomoG..."

(xi) SEQUENCE DESCRIPTION: SEQ ID NO:31:

Phe Pro Arg Asp Phe Glu Pro Ile Pro Leu
1               5                   10

NFORMATION FOR SEQ ID NO:32:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= D-config
            /note= "The first residue Phenylalanine is in the
            D-configuration."

(ix) FEATURE:
        (A) NAME/KEY: Modified-site
        (B) LOCATION: 3..4
        (D) OTHER INFORMATION: /label= Linker
            /note= "Portion of the linker is
            -(CH2)4(CO)-[NH(CH2)4(CO)]2 and is used to link
            the third residue Arginine to the fourth residue (xi) SEQUENCE DESCRIPTION: SEQ ID NO:32:

Phe Pro Arg Asp Phe Glu Pro Ile Pro Leu
1               5                   10

```
(2) INFORMATION FOR SEQ ID NO:33:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 1
        (D) OTHER INFORMATION: /label= D-config
            /note= "The first residue Phenylalanine is in the
            D-configuration."

(ix) FEATURE:
        (A) NAME/KEY: Modified-site
        (B) LOCATION: 3..4
        (D) OTHER INFORMATION: /label= Linker
            /note= "Portion of the linker is
            -(CH2)4(CO)-[NH(CH2)4(CO)]2 and is used to link
            the third residue Arginine to the fourth residue (xi) SEQUENCE DESCRIPTION: SEQ ID NO:33:

Phe Pro Arg Phe Glu Pro Ile Pro Leu
1               5
```

We claim:

1. A thrombin inhibitor of formula (I)

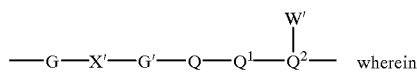

and pharmaceutically acceptable salts thereof wherein

AS is a hydrophobic moiety which binds the catalytic site of thrombin, said hydrophobic moiety comprising (a) one or two hydrophobic α-amino acids, which are optionally substituted by a lower alkyl, aryl or aralkyl, and (b) a guanidino group;

Y is (CO), —CH$_2$—, or —CH$_2$OH;

Z is a divalent, straight chained linker moiety that has a chain length of at least about 10 atoms to about 85 atoms; and A is an acidic portion of formula (III)

wherein

G and G' are the same or different and are an L-α-amino acid having a pk value of about 5 or below;

X' is a hydrophobic L-α-amino acid;

Q is an L-α-amino acid or a cyclic L-imino acid;

Q$^1$ and Q$^2$ are different and are either Ile or Pro;

W is H, or a branched or straight chain alkyl, aryl or aralkyl radical, with the proviso that W' is linked to whichever of Q$^1$ or Q$^2$ is Pro;

R is selected from the group consisting of a hydrophobic amino acid; an alkyl, aryl or aralkyl radical, optionally substituted by a carboxyl or amide function; Leu-R'; Glu-Glu-Ala-R'; Glu-Glu-Tyr-Leu-Gln-OH;

Glu-Glu-Phe-Leu-R'; and J

Glu-Glu-Phe-Leu-Glx-R' J wherein

J is H, OH, O—SO$_2$—OH, —CH$_2$—SO$_2$—OH or —O—PO$_2$—OH, or —CH$_2$—PO$_2$—OH substituted at the para position of the phenyl ring, or R and R' are the same or different and are a hydroxyl group, an amino acid or an amine group having the following formula (IV):

$$-\text{N}\begin{matrix}R_2\\R_3\end{matrix}\qquad\qquad (IV)$$

wherein R$_2$ and R$_3$ are each independently hydrogen, lower alkyl, aryl or alkoxyalkyl, and may be joined to form a ring of 5–6 members, which ring can optionally contain an additional heteroatom selected from the group consisting of O, S and NH and wherein, with the proviso that A is at least six amino acids in length, any one of G, G', X' and Q optionally are absent;

and pharmaceutically acceptable salts thereof.

2. A thrombin inhibitor according to claim 1, wherein Y is carbonyl.

3. A thrombin inhibitor according to claim 2, wherein Z is a divalent linker moiety composed of a carbon chain that is interrupted by one or more O, S, or NH, and can be substituted by one or more substituents selected from the group consisting of alkyl, alkoxy, alkoxyalkyl, aryl, and aralkyl groups that can in turn be substituted by amide, hydroxy, imidazol, carboxy, or halogen groups, the terminal atom of the chain being a carbon atom that is part of a carbonyl group that forms a peptide linkage with said acidic portion A and with the proviso that the initial atom of the chain is not a nitrogen atom forming a peptide bond with said Y.

4. A thrombin inhibitor according to claim 3, wherein Z is

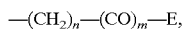 (II)

wherein m is 0 or 1, n is an integer ranging from 0 to 4,

E is a carbon chain that is interrupted by one or more O, S, or NH, and can be substituted by one or more substituents selected from the group consisting of alkyl, alkoxy, alkoxyalkyl, aryl, and aralkyl groups that can in turn be substituted by amide, hydroxy, imidazol, carboxy, or halogen groups, the terminal atom of the chain being a carbon atom that is part of a carbonyl group that forms a peptide linkage with said acidic portion A.

5. A thrombin inhibitor according to claim 4, wherein E is the native hirudin[49-54] sequence or analogs thereof.

6. A thrombin inhibitor according to claim 4, wherein E is selected from the group consisting of -Gln-Ser-His-Asn-Asp-Gly-, -Gly-Ser-His-Asn-Asp-Gly-, -[5-aminovaleryl]$_{1-2}$, and (Gly)$_4$.

7. A thrombin inhibitor according to claim 3, wherein Z is $(CH_2)_{2-4}(CO)$-Gln-Ser-His-Asn-Asp-Gly-.

8. A thrombin inhibitor according to claim 7, wherein Z is $(CH_2)_2(CO)$-Gln-Ser-His-Asn-Asp-Gly-.

9. A thrombin inhibitor according to claim 7, wherein Z is $(CH_2)_3(CO)$-Gln-Ser-His-Asn-Asp-Gly-.

10. A thrombin inhibitor according to claim 7, wherein Z is selected from the group consisting of $(CH_2)_4(CO)$-Gln-Ser-His-Asn-Asp-Gly-.

11. A thrombin inhibitor according to claim 4, wherein E is a synthetic spanner of the general formula (III):

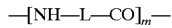 (III)

wherein m is an integer ranging from 1 to 4, and L is a hexapeptide, or saturated or unsaturated alkyl chain corresponding to 18 atoms or less.

12. A thrombin inhibitor according to claim 11, wherein L is —$(CH_{0-2})_n$—, wherein n is an integer ranging from 1 to 4.

13. A thrombin inhibitor according to claim 12, wherein L is —$(CH_{0-2})_4$—.

14. A thrombin inhibitor according to claim 13, wherein L is —$CH_2$—$CH_2$—$CH_2$—$CH_2$—.

15. A thrombin inhibitor according to claim 13, wherein L is —$CH_2$—$CH$=$CH$—$CH_2$—.

16. A thrombin inhibitor according to claim 4, wherein Z is $(CH_2)_4CO$—$[NH$—$CH_2$—$CH$=$CH$—$CH_2$—$CO]_{1-3}$.

17. A thrombin inhibitor according to claim 4, wherein Z is $(CH_2)_4CO$—$[NH$—$CH_2$—$CH$=$CH$—$CH_2$—$CO]_1$.

18. A thrombin inhibitor according to claim 4, wherein Z is $(CH_2)_4CO$—$[NH$—$CH_2$—$CH$=$CH$—$CH_2$—$CO]_2$.

19. A thrombin inhibitor according to claim 4, wherein Z is $(CH_2)_4CO$—$[NH$—$CH_2$—$CH$=$CH$—$CH_2$—$CO]_3$.

20. A thrombin inhibitor according to claim 4, wherein E is a carbon chain interrupted by O, NH, or S, and can be substituted by one or more substituents selected from the group consisting of alkyl, alkoxy, and alkoxyalkyl groups that can be substituted in turn by amide, hydroxy, imidazol, carboxy, or halogen groups, wherein said alkyl, alkoxy, and alkoxyalkyl groups can join the carbon chain at two points to form an aromatic or non-aromatic ring within the carbon chain.

21. A thrombin inhibitor according to claim 20, wherein E is pyridylacetyl-$R^{15}$ wherein $R^{15}$ is 1–4 amino acids.

22. A thrombin inhibitor according to claim 21, wherein E is 4-pyridylacetyl-$(R^{20})_{0-1}$-$R^{30}$ wherein $R^{20}$, if present, is a linker of formula (III), —$[NH$—$L$—$CO]_m$—, wherein m is 1–6 and $R^{30}$ is $(Gly)_{1-4}$.

23. A thrombin inhibitor according to claim 22, wherein $R^{20}$ is not present, and $R^{30}$ is $(Gly)_{2-4}$.

24. A thrombin inhibitor according to claim 1 or 2 wherein said AS portion is:

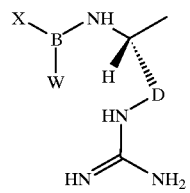 (IV)

wherein

X is a hydrophobic group;

B is a residue of a hydrophobic amino acid;

W is H or a branched or straight chained alkyl, aryl, or aralkyl radical;

D is ρ-phenylmethyl, ρ-phenylethyl, or a linear carbon chain having 2 to 4 carbon atoms which can be substituted by lower alkyl.

25. A thrombin inhibitor according to claim 24, wherein X is a hydrophobic α-amino acid in the D-configuration, attached by a peptide linkage to B.

26. A thrombin inhibitor according to claim 25, wherein X is D-Phe, D-4FPhe or D-4ClPhe wherein the α-amino group is neutralized by acetylation or benzoylation.

27. A thrombin inhibitor according to claim 24, wherein B is a residue of a hydrophobic α-amino acid of the L-configuration or a cyclic imino acid which can bear one or more alkyl substituents attached to the ring, wherein said substituents may bridge to form a cyclic structure;

D is ρ-phenylmethyl, ρ-phenylethyl, ethylene, butylene, or propylene;

W is hydrogen or a lower alkyl, aryl, or aralkyl substituent.

28. A thrombin inhibitor according to claim 27 wherein B contains a piperidine or pyrrolidine ring; and W is H or a lower alkyl, aryl, or aralkyl substituent on the 3, 4 or 5 position of the piperidine or pyrrolidine ring of B.

29. A thrombin inhibitor according to claim 1, wherein

X is D-Phe, D-4FPhe or D-4ClPhe;

B is valine, pipecolic acid, or proline;

W is hydrogen or a lower alkyl, aryl, or aralkyl substituent and may be substituted on the 3, 4, or 5 position of the ring when B is proline or pipecolic acid;

D is propylene or ρ-phenylmethyl.

30. A thrombin inhibitor according to claim 28, wherein

X is D-Phe,

B is Pro, and

D is propylene.

31. A thrombin inhibitor according to claim 1 wherein G, G', X', and Q are present, $Q^1$ is Ile and $Q^2$ is Pro.

32. A thrombin inhibitor according to claim 1, wherein G and G' are independently Asp, Glu,

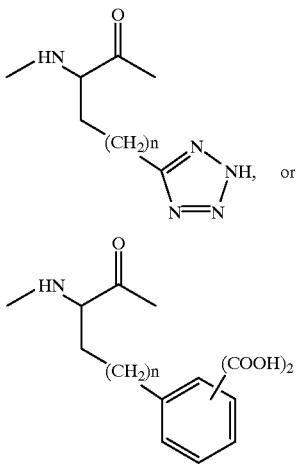

wherein
n is 0 to 2,
X' is L-Phe, L-4FPhe, or L-4ClPhe, Phe, Glu, or Tyr;
Q is proline, pipecolic acid, sarcosine, or glutamic acid;
R is selected from the group consisting of

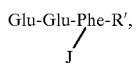

wherein J is H, or OH, substituted at the para position of the phenyl ring;
R' is hydroxyl radical of the COOH terminus of the preceding amino acid, a group comprising 1 to 2 amino acid, or an amine group having the following formula:

wherein $R_2$ and $R_3$ are each independently hydrogen, lower alkyl, aryl, or alkoxyalkyl, or may be joined to form a ring of 5–6 members, which ring can optionally contain an additional heteroatom selected from O, S, and NH, or pharmaceutically acceptable salts thereof.

33. A thrombin inhibitor according to claim 32, wherein
G and G' are independently Asp, or Glu;
X' is Phe;
Q is proline, pipecolic acid, or Glu;
R is selected from the group consisting of

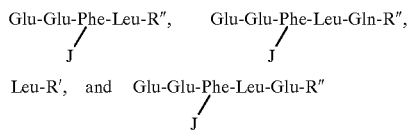

wherein J is H, or OH, substituted at the para position of the phenyl ring;
R' and R" are hydroxyl radical of the COOH terminus of the preceding amino acid, any amino acid, or an amine group having the following formula:

wherein $R_2$ and $R_3$ are each independently hydrogen, lower alkyl, aryl, or alkoxyalkyl, or may be joined to form a ring of 5–6 members, which ring can optionally contain an additional heteroatom selected from the group consisting of O, S, and NH, or pharmaceutically acceptable salts thereof.

34. A thrombin inhibitor according to claim 1, wherein
G is Asp,
G' is Glu,
X' is Phe,
Q is Glu or Pro,
W' is H, n-butyl, or methyl, and
R is Leu-R',

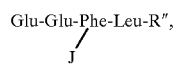

wherein J is H, or OH, substituted at the para position of the phenyl ring, and
R' and R" are a hydroxyl radical of the COOH terminus of the preceding amino acid, any amino acid, or an amine group or pharmaceutically acceptable salts thereof.

35. A thrombin inhibitor according to claim 34, wherein R is Glu-Glu-Tyr-Leu-Gln-OH, or Leu-OH, or Glu-Glu-Tyr-Leu-OH.

36. A thrombin inhibitor according to claim 34, wherein R is Glu-Glu-Tyr-Leu-Gln-OH, or Leu-OH.

37. A peptide derivative having the following formula VI:

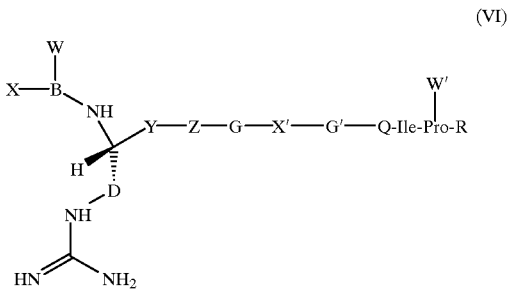

(VI)

wherein
X is a hydrophobic group;
B is a residue of a hydrophobic amino acid;
W is H, or a branched or straight chain alkyl, aryl or aralkyl radical;
D is a linear carbon chain having 2 to 4 carbon atoms which can be substituted by lower alkyl, or D is a p-phenylmethyl or a p-phenylethyl group;
Y is carbonyl, hydroxymethyl of either D or L configuration or —$CH_2$—;
Z is a divalent straight chained link moiety that having a chain length of at least about 10 atoms, in the case where Y is carbonyl or hydroxymethyl, the atom adjacent to the carbon atom of Y may be unsubstituted or mono- or di-fluoro-substituted, and Z can be composed of a carbon chain that is interrupted by one or more O, S, NH, carbonyl, ester or amide groups and can be substituted by one or more substituents selected from alkyl, alkoxy, alkoxyalkyl, aryl and aralkyl groups that can in turn be substituted by amide, hydroxy, imidazol, carboxy or halogen groups, the terminal atom of the chain being a carbon atom that is part of a carbonyl group that forms a peptide linkage with the L-α-amino acid G.

G and G' are the same or different and are an L-α-amino acid having a pk value of about 5 or below;

X' is a hydrophobic L-α-amino acid;

Q is a residue of a L-α-amino acid or a cyclic L-imino acid;

W' is H, or a branched or straight chain alkyl, aryl or aralkyl radical;

R is a hydrophobic group comprising 1 to 5 amino acids or an alkyl, aryl, or aralkyl radical which can be substituted by a carboxyl or amide function or, R is Glu-Glu-Phe-Leu-R', Glu-Glu-Phe-Leu-Gln-R', or
            /J                 /J Glu-Glu-Phe-Leu-Glu-R', wherein J is H, OH,
/J

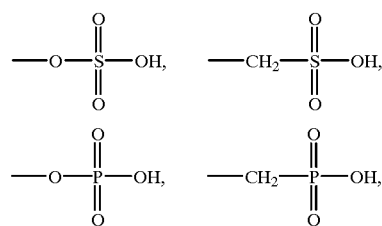

substituted at the para position of the phenyl ring; or

R and R' are the same or different and are an amino acid or an amine group having the following formula:

wherein $R_2$ and $R_3$ are each independently hydrogen, lower alkyl, aryl or alkoxyalkyl, and may be joined to form a ring of 5–6 members, which ring can optionally contain an additional heteroatom selected from O, S, and NH, and pharmaceutically acceptable salts thereof, or R' is a hydroxyl group attached to Leu to form a carboxyl group, or a therapeutically acceptable salt thereof.

38. A peptide according to claim 37, wherein

X is a hydrophobic α-amino acid in the D-configuration, attached by a peptide linkage to substituent B or a hydrophobic group attached to the nitrogen atom of substituent B;

B is a residue of a hydrophobic α-amino acid or the L-configuration or a cyclic imino acid, which can bear one or more alkyl substituents attached to the ring, which substituents may bridge to form a cyclic structure;

W is H or a lower alkyl, aryl or aralkyl substituent on the 3, 4, or 5 position of the piperidine or pyrrolidine ring;

D is p-phenylmethyl, p-phenylethyl, ethylene, butylene, or propylene;

Y is carbonyl;

Z has a chain length between 12 and 40 and preferably 20 atoms;

G and G' are the same or different and are Asp, Glu,

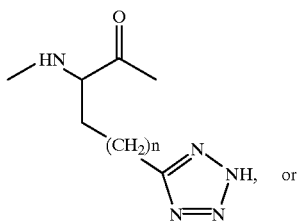

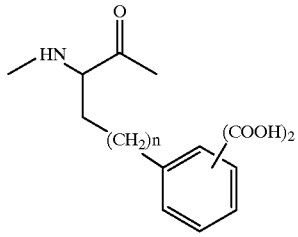

wherein n is 1 or 2,

X' is L-phe, L4FPhe or L-4ClPhe;

Q is proline, pipecolic acid, sarcosine or Glu;

W' is H or a lower alkyl, aryl or aralkyl substituent on the 3, 4 or 5 position of the piperidine or pyrrolidine ring;

W' is H or a lower alkyl, aryl or aralkyl substituent on the 3, 4 or 5 position of the piperidine or pyrrolidine ring;

R is Glu-Glu-Phe-Leu-R',
                 /J

J is H, OH,

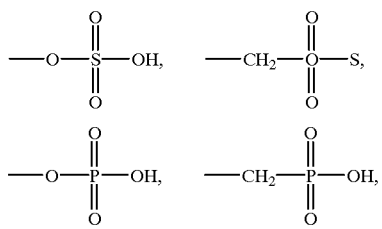

substituted in the para position
and R' is a hydroxyl group or

wherein $R_2$ and $R_3$ are straight chain or branched alkyl chains having 1 to 6 carbon atoms and may be joined to form a ring of 5–6 members.

39. A peptide according to claim 37, wherein

X is D-Phe, D-4FPhe or D-4ClPhe wherein the α-amino group is neutralized by acetylation or benzoylation, or X is naphthalenesulfonyl, benzenesulfonyl, toluene-sulfonyl;

B is Val, pipecolic acid or Pro;

W is hydrogen or a lower alkyl, aryl or aralkyl substituent on the 3,4 or 5 position of the piperidine or pyrrolidine ring;

D is propylene of the ring when B is Pro or pipecolic acid or phenylmethyl;

Y is carbonyl;

Z is

wherein n is an integer ranging from 1 to 4, the native hirudin48–54 sequence, or a synthetic spanner of the general formula

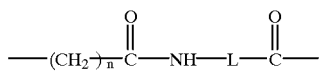

wherein n is an integer ranging from 1 to 4; and

L is a hexapeptide or saturated or unsaturated alkyl chain corresponding to 18 atoms or less of a hexapeptide;

R is Glu-Glu-Tyr-Leu-Gln-OH, Leu-OH or Glu-Glu-Tyr-Leu-R' wherein R' is a hydroxyl group or a group having the following formula:

wherein $R_2$ is —$CH_3$ or phenylethyl, $R_3$ is H or —$CH_3$ or $R_2$ and $R_3$ may be joined together to form —$CH_2$—$CH_2$—$CH_2$—$CH_2$—, —$CH_2$—$CH_2$—$CH_2$—$CH_2$—$CH_2$—$CH_2$— or —$CH_2$—$CH_2$—O—$CH_2$—$CH_2$—.

40. A compound according to claim 3 selected from the group consisting of:

P79 (SEQ ID NO:1) (BCH-1709): Ac(D-Phe)-Pro-Arg-$(CH_2)_2$(CO)-QSHNDGDFEEIPEEYLQ-OH;

P102 (SEQ ID NO:2): Ac(D-Phe)-Pro-Arg-$(CH_2)_3$(CO)-QSHNDGDFEEIPEEYLQ-OH;

P103 (SEQ ID NO:3): Ac(D-Phe)-Pro-Arg-$(CH_2)_4$(CO)-QSHNDGDFEEIPEEYLQ-OH;

P109 (SEQ ID NO:4): Ac(D-Phe)-Pro-Arg-$CH_2$(CO)-GSHNDGDFEEIPEEYLQ-OH;

P183 (SEQ ID NO:5): Ac(D-Phe)-Pro-Arg-$(CH_2)_4$(CO)—[NH—$CH_2$—CH=CH—$CH_2$—(CO)]-DFEPIPL-OH;

P184 (SEQ ID NO:6) (BCH-1710): Ac(D-Phe)-Pro-Arg-$(CH_2)_4$(CO)—[NH—$CH_2$—CH=CH—$CH_2$—(CO)]$_2$-DFEPIPL-OH;

P185 (SEQ ID NO:7): Ac(D-Phe)-Pro-Arg-$(CH_2)_4$(CO)—[NH—$CH_2$—CH=CH—$CH_2$—(CO)]$_3$-DFEPIPL-OH;

P290 (SEQ ID NO:8) (BCH-1719): Ac(D-Phe)-thioPro-Arg-$(CH_2)_2$(CO)-QSHNDGDFEEIPEEYLQ-OH;

P311 (SEQ ID NO:9) (BCH-1721): Ac(D-Cha)-Pro-Arg-$(CH_2)_2$(CO)-QSHNDGDFEEIPEEYLQ-OH;

P314 (SEQ ID NO:10) (BCH-1726): Ac(D-Cha)-Pro-Arg-$(CH_2)_2$(CO)-QSHNDGDFEPIPEEY-(Cha)-Q-OH;

P536 (SEQ ID NO:11): (D-Cha)-Pro-Arg-$CH_2$N(COCH$_3$) $CH_2$(CO)-(Gly)$_4$-DYEPIPEEY-(Cha)-D-OH;

P574 (SEQ ID NO:12): (D-Cha)-Pro-Arg-$CH_2$(4-pyridylacetyl)-(Gly)$_4$-DFEEIPEEYLQ-OH;

P596 (SEQ ID NO:13) (BCH-2773): (D-Cha)-Pro-Arg-$CH_2$ (4-pyridylacetyl)-(GLY)$_4$-DYEPIPEEACha-(D)Glu-OH;

P597 (SEQ ID NO:14): (D-Cha)-Pro-Arg-$CH_2$(4-pyridylacetyl)-(Gly)$_4$-DFEEIPEEYLQ-OH;

P603 (SEQ ID NO:15): (D-Cha)-Pro-Arg-$CH_2$(4-pyridylacetyl)-Abu-Gly-DYEPIPEEA-(Cha)-)D-Glu)-OH;

P604 (SEQ ID NO:16): (D-Cha)-Pro-Arg-$CH_2$(4-pyridylacetyl)-Ava-Gly-DYEPIPEEA-(Cha)-(D-Glu)-OH;

P605 (SEQ ID NO:17): (D-Cha)-Pro-Arg-$CH_2$(4-pyridylacetyl)-Aca-Gly-DYEPIPEEA-(Cha)-(D-Glu)-OH;

P606 (SEQ ID NO:18) (BCH-2774): (D-Cha)-Pro-Arg-$CH_2$ (4-pyridylacetyl)-Aha-Gly-DYEPIPEEA-(Cha)-(D-Glu)-OH;

P609 (SEQ ID NO:19): (D-Cha)-Pro-Arg-$CH_2$(4-pyridylacetyl)-(Gly)$_4$-DYEPIPEEA-(Cha)-(D-Glu)-OH;

P617 (SEQ ID NO:20) (BCH-2772): H-(D-Phe)-Pro-Arg-$CH_2$SCH$_2$(CO)-(Gly)$_4$-DFEEPIEEYLQ-OH;

P618 (SEQ ID NO:21): Ac(D-Phe)-Pro-Arg-$CH_2$SCH$_2$(CO)-(Gly)$_4$-DFEEPIPEEYLQ-OH;

P658 (SEQ ID NO:22): (D-Cha)-Pro-Arg-$CH_2$(4-pyridylacetyl)-NH$(CH_2)_2$CO-Gly-DYEPIPEEA-(Cha)-(D-Glu)-OH;

P659 (SEQ ID NO:23): (D-Cha)-Pro-Arg-$CH_2$(4-pyridylacetyl)-Gly-Gly-DYEPIPEEA-(Cha)-(D-Glu)-OH;

P660 (SEQ ID NO:24): (D-Cha)-Pro-Arg-$CH_2$(4-pyridylacetyl)-NH$(CH_2)_3$CO-DYEPIPEEA-(Cha)-(D-Glu)-OH;

P661 (SEQ ID NO:25): (D-Cha)-Pro-Arg-$CH_2$(4-pyridylacetyl)-NH$(CH_2)_2$CO-DYEPIPEEA-(Cha)-(D-Glu)-OH;

BCH-2408 (SEQ ID NO:26): Ac(D-Phe)-Pro-Arg-$(CH_2)_2$(CO)-QSHNDGDFEPIPEEY-(Cha)-Q-OH;

BCH-2414 (SEQ ID NO:27): Ac(D-Phe)-Pro-Arg-$(CH_2)_4$(CO)—[NH—$CH_2$—CH=CH—$CH_2$—(CO)]$_2$-DEFPIPY-OH;

BCH-2423 (SEQ ID NO:28): succinyl(D-Phe)-Pro-Arg-$(CH_2)_2$(CO)-QSHNDGDFEEIPEEYLQ-OH;

BCH-2739 (SEQ ID NO:29): AC(D-Phe)-Pro-Arg-$(CH_2)_4$(CO)—[NH—$(CH_2)_4$(CO)]$_2$-DFEPIPL-OH;

BCH-2757 (SEQ ID NO:30): alpha-N-(Ac)(D-Phe)-Pro-Arg-$(CH_2)_4$(CO)—[NH—$(CH_2)_4$(CO)]-NGDFEPIPL-TFA salt;

BCH-2758 (SEQ ID NO:31): (D-Phe)-Pro-Arg-$(CH_2)_4$(CO)—[NH—$(CH_2)_4$(CO)]$_2$-DF-(4-thiahomoGlu)-PIPL-TFA salt;

BCH-2763 (SEQ ID NO:32): (D-Phe)-Pro-Arg-$(CH_2)_4$(CO)—[NH—$(CH_2)_4$(CO)]$_2$-DFEPIPL-TFA salt; and BCH-2767 (SEQ ID NO:33): (D-Phe)-Pro-Arg-$(CH_2)_4$(CO)—[NH—$(CH_2)_4$(CO)]$_2$-FEPIPL-TFA salt.

41. A thrombin inhibitor selected from the group consisting of:

P536 (SEQ ID NO:11): (D-Cha)-Pro-Arg-$CH_2$N(COCH$_3$) $CH_2$(CO)-(Gly)$_4$-DYEPIPEEY-(Cha)-D-OH;

P617 (SEQ ID NO:20) (BCH-2772): H-(D-Phe)-Pro-Arg-$CH_2$SCH$_2$(CO)-(Gly)$_4$-DFEEPIEEYLQ-OH; and P618 (SEQ ID NO:21): Ac(D-Phe)-Pro-Arg-$CH_2$SCH$_2$(CO)-(Gly)$_4$-DFEEPIPEEYLQ-OH.

42. A thrombin inhibitor selected from the group consisting of:

P574 (SEQ ID NO:12): (D-Cha)-Pro-Arg-$CH_2$(4-pyridylacetyl)-(Gly)$_4$-DFEEIPEEYLQ-OH;

P596 (SEQ ID NO:13) (BCH-2773): (D-Cha)-Pro-Arg-$CH_2$ (4-pyridylacetyl)-(GLY)$_4$-DYEPIPEEACha-(D)Glu-OH;

P597 (SEQ ID NO:14): (D-Cha)-Pro-Arg-$CH_2$(4-pyridylacetyl)-(Gly)$_4$-DFEEIPEEYLQ-OH;

P603 (SEQ ID NO:15): (D-Cha)-Pro-Arg-$CH_2$(4-pyridylacetyl)-Abu-Gly-DYEPIPEEA-(Cha)-)D-Glu)-OH;

P604 (SEQ ID NO:16): (D-Cha)-Pro-Arg-$CH_2$(4-pyridylacetyl)-Ava-Gly-DYEPIPEEA-(Cha)-(D-Glu)-OH;

P605 (SEQ ID NO:17): (D-Cha)-Pro-Arg-$CH_2$(4-pyridylacetyl)-Aca-Gly-DYEPIPEEA-(Cha)-(D-Glu)-OH;

P606 (SEQ ID NO:18) (BCH-2774): (D-Cha)-Pro-Arg-$CH_2$(4-pyridylacetyl)-Aha-Gly-DYEPIPEEA-(Cha)-(D-Glu)-OH;

P609 (SEQ ID NO:19): (D-Cha)-Pro-Arg-$CH_2$(4-pyridylacetyl)-(Gly)$_4$-DYEPIPEEA-(Cha)-(D-Glu)-OH;

P658 (SEQ ID NO:22): (D-Cha)-Pro-Arg-$CH_2$(4-pyridylacetyl)-$NH(CH_2)_2CO$-Gly-DYEPIPEEA-(Cha)-(D-Glu)-OH;

P659 (SEQ ID NO:23): (D-Cha)-Pro-Arg-$CH_2$(4-pyridylacetyl)-Gly-Gly-DYEPIPEEA-(Cha)-(D-Glu)-OH;

P660 (SEQ ID NO:24): (D-Cha)-Pro-Arg-$CH_2$(4-pyridylacetyl)-$NH(CH_2)_3CO$-DYEPIPEEA-(Cha)-(D-Glu)-OH; and P661 (SEQ ID NO:25): (D-Cha)-Pro-Arg-$CH_2$(4-pyridylacetyl)-$NH(CH_2)_2CO$-DYEPIPEEA-(Cha)-(D-Glu)-OH.

43. A thrombin inhibitor selected from the group consisting of:

P183 (SEQ ID NO:5): Ac(D-Phe)-Pro-Arg-$(CH_2)_4(CO)$—[NH—$CH_2$—CH=CH—$CH_2$—(CO)]-DFEPIPL-OH;

P184 (SEQ ID NO:6) (BCH-1710): Ac(D-Phe)-Pro-Arg-$(CH_2)_4(CO)$—[NH—$CH_2$—CH=CH—$CH_2$—(CO)]$_2$-DFEPIPL-OH;

P185 (SEQ ID NO:7): Ac(D-Phe)-Pro-Arg-$(CH_2)_4(CO)$—[NH—$CH_2$—CH=CH—$CH_2$—(CO)]$_3$-DFEPIPL-OH;

BCH-2414 (SEQ ID NO:27): Ac(D-Phe)-Pro-Arg-$(CH_2)_4$(CO)—[NH—$CH_2$—CH=CH—$CH_2$—(CO)]$_2$-DEFPIPY-OH;

BCH-2739 (SEQ ID NO:29): Ac(D-Phe)-Pro-Arg-$(CH_2)_4$(CO)—[NH—$(CH_2)_4$(CO)]$_2$-DFEPIPL-OH;

BCH-2757 (SEQ ID NO:30): alpha-N-(Ac)(D-Phe)-Pro-Arg-$(CH_2)_4$(CO)—[NH—$(CH_2)_4$(CO)]-NGDFEPIPL-TFA salt;

BCH-2758 (SEQ ID NO:31): (D-Phe)-Pro-Arg-$(CH_2)_4$(CO)—[NH—$(CH_2)_4$(CO)]$_2$-DF-(4-thiahomoGlu)-PIPL-TFA salt; and BCH-2763 (SEQ ID NO:32): (D-Phe)-Pro-Arg-$(CH_2)_4$(CO)—[NH—$(CH_2)_4$(CO)]$_2$-DFEPIPL-TFA salt.

44. A thrombin inhibitor selected from the group consisting of:

P79 (SEQ ID NO:1) (BCH-1709): Ac(D-Phe)-Pro-Arg-$(CH_2)_2$(CO)-QSHNDGDFEEIPEEYLQ-OH;

P103 (SEQ ID NO:3): Ac(D-Phe)-Pro-Arg-$(CH_2)_4$(CO)-QSHNDGDFEEIPEEYLQ-OH;

P311 (SEQ ID NO:9) (BCH-1721): Ac(D-Cha)-Pro-Arg-$(CH_2)_2$(CO)-QSHNDGDFEEIPEEYLQ-OH;

P314 (SEQ ID NO:10) (BCH-1726): Ac(D-Cha)-Pro-Arg-$(CH_2)_2$(CO)-QSHNDGDFEPIPEEY-(Cha)-Q-OH;

BCH-2408 (SEQ ID NO:26): Ac(D-Phe)-Pro-Arg-$(CH_2)_2$(CO)-QSHNDGDFEPIPEEY-(Cha)-Q-OH;

BCH-2414 (SEQ ID NO:27): Ac(D-Phe)-Pro-Arg-$(CH_2)_4$(CO)—[NH—$CH_2$—CH=CH—$CH_2$—(CO)]$_2$-DEFPIPY-OH;

BCH-2423 (SEQ ID NO:28): succinyl(D-Phe)-Pro-Arg-$(CH_2)_2$(CO)-QSHNDGDFEEIPEEYLQ-OH;

BCH-2763 (SEQ ID NO:32): (D-Phe)-Pro-Arg-$(CH_2)_4$(CO)—[NH—$(CH_2)_4$(CO)]$_2$-DFEPIPL-TFA salt;

P596 (SEQ ID NO:13) (BCH-2773): (D-Cha)-Pro-Arg-$CH_2$(4-pyridylacetyl)-(GLY)$_4$-DYEPIPEEACha-(D)Glu-OH; and P606 (SEQ ID NO:18) (BCH-2774): (D-Cha)-Pro-Arg-$CH_2$(4-pyridylacetyl)-Aha-Gly-DYEPIPEEA-(Cha)-(D-Glu)-OH.

45. A thrombin inhibitor selected from the group consisting of:

P314 (SEQ ID NO:10) (BCH-1726): Ac(D-Cha)-Pro-Arg-$(CH_2)_2$(CO)-QSHNDGDFEPIPEEY-(Cha)-Q-OH;

BCH-2408 (SEQ ID NO:26): Ac(D-Phe)-Pro-Arg-$(CH_2)_2$(CO)-QSHNDGDFEPIPEEY-(Cha)-Q-OH;

BCH-2763 (SEQ ID NO:32): (D-Phe)-Pro-Arg-$(CH_2)_4$(CO)—[NH—$(CH_2)_4$(CO)]$_2$-DFEPIPL-TFA salt;

P596 (SEQ ID NO:13) (BCH-2773): (D-Cha)-Pro-Arg-$CH_2$(4-pyridylacetyl)-(GLY)$_4$-DYEPIPEEACha-(D)Glu-OH; and P606 (SEQ ID NO:18) (BCH-2774): (D-Cha)-Pro-Arg-$CH_2$(4-pyridylacetyl)-Aha-Gly-DYEPIPEEA-(Cha)-(D-Glu)-OH.

46. A thrombin inhibitor:

BCH-2763 (SEQ ID NO:32): (D)Phe-Pro-Arg-$(CH_2)_4$(CO)—[$NH(CH_2)_4CO$]$_2$-DFEPIPL-TFA salt.

47. A pharmaceutical composition containing a compound according to claim 3 wherein said compound is present in admixture with a pharmaceutically acceptable carrier.

48. A pharmaceutical composition containing a compound according to claim 40 wherein said compound is present in admixture with a pharmaceutically acceptable carrier.

49. A pharmaceutical composition containing a compound according to claim 3 wherein said compound is present in admixture with another therapeutically active agent.

50. A pharmaceutical composition containing a compound according to claim 40 wherein said compound is present in admixture with another therapeutically active agent.

51. A method for the treatment or prevention of vascular diseases of a mammal, including human, comprising the administration of an effective amount of a compound according to claim 3.

52. A method for the treatment or prevention of vascular diseases of a mammal, including human, comprising the administration of an effective amount of a compound according to claim 40.

53. A method for the treatment or prevention of vascular diseases of a mammal, including human, comprising the administration of an effective amount of a composition according to anyone of claims 47 to 52.

* * * * *